United States Patent [19]

Malamas

[11] Patent Number: 4,927,831
[45] Date of Patent: May 22, 1990

[54] SPIRO-ISOQUINOLINE-PYRROLIDINE TETRONES AND ANALOGS THEREOF USEFUL AS ALDOSE REDUCTASE INHIBITORS

[75] Inventor: Michael S. Malamas, Jamison, Pa.

[73] Assignee: American Home Products, New York, N.Y.

[21] Appl. No.: 357,563

[22] Filed: May 26, 1989

Related U.S. Application Data

[63] Continuation-in-part of Ser. No. 260,434, Oct. 20, 1988, abandoned.

[51] Int. Cl.$^5$ .................... A61K 31/47; C07D 471/10
[52] U.S. Cl. ...................................... 514/278; 546/18; 546/19; 540/521; 544/5; 544/6; 544/71; 514/222.5; 514/226.5; 514/215; 514/234.2
[58] Field of Search .................. 546/18, 19; 540/521; 544/5, 6, 71; 514/222.5, 226.5, 215, 234.2, 278

[56] References Cited

FOREIGN PATENT DOCUMENTS

| 2544317 | 10/1984 | France | 546/18 |
| 41586 | 12/1970 | Japan | 544/6 |
| 41587 | 12/1977 | Japan | 544/6 |
| 2133401A | 7/1984 | United Kingdom | 546/19 |

Primary Examiner—Robert T. Bond
Attorney, Agent, or Firm—Walter Patton

[57] ABSTRACT

This invention relates to spiro-isoquinoline-pyrrolidine tetrones and their pharmaceutically acceptable salts thereof, to processes for their preparation, to methods for using the compounds, and to pharmaceutical preparations thereof. The compounds have pharmaceutical properties which render them beneficial for the prevention of diabetes mellitus associated complications.

30 Claims, No Drawings

SPIRO-ISOQUINOLINE-PYRROLIDINE TETRONES AND ANALOGS THEREOF USEFUL AS ALDOSE REDUCTASE INHIBITORS

This is a continuation-in-part of copending U.S. Ser. No. 260,434, filed Oct. 20, 1988, now abandoned.

BACKGROUND OF THE INVENTION

This invention relates to spiro-isoquinoline-pyrrolidine tetrones and their pharamaceutically acceptable salts thereof, to processes for their preparation, to methods for using the compounds, and to pharmaceutical preparations thereof. The compounds have pharmaceutical properties which render them beneficial for the prevention or treatment of complications associated with diabetes mellitus.

The use of insulin and/or oral hypoglycemic agents in the treatment of diabetes mellitus has prolonged the life of many of these patients. However, their use has not had a demonstrable impact on the development of diabetic complications such as neuropathy, nephropathy, retinopathy, cataracts and vascular disease which accompany the underlying metabolic disorder. There is little question that chronic hyperglycemia plays a major role in the genesis of these complications, and that complete normalization of blood glucose would likely prevent most if not all complications. For a number of reasons, though, chronic normalization of blood glucose has not been achieved with the currently available therapies. The development of diabetic complications has recently been linked to the increased accumulation of tissue sorbitol resulting from chronic hyperglycemia. Therapeutic reduction of sorbitol accumulation could potentially prevent the development of diabetic complications.

In mammals, including humans, the key enzyme involved in the conversion of glucose to sorbitol (e.g. the sorbitol pathway) is aldose reductase. J.H. Kinoshita and collaborators [see J.H. Kinoshita et al, Biochem. Biophys. Acta, 158, 472 (1968) and references cited therein] have demonstrated that this enzyme plays a central role in the etilogy of galactosemic cataracts by effecting the conversion of galactose to dulcitol (galactitol), and that an agent capable of inhibiting aldose reductase can prevent the detrimental accumulation of dulcitol in the lens. Furthermore, a relationship between elevated levels of glucose and an undesirable accumulation of sorbitol has been demonstrated in the lens, peripheral nerves and kidney of diabetic animals [see A. Pirie and R. van Heyningen, Exp. Eye Res., 3, 124 (1964); L.T. Chylack and J.H. Kinoshita, Invest. Ophthal., 8, 401 (1969) and J.D. Ward and R.W.R. Baker, Diabetol., 6, 531 (1970)].

PRIOR ART

The closest prior art is European Patent No. 168,181-A and French Patent No. 2,544,317.

European Patent No. 168,181-A discloses 1-(4-bromo-2-fluorophenylmethyl-7-chlorospiro-(indole-3,3'-pyrrolidine)-2,2',5'-trione of formula

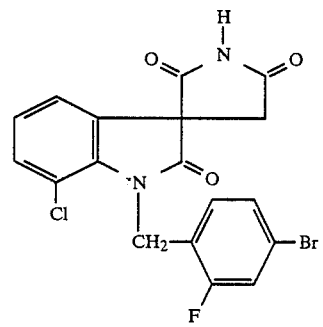

useful as an aldose reductase inhibitor for treating complications of diabetes and galactosemia.

French Patent No. 2,544,317 discloses compounds of formula

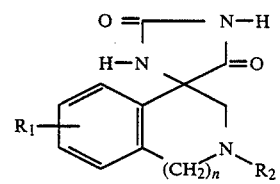

wherein $R_1$ represents hydrogen, halogen, hydroxy or methoxy; $R_2$ represents hydrogen, lower alkyl, phenyl lower alkyl, alcanoyl or p-toluenesulfonyl, useful as aldose reductase inhibitors.

SUMMARY OF THE INVENTION

The spiro-isoquinoline-pyrrolidine tetrones and their analogs of the present invention are represented by formula (I):

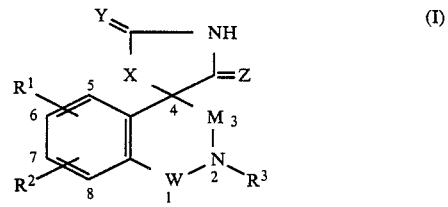

wherein $R^1$ and $R^2$ are independently hydrogen, alkyl containing 1 to 6 carbon atoms, halogen, lower alkoxy containing 1 to 6 carbon atoms, trifluoromethyl, lower alkylthio wherein lower alkyl contains 1 to 6 carbon atoms, dialkylamino wherein alkyl contains 1 to 6 carbon atoms, nitro, aryl or aryl (lower alkyl) oxy wherein aryl contains 6 to 10 carbon atoms and lower alkyl contains 1 to 6 carbon atoms; $R^3$ is hydrogen, lower alkyl containing 1 to 6 carbon atoms, aryl, aryl (lower alkyl) or halogen substituted aryl (lower alkyl) wherein aryl contains 6 to 10 carbon atoms and lower alkyl contains 1 to 6 carbon atoms, acyl or heterocyclic (lower alkyl) of structural formula

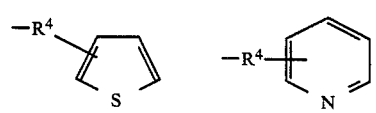

wherein R⁴ is lower alkylene containing 1 to 3 carbon atoms; X is lower alkylene containing 1 to 3 carbon atoms, oxygen, sulfur or nitrogen; Y and Z are oxygen or sulfur; M and W are carbonyl, thiocarbonyl, sulfonyl, sulfoxo or lower alkylene containing 1 to 2 carbon atoms, with the proviso that M and W are not both lower alkylene when X is nitrogen, and the pharmaceutically acceptable salts thereof. The fused benzene ring can be replaced by thiophene, pyridine or furan.

A preferred group of compounds of the present invention is represented by formula (II)

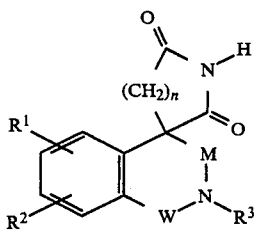

(II)

wherein R¹ and R² are independently hydrogen, alkyl containing 1 to 6 carbon atoms, halogen, lower alkoxy containing 1 to 6 carbon atoms, trifluoromethyl, lower alkylthio wherein lower alkyl contains 1 to 6 carbon atoms; R³ is hydrogen, lower alkyl containing 1 to 6 carbon atoms; M and W are carbonyl or thiocarbonyl; n is 1 to 3, and the pharmaceutically acceptable salts thereof.

A second preferred group of compounds of the present invention is represented by formula (II)

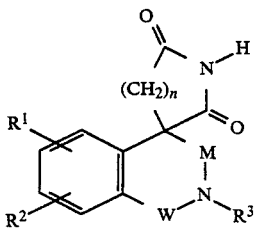

(II)

wherein R¹ and R² are independently hydrogen, alkyl containing 1 to 6 carbon atoms, halogen, lower alkoxy containing 1 to 6 carbon atoms, trifluoromethyl, lower alkylthio wherein lower alkyl contains 1 to 6 carbon atoms; R³ is lower alkyl, aryl-(lower alkyl) or dihalogen substituted aryl-(lower alkyl) wherein aryl contains 6 to 10 carbon atoms and lower alkyl contains 1 to 6 carbon atoms; M and W are carbonyl or thiocarbonyl; n is 1 to 3, and the pharmaceutically acceptable salts thereof.

A still further preferred group of compounds of the present invention is represented by formula (III)

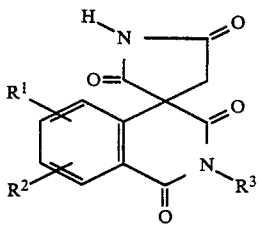

(III)

wherein R¹ and R² are hydrogen or halogen; R³ is lower alkyl containing 1 to 6 carbon atoms, benzyl or dihalogen substituted benzyl, and the pharmaceutically acceptable salts thereof.

The most preferred compounds of the present invention are set forth below:

2-[(4-bromo-2-fluorophenyl)methyl]spiro[isoquinoline-4(1H),3'-pyrrolidine]1,2',3,5'(2H)-tetrone;

[2-[(4-bromo-2-fluorophenyl)methyl]-7-chloro]-spiro[isoquinoline-4(1H),3'-pyrrolidine]-1,2',3,5'(2H)-tetrone;

[2-[(4-bromo-2-fluorophenyl)methyl]-6-chloro]-spiro[isoquinoline-4(1H),3'-pyrrolidine)-1,2',3,5'(2H)-tetrone;

[2-[4-bromo-2-fluorophenyl)methyl]-5-fluoro]-spiro[isoquinoline-4(1H),3'-pyrrolidine]-1,2',3,5'(2H)-tetrone;

[2-[(4-bromo-2-fluorophenyl)methyl]-6-fluoro]-spiro[isoquinoline-4(1H),3'-pyrrolidine]-1,2',3,5'(2H)-tetrone;

[2-[(4-bromo-2-fluorophenyl)methyl]-7-fluoro]-spiro[isoquinoline-4-(1H),3'-pyrrolidine]-1,2',3,5'(2H)-tetrone;

[2-[(4-bromo-2-fluorophenyl)methyl]-8-fluoro]-spiro[isoquinoline-4(1H),3'-pyrrolidine]-1,2',3,5'(2H)-tetrone;

[6-bromo-2-[(4-bromo-2-fluorophenyl)methyl]-7-methoxy]spiro[isoquinoline-4(1H),3'-pyrrolidine]-1,2',3,5'(2H)-tetrone;

[2-[(4-bromo-2-fluorophenyl)methyl]-7-methoxy]-spiro[isoquinoline-4(1H),3'-pyrrolidine]-1,2',3,5'(2H)-tetrone;

(R)-(+)-2-[(4-bromo-2-fluorophenyl)methyl]-spiro[isoquinoline-4(1H),3'-pyrrolidine]-1,2',3,5'(2H)-tetrone;

(S)-(−)-2-[(4-bromo-2-fluorophenyl)methyl]-spiro[isoquinoline-4(1H),3'-pyrrolidine]-1,2',3,5'(2H)-tetrone;

(R)-(+)-[2-[(4-bromo-2-fluorophenyl)methyl]-6-fluoro]spiro[isoquinoline-4(1H),3'-pyrrolidine]-1,2',3,5'(2H)-tetrone;

(S)-(−)-[2-[(4-bromo-2-fluorophenyl)methyl]-6-fluoro]-spiro[isoquinoline-4(1H),3'-pyrrolidine]-1,2',3,5'(2H)-tetrone;

2-[(3,4-dichlorophenyl)methyl]spiro[isoquinoline-4(1H),3'-pyrrolidine]-1,2',3,5'(2H)-tetrone;

2-methylspiro[isoquinoline-4(1H),3'-pyrrolidine]-1,2',3,5'(2H)-tetrone;

6-chloro-2-methylspiro[isoquinoline-4(1H),3'-pyrrolidine]-1,2',3,5'(2H)-tetrone;

6-bromo-2-methylspiro[isoquinoline-4(1H),3'-pyrrolidine]-1,2',3,5'(2H)-tetrone;

7-chloro-2-methylspiro[isoquinoline-4(1H),3'-pyrrolidine]-1,2',3,5'(2H)-tetrone;

2-ethylspiro[isoquinoline-4(1H),3'-pyrrolidine]-1,2',3,5'(2H)-tetrone;

2-propylspiro[isoquinoline-4(1H),3'-pyrrolidine]-1,2',3,5'(2H)-tetrone;

2-butylspiro[isoquinoline-4(1H),3'-pyrrolidine]-1,2',3,5'(2H)-tetrone;

and the pharmaceutically acceptable salts thereof.

The compounds of formula (I) all possess at least one asymmetric carbon atom, namely the spiro carbon atom at position 3' of the pyrrolidine ring. The compounds of formula (I) therefore exist, and may be isolated, in two or more stereoisomeric forms. This invention encompasses the compounds of formula (I) in racemic form or in any optically active form.

The spiro-isoquinoline-pyrrolidine tetrones and their enantiomers were prepared by the processes described hereinafter.

A method is provided for preventing or relieving diabetes mellitus associated complications in a diabetic mammal by administering to said mammal a prophylactic or alleviating amount of the compounds of formula (I). Such complications include neuropathy, nephropathy, retinopathy, keratopathy, diabetic uveitis, and cataracts.

The compounds of formula (I), when admixed with a pharmaceutically acceptable carrier, forms a pharmaceutical composition which can be used according to the preceding method.

DETAILED DESCRIPTION OF THE INVENTION

The compounds of formula (I) form salts with suitable therapeutically acceptable inorganic and organic bases. These derived salts possess the same activity as their parent compound and are included within the scope of this invention. The compounds of formula (I) are transformed in excellent yield into the corresponding therapeutically acceptable salts by neutralization with the appropriate inorganic or organic base. The salts are administered usually in the same manner as the parent compounds. Suitable inorganic bases to form these salts include, for example, the hydroxides, carbonates or bicarbonates of the therapeutically acceptable alkali metals or alkaline earth metals, for example, sodium, potassium, magnesium, calcium and the like. Suitable organic bases include the following amines: benzylamine; lower mono-, di-, and trialkylamines, the alkyl radicals of which contain up to three carbon atoms, such as methylamine, dimethylamine, trimethylamine, ethylamine, di- and triethylamine, methylethylamine, and the like; mono-, di-, and trialkanolamines, the alkanol radicals of which contain up to three carbon atoms, for example, mono-, di-, and triethanolamine; alkylenediamines which contain up to six carbon atoms, such as hexamethylenediamine; cyclic saturated or unsaturated bases containing up to six carbon atoms, such as pyrrolidine, piperidine, morpholine, piperazine and their N-alkyl and N-hydroxyalkyl derivatives, such as N-methyl-morpholine and N-(2-hydroxyethyl)-piperidine, as well as pyridine. Furthermore, there may be mentioned the corresponding quaternary salts, such as the tetraalkyl (for example tetramethyl), alkyl-alkanol (for example methyl-triethanol and trimethyl-monoethanol) and cyclic ammonium salts, for example the N-methyl-pyridinium, N-methyl-N-(2-hydroxyethyl)-morpholinium, N,N-dimethyl-morpholinium, N-methyl-N-(2-hydroxyethyl)-morpholinium, N,N-dimethyl-piperidinium salts, which are characterized by having good water-solubility. In principle, however, there can be used all the ammonium salts which are physiologically compatible.

The transformations to the salts can be carried out by a variety of methods known in the art. For example, in the case of the inorganic salts, it is preferred to dissolve the compound of formula (I) in water containing at least one equivalent amount of hydroxide, carbonate, or bicarbonate corresponding to the inorganic salt desired. Advantageously, the reaction is performed in a water-miscible, inert organic solvent, for example, methanol, ethanol, dioxane, and the like in the presence of water. For example, such use of sodium hydroxide, sodium carbonate or sodium bicarbonate gives a solution of the sodium salt. Evaporation of the solution or addition of a water-miscible solvent of a more moderate polarity, for example, a lower alkanol, for instance, butanol, or a lower alkanone, for instance, ethyl methyl ketone, gives the solid inorganic salt if that form is desired.

To produce an amine salt, the acidic compound of formula (I) is dissolved in a suitable solvent of either moderate or low polarity, for example, ethanol, methanol, ethyl acetate, diethyl ether and benzene. At least an equivalent amount of the amine corresponding to the desired cation is then added to that solution. If the resulting salt does not precipitate, it can usually be obtained in solid form by addition of a miscible diluent of lower polarity, for example, benzene or petroleum ether, or by evaporation. If the amine is relatively volatile, any excess can easily be removed by evaporation. It is preferred to use substantially equivalent amounts of the less volatile amines.

Salts wherein the cation is quaternary ammonium are produced by mixing the compound of formula (I) with an equivalent amount of the corresponding quaternary ammonium hydroxide in water solution, followed by evaporation of the water.

The spiro-isoquinoline-pyrrolidine tetrones of this invention may be administered to mammals, for example, man, cattle, or rabbits, either alone or in dosage forms, i.e., capsules or tablets, combined with pharmacologically acceptable excipients.

The compounds of this invention may be given orally. However, the method of administering the present active ingredients of this invention is not to be construed as limited to a particular mode of administration. For example, the compounds may be administered topically directly to the eye in the form of drops of sterile, buffered ophthalmic solutions, preferably of pH 7.2–7.6. Also, they may be administered orally in solid form containing such excipients as starch, milk sugar, certain types of clay and so forth. They may also be administered orally in the form of solutions or they may be injected parenterally. For parenteral administration they may be used in the form of a sterile solution, preferably of pH 7.2–7.6, containing a pharmaceutically acceptable buffer.

The dosage of the spiro-isoquinoline-pyrrolidine tetrones will vary with the form of administration and the particular compound chosen. Furthermore, it will vary with the particular host under treatment. Generally, treatment is initiated with small dosages substantially less than the optimal dose of the compound. Thereafter, the dosage is increased by small increments until efficacy is obtained. In general, the compounds of this invention are most desirably administered at a concentration level that will generally afford effective results without causing any harmful or deleterious side effects. For topical administration, a 0.05–1.0% solution may be administered dropwise in the eye. The frequency of instillation varies with the subject under treatment from a drop every two or three days to once daily. For oral or parenteral administration a preferred level of dosage ranges from about 0.1 mg to about 1.0 mg per kilo of body weight per day, although aforementioned variations will occur. However, a dosage level that is in the range of from about 0.1 mg to about 1.0 mg per kilo of body weight per day is most satisfactory.

Unit dosage forms such as capsules, tablets, pills and the like may contain from about 5.0 mg to about 25.0 mg of the active ingredients of this invention with a pharmaceutical carrier. Thus, for oral adminsitration, capsules can contain from between about 5.0 mg to about 25.0 mg of the active ingredients of this invention with or without a pharmaceutical diluent. Tablets, either effervescent or noneffervescent, can contain between about 5.0 to 25.0 mg of the active ingredients of this invention together with conventional pharmaceutical carriers. Thus tablets, which may be coated and either effervescent or noneffervescent, may be prepared according to the known art. Inert diluents or carriers, for example, magnesium carbonate or lactose, can be used together with conventional disintegrating agents for example, magnesium stearate.

The spiro-isoquinoline-pyrrolidine tetrones also can be used in combination with insulin or oral hypoglycemic agents to produce a beneficial effect in the treatment of diabetes mellitus. In this instance, commercially available insulin preparations or oral hypoglycemic agents, exemplified by acetohexamide, chlorpropamide, tolazamide, tolbutamide and phenformin, are suitable. The compounds hereof can be administered sequentially or simultaneously with insulin or the oral hypoglycemic agent. Suitable methods of administration, compositions and doses of the insulin preparation or oral hypoglycemic agent are described in medical textbooks; for instance, *Physicians' Desk Reference*, 42 ed., Medical Economics Co., Oradell, N.J., U.S.A., 1988.

The aldose reductase inhibiting property of the compounds of this invention and the utilization of the compounds in preventing, diminishing and alleviating diabetic complications are demonstrable in experiments using galactosemic rats, see Dvornik et al., Science, 182, 1146 (1973). Such experiments are exemplified hereinbelow after the listing of the following general comments pertaining to these experiments:

(a) Four or more groups of six male rats, 50–70 g, Sprague-Dawley strain, were used. The first group, the control group, was fed a mixture of laboratory chow (rodent Laboratory Chow, Purina) and glucose at 20% (w/w %) concentration. An untreated galactosemic group was fed a similar diet in which galactose was substituted for glucose. The third group was fed a diet prepared by mixing a given amount of the test compound with the galactose containing diet. The concentration of galactose in the diet of the treated groups was the same as that for the untreated galactosemic group.

(b) After four days, the animals were killed by euthanization. Both the lens and sciatic nerve were removed, weighed and stored frozen for polyol determination.

(c) The polyol determination was performed by a modification of the procedure of M. Kraml and L. Cosyns, Clin. Biochem., 2,373 (1969). Only two minor reagent changes were made: (a) The rinsing mixture was an aqueous 5% (w/v) trichloroacetic acid solution and (b) the stock solution was prepared by dissolving 25 mg of dulcitol in 100 ml of an aqueous trichloroacetic acid solution. [N.B.: For each experiment the average value found in the tissue from rats fed the glucose diet was subtracted from the individual values found in the corresponding tissue in galactose-fed rats to obtain the amount of polyol accumulated.] The aldose reductase inhibiting effects of the compounds of formula (I) were also tested by employing an in vitro testing procedure similar to that described by S. Hayman and J.H. Kinoshita, J. Biol. Chem., 240,877 (1965). In the present case the procedure of Hayman and Kinoshita was modified in that the final chromatography step was omitted in the preparation of the enzyme from bovine lens.

The following tabulated results show that the spiro-isoquinoline-pyrrolidine tetrones of this invention show the property that they are active both in vitro and in vivo and diminish the accumulation of dulcitol in the lenses and sciatic nerves of rats fed galactose. The figures under L and N represent the percentage decrease of dulcitol accumulation in the tissues of the lens and sciatic nerve, respectively, for treated rats as compared to untreated rats.

TABLE 1

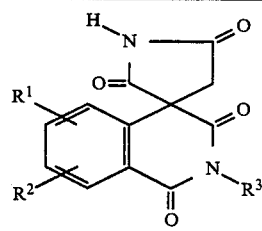

(III)

| $R^1$ | $R^2$ | $R^3$ | % Inhibition IN VITRO | | | | % Lowering Dulcitol Accumulation IN VIVO | | |
|---|---|---|---|---|---|---|---|---|---|
| | | | $10^{-5}$M | $10^{-6}$M | $10^{-7}$M | $4 \times 10^{-8}$M | mg/kg | (%)L | (%)N |
| —H | —H | 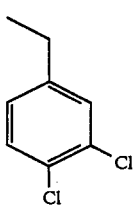 | 100 | 97 | 87 | 42 | 1.0 | 10.0 | 64.0 |
| | | | | | | | 3.0 | 18.0 | 76.0 |
| | | | | | | | 10.0 | 35.0 | 92.0 |
| | | | | | | | 48.0 | 41.0 | 85.0 |

TABLE 1-continued
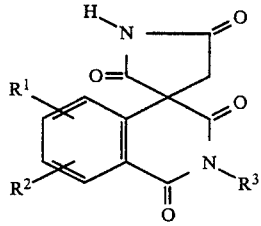
(III)
| R¹ | R² | R³ | % Inhibition IN VITRO | | | | % Lowering Dulcitol Accumulation IN VIVO | | |
|---|---|---|---|---|---|---|---|---|---|
| | | | $10^{-5}$M | $10^{-6}$M | $10^{-7}$M | $4 \times 10^{-8}$M | mg/kg | (%)L | (%)N |
| —H | —H | 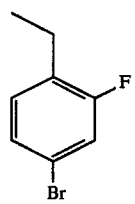 | 96 | 94 | 94 | 51 | 0.1 | NS | 26.0 |
| | | | | | | | 0.3 | NS | 60.0 |
| | | | | | | | 0.5 | 12.0 | 82.0 |
| | | | | | | | 1.0 | 16.0 | 95.0 |
| 6-Cl | —H | 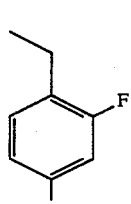 | 97 | 92 | 55 | 8 | 0.6 | 9 | 29 |
| —H | 7-Cl | 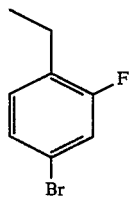 | 96 | 92 | 42 | 25 | 0.6 | NS | 63 |
| 5-F | —H | 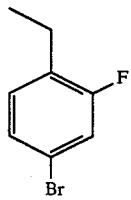 | 98 | 98 | 92 | 44 | 0.5 | 14.2 | 52.5 |
| | | | | | | | 1.0 | 23.9 | 77.0 |
| 6-F | —H | 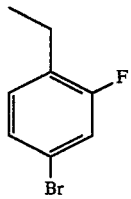 | 97 | 96 | 86 | 38 | 0.3 | NS | 39.7 |
| | | | | | | | 0.5 | NS | 82.9 |
| | | | | | | | 0.5 | NS | 92.1 |
| | | | | | | | 0.9 | NS | 93.5 |
| —H | 7-F | 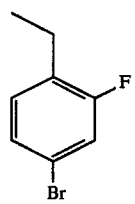 | 95 | 93 | 92 | 42 | 0.5 | NS | NS |
| | | | | | | | 1.0 | NS | 50.2 |

TABLE 1-continued
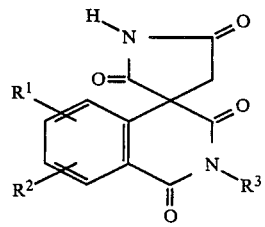
(III)
| R¹ | R² | R³ | % Inhibition IN VITRO | | | | % Lowering Dulcitol Accumulation IN VIVO | | |
|---|---|---|---|---|---|---|---|---|---|
| | | | $10^{-5}M$ | $10^{-6}M$ | $10^{-7}M$ | $4 \times 10^{-8}M$ | mg/kg | (%)L | (%)N |
| —H | 8-F | 2-F,4-Br-benzyl | 96 | 94 | 92 | 43 | 0.5 | NS | 50.6 |
| | | | | | | | 1.0 | 16.3 | 57.6 |
| —H | 7-OCH₃ | 2-F,4-Br-benzyl | 97 | 96 | 90 | 72 | 25.7 | 45.3 | 88.1 |
| 6-Br | 7-OCH₃ | 2-F,4-Br-benzyl | 98 | 97 | 88 | 70 | 0.5 | NS | 55.2 |
| | | | | | | | 26.4 | 48.8 | 89.5 |
| (S)-(−) —H | —H | 2-F,4-Br-benzyl | 87 | 51 | — | — | 0.5 | NS | NS |
| | | | | | | | 4.8 | NS | 83 |
| (R)-(+) —H | —H | 2-F,4-Br-benzyl | 96 | 93 | 91 | 87 | 0.5 | NS | 83 |
| | | | | | | | 5.1 | NS | 100 |
| (S)-(−) —H | —F | 2-F,4-Br-benzyl | 98 | 97 | 46 | 29 | 0.4 | NS | 40 |
| | | | | | | | 0.8 | 21 | 70 |

TABLE 1-continued

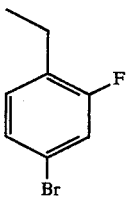

| R[1] | R[2] | R[3] | % Inhibition IN VITRO | | | | % Lowering Dulcitol Accumulation IN VIVO | | |
|---|---|---|---|---|---|---|---|---|---|
| | | | $10^{-5}M$ | $10^{-6}M$ | $10^{-7}M$ | $4 \times 10^{-8}M$ | mg/kg | (%)L | (%)N |
| (R)-(+) —H | —F | (2-ethyl-4-bromo-6-fluorophenyl) | 99 | 95 | 93 | 93 | 0.4 | 31 | 100 |
| | | | | | | | 0.8 | 26 | 100 |
| —H | —H | —CH$_3$ | 95 | 91 | 63 | 38 | 1.0 | 15.0 | 37.0 |
| | | | | | | | 3.0 | 43.0 | 66.0 |
| | | | | | | | 10.0 | 62.0 | 79.0 |
| | | | | | | | 43.0 | 86.0 | 89.0 |
| 6-Cl | —H | —CH$_3$ | 93 | 94 | 73 | 43 | 1 | 33 | 75 |
| | | | | | | | 3 | 59 | 75 |
| 6-Br | —H | —CH$_3$ | 100 | 100 | 85 | 43 | 1 | NS | 54 |
| —H | 7-Cl | —CH$_3$ | 95 | 92 | 61 | 34 | 3 | 14 | 21 |
| —H | —H | —CH$_2$CH$_3$ | 96 | 76 | 27 | 17 | 11 | NS | NS |
| —H | —H | —(CH$_2$)$_2$CH$_3$ | 94 | 62 | 19 | 8 | 11 | NS | NS |
| —H | —H | —(CH$_2$)$_3$CH$_3$ | 99 | 86 | 17 | 19 | 10 | NS | NS |

NS = statistically non-significant change

PROCESS A

The spiro-isoquinoline-pyrrolidine tetrones of the present invention were prepared by the following reaction scheme,

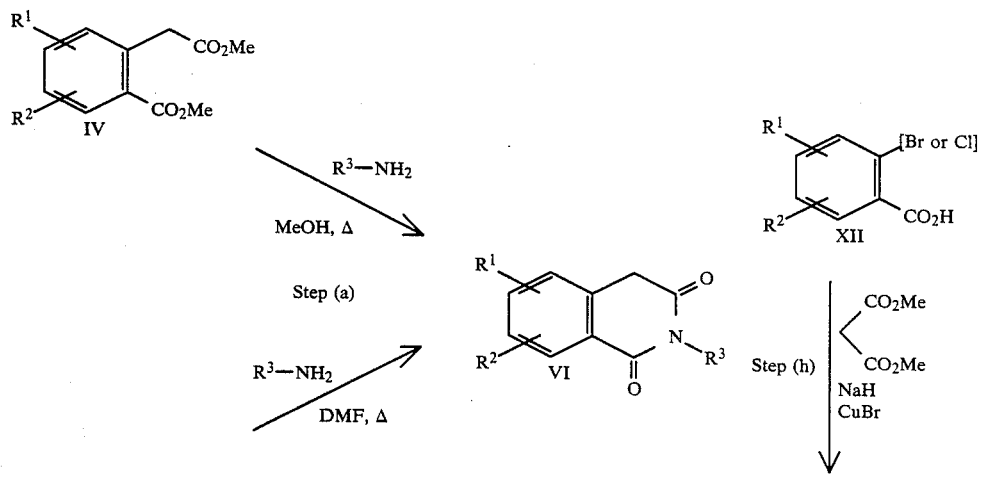

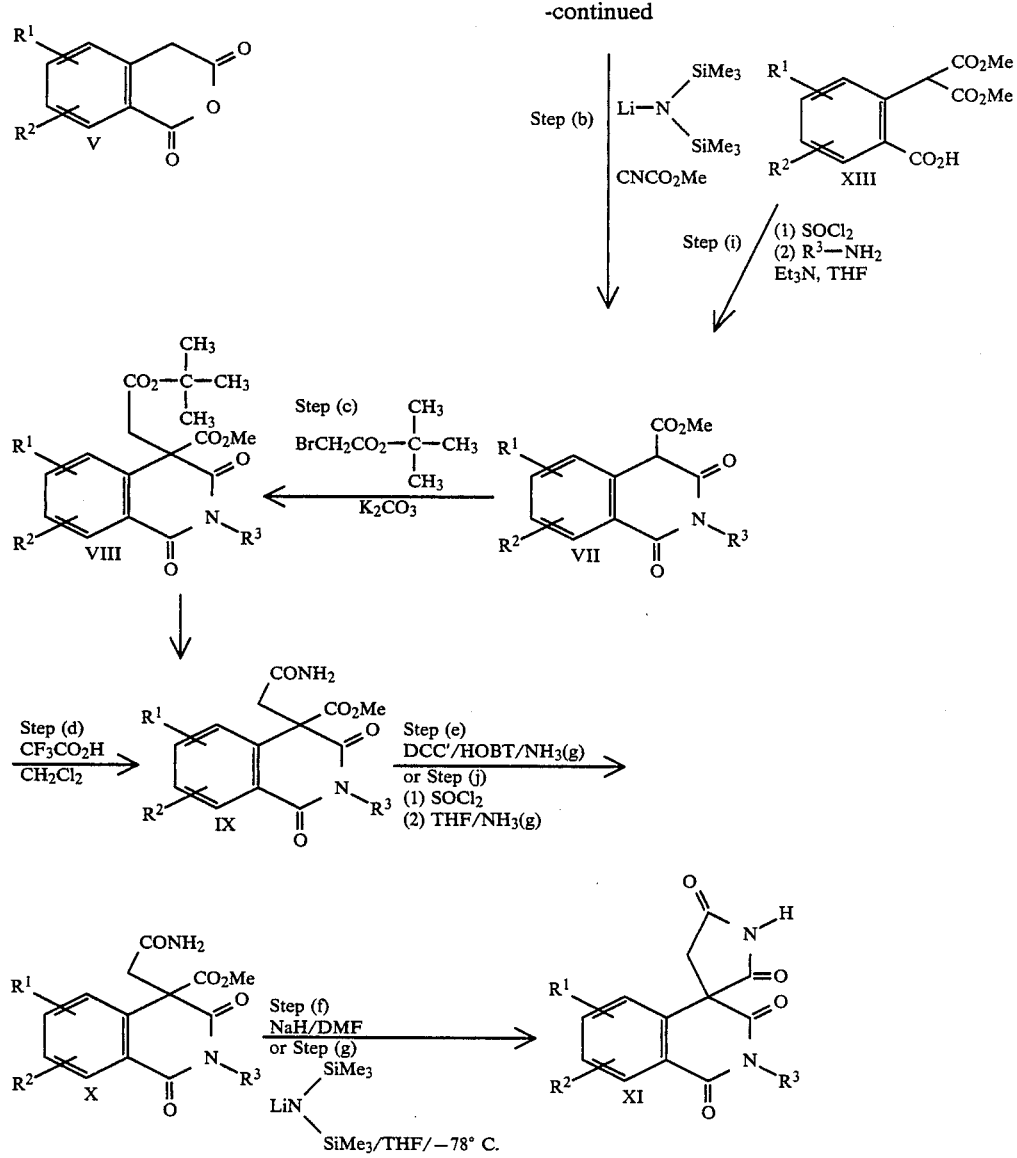

wherein R¹ and R² are hydrogen or halogen; R³ is alkyl containing 1 to 6 carbon atoms, aryl (lower alkyl) or dihalogen substituted aryl (lower alkyl) wherein aryl contains 6 to 10 carbon atoms and lower alkyl contains 1 to 6 carbon atoms. The process of the production of the compounds of formula (I) wherein R¹ and R² are chlorine or hydrogen; X is methylene; Y,Z are oxygen; M,W are carbonyl; R³ is alkyl (methyl, ethyl, propyl, butyl) or aralkyl (3,4-dichlorobenzyl, or 4-bromo-2-fluorobenzyl) comprises:

Step (a) Reacting either homophthalic acid dimethyl ester of formula (IV) or homophthalic anhydride of formula (V) wherein R¹ and R² are as defined above with an amine R³—NH₂ wherein R³ is as defined above to produce the homophthalimide of formula (VI) wherein R¹, R², R³ are as defined above.

The homophthalic acid dimethyl esters of formula (IV) and the homophthalic anhydrides of formula (V) required for the present invention are commercially available compounds or can be prepared by known methods.

The homophthalic acid dimethyl ester compound (IV) can be reacted with a saturated methanolic ammonium solution in a pressure vessel and temperature in the range of 60°–80° C. The homophthalic anhydride compound (V) can be reacted with an amine at high temperature 160°–180° C. in a conventional solvent which does not adversely influence the reaction such as N,N-dimethyformamide. However, reaction of a volatile amine with the homophthalic anhydride compound (V) can be produced by reaction of a saturated tetrahydrofuran solution of the appropriate amine with homophthalic anhydride at room temperature and subsequent removal of the volatile solvent, and introduction of N,N-dimethylformamide as the solvent.

Further reaction at high temperature (160°–180° C.) is required to produce the compound of formula (VI).

Step (b) The compound of formula (VI) wherein R¹, R², R³ are as defined above is reacted with a base, for example, lithium bis(trimethylsilyl)amide in a conventional solvent which does not adversely influence the reaction, for example, tetrahydrofuran, and subsequent addition of a reactive carbomethoxylating agent such as methyl cyanoformate to produce the compound of formula (VII) wherein $R^1$, $R^2$, $R^3$ are as defined above.

Step (c) The compound of formula (VII), wherein $R^1$, $R^2$, $R^3$ are as defined above, is reacted with an inorganic base such as potassium carbonate in a conventional solvent which does not adversely influence the reaction, for example, N,N-dimethyformamide, and subsequent addition of the tert-butyl bromoacetate produces the compound of the formula (VIII), wherein $R^1$, $R^2$, $R^3$ are as defined above.

Step (d) The compound of formula (VIII), wherein $R^1$, $R^2$, $R^3$ are as defined above, is hydrolyzed with an organic acid such as trifluoroacetic acid in a conventional solvent which does not adversely influence the reaction, for example, methylene chloride, to produce the compound of formula (IX), wherein $R^1$, $R^2$, $R^3$ are as defined above.

Step (e) The compound of formula (IX), wherein $R^1$, $R^2R^3$ are as defined above, is reacted with a coupling agent such as 1-(2-dimethylaminopropyl)-2-ethylcarbodiimide DCC'/1-hydroxybenzotriazole, (HOBT) in a conventional solvent which does not adversely influence the reaction, for example, N,N-dimethylformamide, and subsequent addition of tetrahydrofuran ammonium solution produces the compound of the formula (X), wherein $R^1$, $R^2$, $R^3$ are as defined above.

Step (f) The compound of formula (X), wherein $R^1$ and $R^2$ are as defined above, and $R^3$ is an appropriately substituted aralkyl as defined above is reacted with a base such as sodium hydride in a conventional solvent which does not adversely influence the reaction, for example, N,N-dimethylformamide, to produce the compound of the formula (XI), wherein $R^1$, $R^2$ are as defined above, $R^3$ is an appropriately substituted aralkyl as defined above.

When $R^3$ is an alkyl as defined above, the process of Step (f) produces very low yields.

Step (g) The compound of formula (X), wherein $R^1$, $R^2$ are as defined above, $R^3$ is an alkyl as defined above, is reacted with a base such as lithium bis(trimethylsilyl)amide, in a conventional solvent which does not adversely influence the reaction, for example, tetrahydrofuran, at low temperature ($-78°$ C.) to produce the compound of the formula (XI), wherein $R^1$, $R^2$ are as defined above, $R^3$ is an alkyl, as defined above.

Step (h) Reacting either 2-bromobenzoic acid or 2chlorobenzoic acid of formula (XII) wherein $R^1$ and $R^2$ are as defined above with dimethyl malonate and NaH in the presence of a catalytic amount of CuBr to produce the propanedioic acid dimethyl ester of formula (XIII) wherein $R^1$, $R^2$ $R^3$ are as defined above.

The 2-bromobenzoic acids or 2-chlorobenzoic acids of formula (XII) required for the present invention are commercially available compounds or can be prepared by known methods.

Step (i) The propanedioic acid dimethyl ester of formula (XIII) can be reacted with thionyl chloride under refluxing conditions to produce the corresponding acid chloride which upon treatment with an amine $R^3-NH_2$ in the presence of triethylamine in a conventional solvent which does not adversely influence the reaction, for example, tetrahydrofuran, can produce the compound of formula (VII) wherein $R^1$, $R^2$ and $R^3$ are as defined above.

Step (j) The compound of formula (IX), wherein $R^1$, $R^2$ and $R^3$ are as defined above, can be reacted with thionyl chloride under refluxing conditions to produce the corresponding acid chloride, which upon treatment with a saturated tetrahydrofuran ammonium solution can produce the compound of formula (X), wherein $R^1$, $R^2$ and $R^3$ are as defined above.

PROCESS B

The enantiomers of the spiro-isoquinoline-pyrrolidine tetrones of the present invention were prepared by the following reaction scheme,

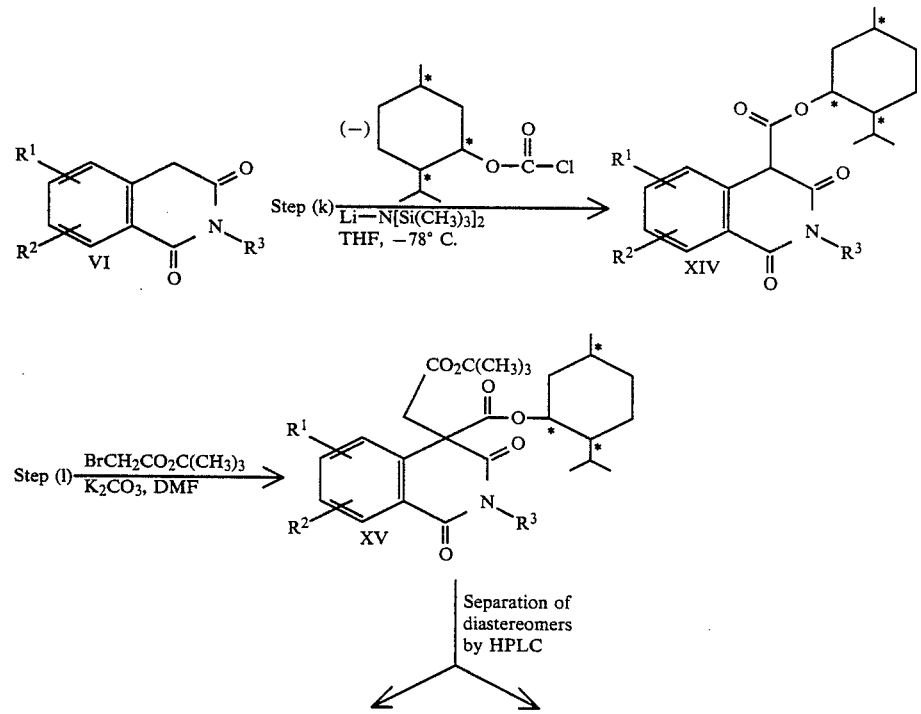

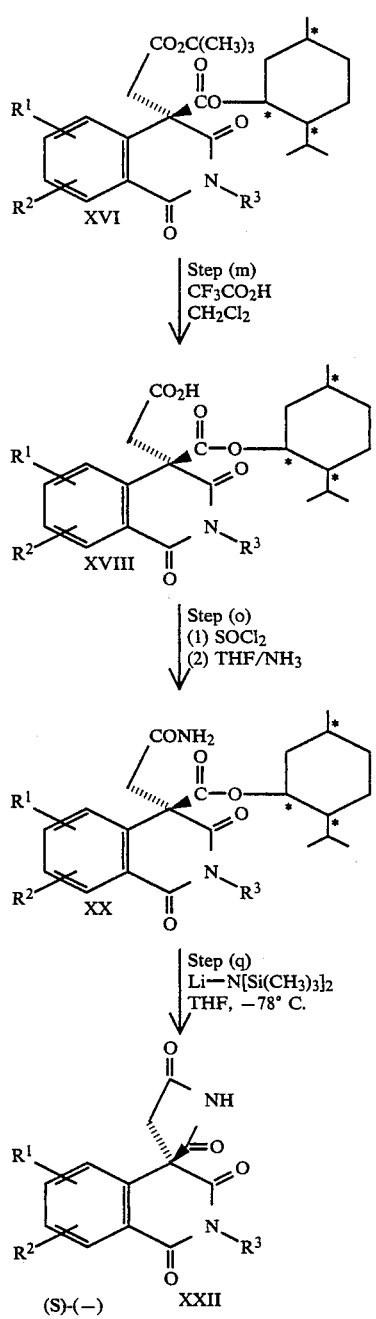
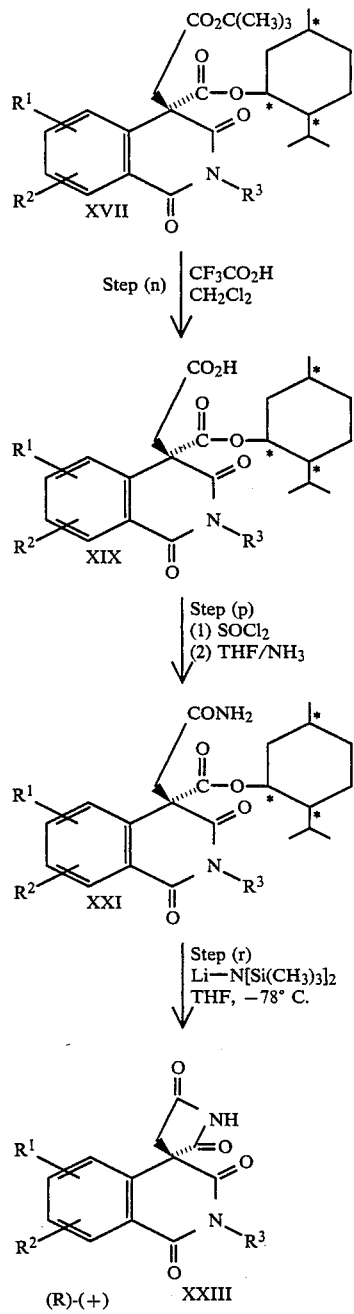

wherein $R^1$ and $R^2$ are hydrogen or halogen; $R^3$ is alkyl containing 1 to 6 carbon atoms, aryl (lower alkyl) or dihalogen-substituted aryl (lower alkyl) wherein aryl contains 6 to 10 carbon atoms and lower alkyl contains 1 to 6 carbon atoms. The process for the production of the compounds of formula (I) wherein $R^1$ and $R^2$ are chlorine or hydrogen; X is methylene; Y and Z are oxygen; M and W are carbonyl; $R^3$ is alkyl (methyl, ethyl, propyl, butyl) or aralkyl (3,4-dichlorobenzyl, or 4-bromo-2-fluorobenzyl) comprises:

Step (k) The compound of formula (VI), wherein $R^1$, $R^2$ and $R^3$ are as defined above is reacted with a base, for example, lithium bis(trimethylsilyl)amide in a conventional solvent which does not adversely influence the reaction, for example, tetrahydrofuran, and subsequent addition of (−)-menthyl chloroformate to produce the compound of formula (XIV), wherein $R^1$, $R^2$ and $R^3$ are as defined above.

Step (l) The compound of formula (XIV), wherein $R^1$, $R^2$ and $R^3$ are as defined above, is reacted with an inorganic base such as potassium carbonate in a conventional solvent which does not adversely influence the reaction, for example, N,N-dimethylformamide, and subsequent addition of the tert-butyl bromoacetate produces the compound of formula (XV), wherein $R^1$, $R^2$ and $R^3$ are as defined above. The compound of formula (XV), wherein $R^1$, $R^2$ and $R^3$ are as defined above, represents a mixture of two diastereomers which are separable by HPLC to produce diastereomer of formula (XVI) and diastereomer of formula (XVII), wherein $R^1$, $R^2$ and $R^3$ are as defined above.

Step (m) The compound of formula (XVI), wherein $R^1$, $R^2$ and $R^3$ are as defined above, is hydrolyzed with an organic acid such as trifluoroacetic acid in a conventional solvent which does not adversely influence the reaction, for example, methylene chloride, to produce the compound of formula (XVIII), wherein $R^1$, $R^2$ and $R^3$ are as defined above.

Step (n) The compound of formula (XVII), wherein $R^1$, $R^2$ and $R^3$ are as defined above, is hydrolyzed with an organic acid such as trifluoroacetic acid in a conventional solvent which does not adversely influence the reaction, for example methylene chloride, to produce the compound of formula (XIX), wherein $R^1$, $R^2$ and $R^3$ are as defined above.

Step (o) The compound of formula (XVIII), wherein $R^1$, $R^2$ and $R^3$ are as defined above, is reacted with thionyl chloride to produce the corresponding acid chloride and subsequent addition to a tetrahydrofuran ammonium solution produces the compound of the formula (XX), wherein $R^1$, $R^2$ and $R^3$ are as defined above.

Step (p) The compound of formula (XIX), wherein $R^1$, $R^2$ and $R^3$ are as defined above, is reacted with thionyl chloride to produce the corresponding acid chloride and subsequent addition to a tetrahydrofuran ammonium solution produces the compound of formula (XXI), wherein $R^1$, $R^2$ and $R^3$ are as defined above.

Step (q) The compound of formula (XX), wherein $R^1$, $R^2$ and $R^3$ are as defined above, is reacted with a base such as lithium bis(trimethylsilyl)amide, in a conventional solvent which does not adversely influence the reaction, for example, tetrahydrofuran, at low temperature ($-78°$ C.) to produce the compound of formula (XXIII), wherein $R^1$, $R^2$ and $R^3$ are as defined above.

Step (r) The compound of formula (XXI), wherein $R^1$, $R^2$ and $R^3$ are as defined above, is reacted with a base such as lithium bis(trimethylsilyl)amide, in a conventional solvent which does not adversely influence the reaction, for example tetrahydrofuran, at low temperature ($-78°$ C.) to produce the compound of formula (XXIII), wherein $R^1$, $R^2$ and $R^3$ are as defined above.

The absolute configuration of the compound of formula (XXII), wherein $R^1$ and $R^2$ are hydrogen and $R^3$ is (4-bromo-2-fluorophenyl)methyl was determined by a single crystal x-ray analysis. It was established that the compound of formula (XXII) possesses the (S) absolute configuration.

Some of the compounds of formula (I) wherein M is carbonyl and W is lower alkylene can be made by the Process C

PROCESS C

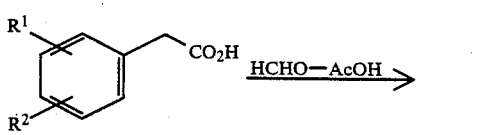

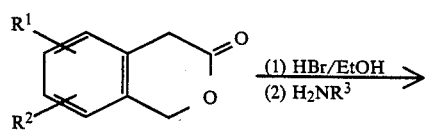

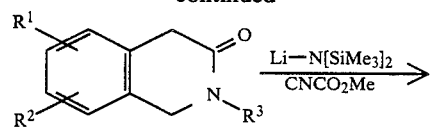

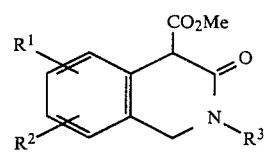

J. Het. Chem., Vol. 4, No. 3,315 (1967).

Other compounds of the present invention of formula (I) wherein M is a carbonyl and W is a sulfonyl can be made by the Process D

PROCESS D

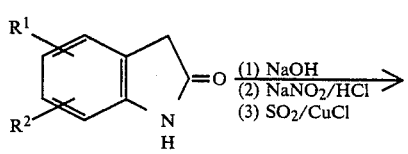

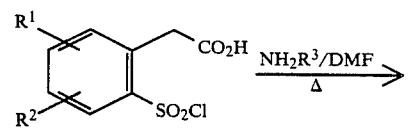

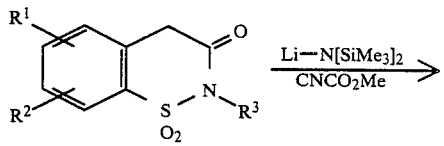

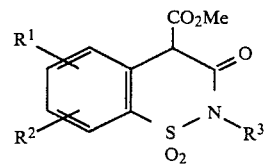

Other compounds of the present invention of formula (I) wherein M is sulfonyl and W is carbonyl can be made by the Process E

PROCESS E

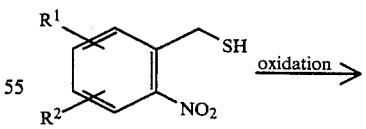

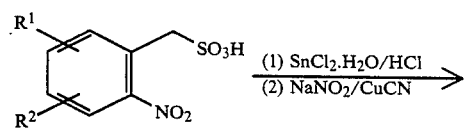

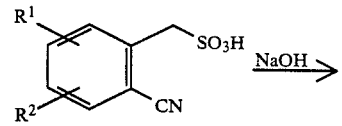

-continued
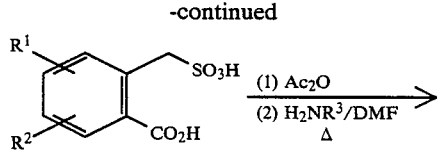
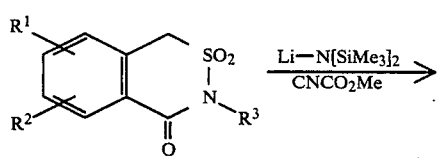
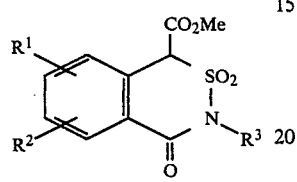
PROCESS G
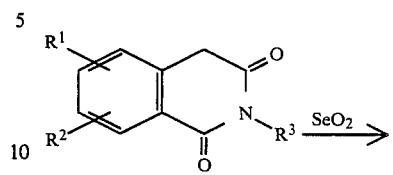
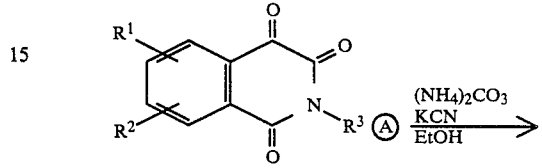
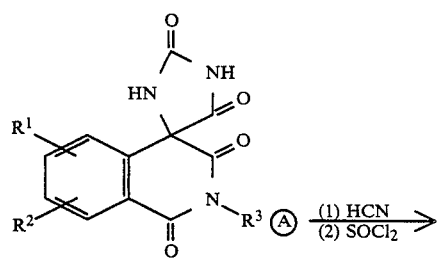
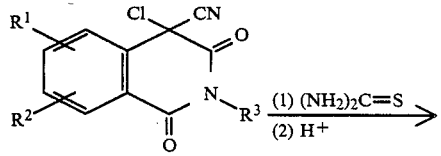
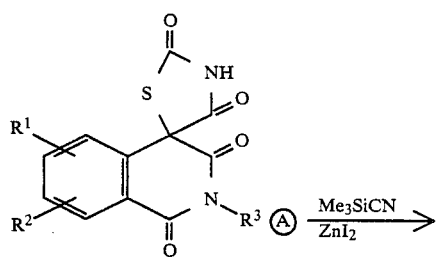
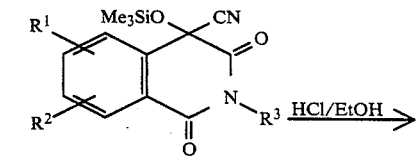
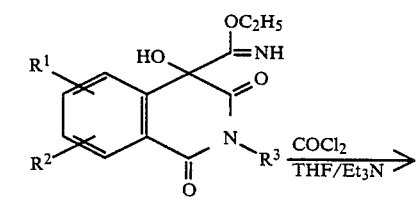
Other compounds of the present invention of formula (I) wherein M is carbonyl and W is thiocarbonyl can be made by the Process F
PROCESS F
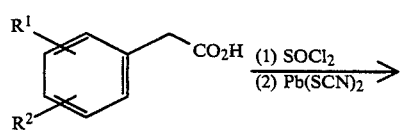
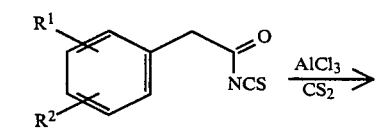
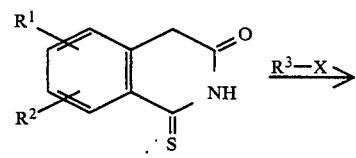
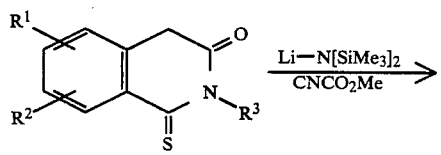
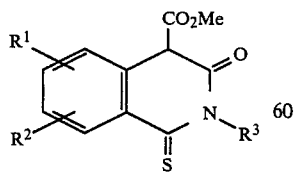
Other compounds of the present invention of formula (I) wherein M and W are carbonyl, Y and Z are oxygen and X is oxygen, sulfur or nitrogen can be made by the Process G

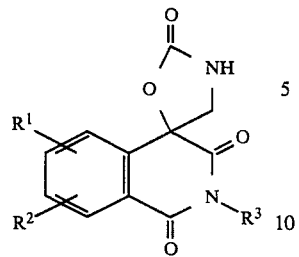

Can. Journal of Chem. 47 858 (1969);
J. Het. Chem. 18, 143 (1981);
Tetrahedron. 36, 943 (1980);
J. Org. Chem. 25, 1920 (1960);
Chem. Pharm. Bull. 30 (10), 3601 (1982);
J. Med. Chem. 29, 770 (1986).

Other compounds of the present invention of formula (I) wherein M and W are lower alkylene can be made by the Process H

PROCESS H

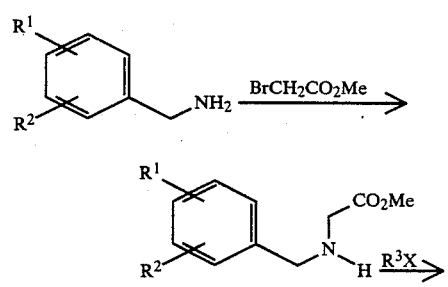

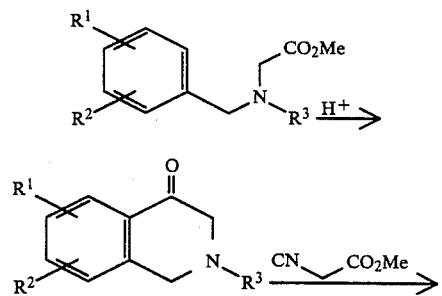

J. Org. Chem. 33, 491 (1968);
J. Org. Chem. 33, 494 (1968); European Pat. No.: 168,181-A.

Other compounds of the present invention of formula (I) wherein M and W are carbonyl and wherein the fused benzene ring is replaced by a thiophene can be made by the Process I

PROCESS I

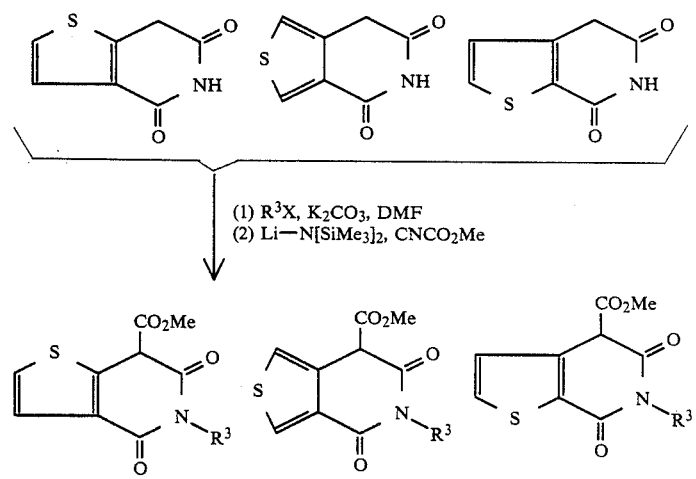

J. Chem. Soc. Perkin I, 1390 (1975);
OPPI BRIEFS 8 (4), 286 (1986).

Other compounds of the present invention of formula (I) wherein M and W are carbonyl and wherein the fused benzene ring is replaced by pyridine can be made by the Process J

PROCESS J

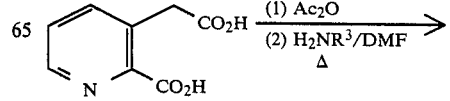

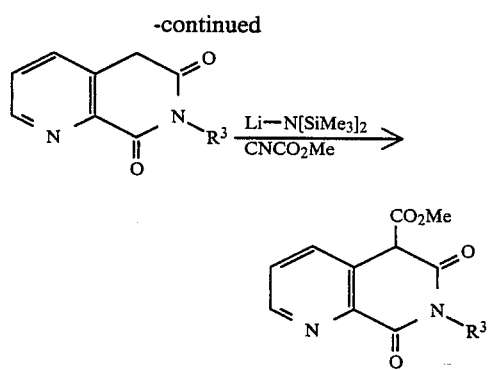

Chem. Abst. 41: 780 g;
U.S. Pat. No. 2,408,020.

Other compounds of the present invention of formula (I) wherein M and W are sulfonyl can be made by the Process K

PROCESS K

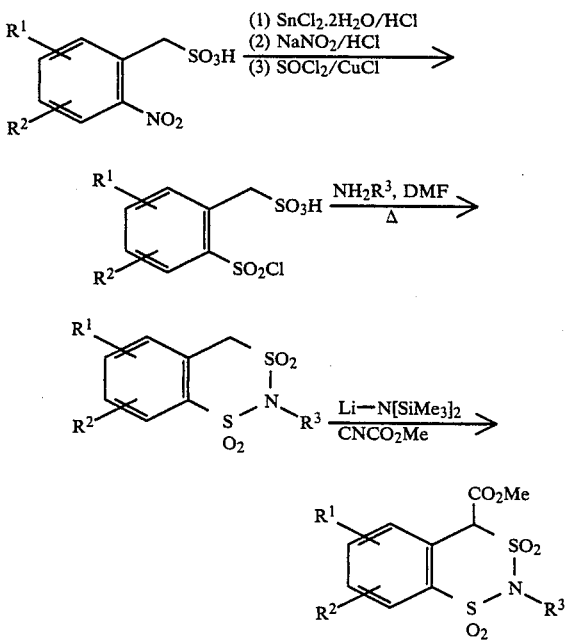

The carbomethoxy intermediate produced by Process C, D, E, F, I, J and K may be converted to compounds of formula (I) by Process A.

The following examples further illustrate this invention:

EXAMPLE 1

2-[(3,4-Dichlorophenyl)methyl]spiro[isoquinoline-4(1H),3'-pyrrolidine]-1,2',3,5'(2H)-tetrone Step (a) Preparation of 2-[(3,4-Dichlorophenyl)methyl]-1,3(2H, 4H)-isoquinolinedione To a mixture of homophthalic anhydride (20.0 g, 123.45 mmol) in DMF (300 mL) was added 3,4-dichlorobenzylamine (25.0 g, 142.04 mmol) and the mixture was stirred at 180° C. for 5 hours. After cooling to room temperature the mixture was poured into $H_2O$, extracted with EtOAc and dried over $MgSO_4$. The crude product was recrystallized from EtOAc/Et$_2$O/-hexane (at 0° C.) to give a brownish solid m.p. 129°–130° C. (25.21 g, 57.5%).

NMR (DMSO-d$_6$, 400 MHz): δ 4.22 (s, 2H, —CH$_2$CO—), 5.0 (s, 2H, —NCH$_2$—), 7.3 (dd, J=8.49 Hz, 1.98 Hz, 1H, Ar—H), 7.4 (d, J=8.54 Hz, 1H, Ar—H), 7.47 (t, J=7.4 Hz, 1H, Ar—H), 7.54 (d, J=8.3 Hz, 1H, Ar—H), 7.57 (d, J=1.78 Hz, 1H, Ar—H), 7.67 (dt, J=8.37 Hz, 0.97 Hz, 1H, Ar—H), 8.03 (d, J=7.83 Hz, 1H, Ar—H).

IR (KBr, cm$^{-1}$): 1650(s), 1330(s), 970(m), 740(m).

MS (m/e): 319(M+), 256(M+—Cl, CO), 118(M+—CONH, —CH$_2$C$_6$H$_3$Cl$_2$).

Anal. Calcd.: C, 60.02; H, 3.46; N, 4.37. Found: C, 59.81; H, 3.60; N, 4.36.

The following compounds were obtained in substantially the same manner as that of Example 1, Step (a).

2-[(4-Bromo-2-fluorophenyl)methyl]-1,3(2H, 4H)-isoquinolinedione

NMR (DMSO-d$_6$, 200 MHz): δ 4.24 (s, 2H, —CH$_2$CON—), 5.04 (s, 2H, —NCH$_2$—), 7.23 (t, J=7.8 Hz, 1H, Ar—H), 7.3 (d, J=7.65 Hz, 1H, Ar—H), 7.4–7.56 (m, 3H, Ar—H), 7.65 (t, J=7.6 Hz, Ar—H), 8.06 (d, J=7.8 Hz, 1H, Ar—H)

IR (KBr, cm$^{-1}$): 1675(s), 1350(m), 975(m).

MS (m/e): 347(M+).

Anal. Calcd.: C, 55.19; H, 3.18; N, 4.02. Found: C, 54.83; H, 3.14; N, 4.07.

M.P. 128°–129° C.

2-[(4-Bromo-2-fluorophenyl)methyl]-6-chloro-1,3(2H, 4H)-isoquinolinedione

NMR (DMSO-d$_6$, 400 MHz): δ 4.23 (s, 2H, —CH$_2$CON—), 5.0 (s, 2H, —NCH$_2$C$_6$H$_3$BrF), 7.19 (t, J=8.20 Hz, 1H, Ar—H), 7.29 (dd, J=8.32 Hz, 1.71 Hz, 1H, Ar—H), 7.5–7.56 (m, 3H, Ar—H), 8.01 (d, J=8.31 Hz, 1H, Ar—H).

IR(KBr, cm$^{-1}$): 3400(m), 1710(m), 1660(s), 1480(m), 740(m).

MS (m/e): (M+).

Anal. Calcd.: C, 50.23; H, 2.63; N, 3.66. Found: C, 50.11; H, 2.60; N, 3.63.

M.P. 157°–159° C.

2-[(4-Bromo-2-fluorophenyl)methyl]-7-chloro-1,3(2H, 4H)-isoquinolinedione

NMR (DMSO-d$_6$, 400 MHz): δ 4.21 (s, 2H, —CH$_2$CON—), 5.01 (s, 2H, —NCH$_2$C$_6$H$_3$BrF), 7.2 (t, J=8.2 Hz, 1H, Ar—H), 7.29 (dd, J=8.35 Hz, 1.85 Hz, 1H, Ar—H), 7.46 (d, J=8.27 Hz, 1H, Ar—H), 7.51 (dd, J=9.9 Hz, 1.8 Hz, 1H, Ar—H), 7.75 (dd, J=8.3 Hz, 2.3 Hz, 1H, Ar—H), 7.97 (d, J=2.3 Hz, 1H, Ar—H).

IR (KBr, cm$^{-1}$): 3420 (m), 1715 (s), 1680 (s), 1645 (s), 1480 (m).

MS (m/e): 381(M+).

Anal. Calcd.: C, 50.23; H, 2.63; N, 3.66. Found: C, 50.11; H, 2.58; N, 3.62.

M.P. 152°–154° C.

2-[(4-Bromo-2-fluorophenyl)methyl]-6-fluoro-1,3(2H,3H)-isoquinolinedione

NMR (DMSO-d$_6$, 400 MHz): δ 4.24 (s, 2H, ArCH$_2$CO—), 5.01 (s, 2H, —NCH$_2$—), 7.19 (t, J=8.24 Hz, 1H, Ar—H), 7.3–7.35 (m, 3H, Ar—H), 7.51 (dd, J=9.87 Hz, 1.87 Hz, 1H, Ar—H), 8.09 (dd, J=8.4 Hz, 5.94 Hz, 1H, Ar—H).

IR (KBr, cm$^{-1}$): 1660 (s), 1340 (s), 760 (m).

MS (m/e): 365 (M+), 337 (M+—CO)

Anal. Calcd.: C, 52.48; H, 2.75; N, 3.83. Found: C, 52.55; H, 2.91; N, 3.73.

M.P. 146°–147° C.

Step (b) Preparation of [(3,4-Dichlorophenyl)methyl]-1,2,3,4-tetrahydro-1,3-dioxo-4-isoquinolinecarboxylic Acid Methyl Ester To a cold (−78° C.) solution of 2-[(3,4-dichlorophenyl)methyl]-1,3(2H, 4H)isoquinolinedione (11.2 g, 35.0 mmol) in anhydrous THF (100 mL) was added lithium bis(trimethylsilyl)amide (42.0 mL, 42 mmol, 1.0M in THF) dropwise over a 10 minute period. After stirring for 3 hours, methyl cyanoformate (3.33 mL, 42.0 mmol) was added and the reaction mixture was allowed to warm up to room temperature. The mixture during that period turned a dark color. It was stirred an additional 30 minutes and quenched with $H_2O$. The dark solution was poured into $H_2O$, acidified with HCl (2N), extracted with EtOAc and dried over $MgSO_4$. The crude product was recrystallized from EtOAc/hexane (at −20° C.) to yield a yellow solid m.p. 164°–166° C. (7.5 g, 56.6%).

NMR (DMSO-$d_6$, 400 MHz): δ [3.67 (s), 3.99 (s), tautomeric, 3H, —$CO_2CH_3$], [5.07 (q), J=15.4 Hz, 5.28 (s), tautomeric, 2H, —N$CH_2$—], [7.27–8.43 (m), tautomeric, 7H, Ar—H].

IR (KBr, cm$^{-1}$): 1680 (s), 1610 (s), 1490 (s), 1355 (s), 1015 (s), 790 (m).

MS (m/e): 377 (M+).

Anal. Calcd.: C, 57.16; H, 3.46; N, 3.70. Found: C, 57.03; H, 3.39; N, 3.68.

The following compounds were obtained in substantially the same manner as that of Example 1, Step (b).

2-[(4-Bromo-2-fluorophenyl)methyl]-1,2,3,4-tetrahydro-1,3-dioxo-4-isoquinoline-carboxylic Acid Methyl Ester NMR (DMSO-$d_6$, 400 MHz): δ [3.67 (s), 3.99 (s), tautomeric, —$CO_2Me$, 3H], [5.06 (q), J=15.4 Hz, 5.29 (s), tautomeric, N$CH_2$, 2H], 7.07–8.44 (m, tautomeric, Ar—H, 7H).

IR (KBr, cm$^{-1}$) 1675 (s), 1610 (s), 1490 (s), 1350 (m), 875 (m).

MS (m/e): 405 (M+), 187[M+-(4-bromo-2-fluorophenyl)methyl].

Anal. Calcd.: C, 53.22; H, 3.23; N, 3.45. Found: C, 53.06; H, 3.11; N, 3.34.

M.P. 149°–150° C.

2-[(4-Bromo-2-fluorophenyl)methyl]-7-chloro-1,2,3,4-tetrahydro-1,3-dioxo-4-isoquinolinecarboxylic Acid Methyl Ester NMR (DMSO-$d_6$, 400 MHz): δ [3.66 (s), 3.98 (s), 3H, tautomeric, —$CO_2CH_3$], [5.06 (q), 5.28 (s), 2H, tautomeric, —$NCH_2C_6H_3BrF$], 7.1–8.4 (6H, tautomeric, Ar—H).

IR (KBr, cm$^{-1}$): 3420 (m), 1670 (s), 1600 (s), 1480 (s), 790 (m).

MS (m/e): 439 (M+).

Anal. Calcd.: C, 49.06; H, 2.74; N, 3.18. Found: C, 48.96; H, 2.80; N, 3.18.

M.P. 161°–162° C.

2-[(4-Bromo-2-fluorophenyl)methyl]-6-chloro-1,2,3,4-tetrahydro-1,3-dioxo-4-isoquinolinecarboxylic Acid Methyl Ester NMR (DMSO-$d_6$, 400 MHz): δ [3.68 (s), 3.98 (s), tautomeric, 3H, —$CO_2CH_3$], [5.0 (q), 5.26 (s), tautomeric, 2H, —$NCH_2C_6H_3BrF$], 7.0–8.4 (m, tautomeric, 6H, Ar—H).

IR (KBr, cm$^{-1}$): 3430 (m), 1670 (s), 1600 (s), 1480 (m), 785 (m).

MS (m/e): 439 (M+).

Anal. Calcd.: C, 49.06; H, 2.74; N, 3.18. Found: C, 49.07; H, 2.79; N, 3.08.

M.P. 181°–182° C.

6-Chloro-1,2,3,4-tetrahydro-2-methyl-1,3-dioxo-4-isoquinolinecarboxylic Acid Methyl Ester NMR (DMSO-$d_6$, 200 MHz): δ [3.23 (s), 3.44 (s), tautomeric, 3H, —$NCH_3$], [3.71 (s), 4.03 (s), tautomeric, 3H, —$CO_2CH_3$], 7.3–8.4 (tautomeric, Ar—H, 3H).

IR (KBr, cm$^{-1}$): 3440 (m), 1680 (s), 1600 (s), 1440 (m), 1320 (s), 790 (m).

MS (m/e): 267 (M+), 235 (M+-OMe).

Anal. Calcd.: C, 53.85; H, 3.77; N, 5.23. Found: C, 53.66; H, 3.63; N, 5.14.

M.P. 166°–167° C.

7-Chloro-1,2,3,4-tetrahydro-2-methyl-1,3-dioxo-4-isoquinolinecarboxylic Acid Methyl Ester NMR (DMSO-$d_6$, 200 MHz): δ [3.22 (s), 3.45 (s), tautomeric, 3H, N—$CH_3$], [3.7 (s), 4.02 (s), tautomeric, 3H, —$CO_2CH_3$], 7.5–8.4 (tautomeric, Ar—H, 3H).

IR (KBr, cm$^{-1}$): 3440 (m), 1770 (s), 1600 (s), 1330 (s), 830 (s), 795 (m).

MS (m/e): 267 (M+), 235 (M+-OMe-H).

Anal. Calcd. for ($C_{12}H_{10}ClNO_4 \times \frac{1}{3} H_2O$): C, 52.65; H, 3.90; N, 5.12. Found: C, 52.64; H, 3.68; N, 5.18.

M.P. 158°–159° C.

1,2,3,4-Tetrahydro-2-methyl-1,3-dioxo-4-isoquinolinecarboxylic Acid Methyl Ester NMR (DMSO-$d_6$, 200 MHz): δ [3.24 (s), 3.46 (s), tautomeric, 3H, —$NCH_3$], [3.7 (s), 4.03 (s), tautomeric, 3H, —$CO_2CH_3$], 7.4–8.45 (tautomeric, 4H, Ar—H).

IR (KBr, cm$^{-1}$): 3400 (brm), 1670 (s), 1600 (s), 1420 (m), 780 (m).

MS (m/e): 233 (M+), 118 (M+—$CO_2Me$, —$CONCH_3$).

Anal. Calcd.: C, 61.80; H, 4.75; N, 6.01. Found: C, 61.62; H, 4.89; N, 5.92.

M.P. 130°–131° C.

Step (c) Preparation of 2-[(3,4-Dichlorophenyl)methyl]-1,2,3,4-tetrahydro-4-(methoxycarbonyl)-1,3-dioxo-4-isoquinolineacetic Acid 1,1-Dimethylethyl Ester To a suspension of [(3,4-dichlorophenyl)methyl]-1,2,3,4-tetrahydro-1,3-dioxo-4-isoquinolinecarboxylic acid methyl ester (6.3 g, 16.66 mmol), $K_2CO_3$ (3.45 g, 24.99 mmol) in DMF (100 mL) was added tert-butyl bromoacetate (4.03 mL, 24.99 mmol). After stirring at 70° C. for 1 hour, the mixture was poured into $H_2O$, extracted with EtOAc and dried over $MgSO_4$. The crude product was purified by flash chromatography (hexane/EtOAc 4:1) to yield a yellowish oil (5.9 g, 71.9%).

NMR (DMSO-$d_6$, 400 MHz): δ 1.02 (s, 9H, $CO_2$—tert butyl), 3.56 (s, 3H, —$CO_2CH_3$), 3.62 (q, J=17.2 Hz, 2H, —$CH_2CO_2$—tertbutyl), 5.14 (s, 2H, —$NCH_2$—), 7.32 (dd, J=8.42 Hz, 2.04 Hz, 1H, Ar—H), 7.52 (d, J=2.03 Hz, 1H, Ar—H), 7.59–7.62 (m, 3H, Ar—H), 7.78 (dt, J=7.64 Hz, 1.39 Hz, 1H, Ar—H), 8.19 (dd, J=8.51 Hz, 1.66 Hz, 1H, Ar—H).

IR (CHCl$_3$, cm$^{-1}$): 1750 (s), 1720 (s), 1675 (s), 1355 (m), 1140 (s), 740 (m).

MS (m/e): 491 (M+), 304 (M+—CONH, —CH$_2$C$_6$H$_3$Cl$_2$).

The following compounds were obtained in substantially the same manner as that of Example 1, Step c).

2-[(4-Bromo-2-fluorophenyl)methyl]-1,2,3,4-tetrahydro-4-(methoxycarbonyl)-1,3-dioxo-4-isoquinolineacetic Acid 1,1-Dimethylethyl Ester NMR (DMSO-D$_6$, 400 MHz): δ 1.04 [s, 9H, —C(CH$_3$)$_3$], 3.53 (s, 3H, —CO$_2$CH$_3$), 3.60 [dd, J=17.7 Hz, 2H, —CH$_2$CO$_2$C(CH$_3$)$_3$], 5.14 (s, 2H, NCH$_2$—), 7.17 (t, J=8.25 Hz, 1H, Ar—H), 7.36 (dd, J=8.36 Hz, 1.75 Hz, 1H, Ar—H), 7.6 (m, 3H, Ar—H), 7.77 (dt, J=7.2 Hz, 1.27 Hz, 1H, Ar—H), 8.19 (dd, J=8.25 Hz, 1.54 Hz, 1H, Ar—H).

IR (CHCl$_3$, cm$^{-1}$): 1720 (s), 1675 (s), 1360 (s), 765 (m).

MS (m/e): 520 (M+H)+, 464 [M+-C(CH$_3$)$_3$].

1,2,3,4-Tetrahydro-4-(methoxycarbonyl)-2-methyl-1,3-dioxo-4-isoquinolineacetic Acid 1,1-Dimethylethyl Ester NMR (DMSO-d$_6$, 200 MHz): δ 1.01 (s, 9H, —CO$_2$— tertbutyl), 3.31 (s, 3H, N—CH$_3$), 3.58 (m, 5H, —CO$_2$CH$_3$, —CH$_2$CO$_2$—tertbutyl), 7.61 (m, 2H), 7.74 (dt, J=7.6 Hz, 1.6 Hz, 1H, Ar—H), 8.18 (dd, J=8.4 Hz, 2.0 Hz, 1H, Ar—H).

IR (KBr, cm$^{-1}$): 3420 (m), 1750 (s), 1730 (s), 1670 (s), 1465 (m), 740 (m).

MS (m/e): 347 (M+).

Anal. Calcd.: C, 62.24; H, 6.09; N, 4.03. Found: C, 62.20; H, 6.08; N, 4.02.

M.P. 89°-90° C.

6-Chloro-1,2,3,4-tetrahydro-4-(methoxycarbonyl)-2-methyl-1,3-dioxo-4-isoquinolineacetic Acid 1,1-Dimethylethyl Ester NMR (DMSO-d$_6$, 200 MHz): δ 1.06 (s, 9H, —CO$_2$— tertbutyl), 3.3 (s, 3H, —NCH$_3$), 3.6 (s, 3H, —CO$_2$CH$_3$), 3.67 (q, J=17.5 Hz, 2H, —CH$_2$CO$_2$—tertbutyl), 7.68 (dd, J=9.0 Hz, 1.6 Hz, 1H, Ar—H), 7.77 (d, J=2.0 Hz, 1H, Ar—H), 8.21 (d, J=8.2 Hz, 1H, Ar—H).

IR (KBr, cm$^{-1}$): 3440 (m), 1740 (s), 1720 (s), 1680 (s), 1360 (s), 1060 (s), 770 (m).

MS (m/e): 381 (M+).

Anal. Calcd.: C, 56.82; H, 5.28; N, 3.67. Found: C, 57.00; H, 5.41; N, 3.66.

M.P. 135°-136° C.

7-Chloro-1,2,3,4-tetrahydro-4-(methoxycarbonyl)-2-methyl-1,3-dioxo-4-isoquinolineacetic Acid 1,1-Dimethylethyl Ester NMR (DMSO-d$_6$, 200 MHz): δ 1.06 (s, 9H, CO$_2$—tert butyl), 3.31 (s, 3H, —NCH$_3$), 3.59 (s, 5H, —CO$_2$CH$_3$, —CH$_2$CO$_2$—tertbutyl), 7.65 (d, J=8.4 Hz, 1H, Ar—H), 7.84 (d, J=8.2 Hz, 2.8 Hz, 1H, Ar—H), 8.15 (d, J=2.2 Hz, 1H, Ar—H).

IR (KBr, cm$^{-1}$): 3440 (m), 1760 (s), 1740 (m), 1725 (m), 1680 (s), 1440 (m), 770 (m).

MS (m/e): 381 (M+), 308 (M+-O-tertbutyl).

Anal. Calcd.: C, 56.62; H, 5.28; N, 3.67. Found: C, 56.44; H, 5.23; N, 3.72.

M.P. 103°-104° C.

2-Ethyl-1,2,3,4-tetrahydro-4-(methoxycarbonyl)-1,3-dioxo-4-isoquinolineacetic Acid 1,1-Dimethylethyl Ester NMR (DMSO-d$_6$, 200 MHz): δ 1.04 (s, 9H, CO$_2$—tert butyl), 1.14 (t, J=7.0 Hz, 3H, —NCH$_2$CH$_3$), 3.58 (s, 2H, —CH$_2$CO—), 4.0 (q, J=7.0 Hz, 2H, —NCH$_2$CH3), 7.59-7.61 (m, 2H, Ar—H), 7.75 (t, J=7.8 Hz, 1H, Ar—H), 8.18 (d, J=7.9 Hz, 1H, Ar—H).

IR (KBr, cm$^{-1}$): 1730 (s), 1670 (s), 1465 (m), 1160 (s), 710 (m).

MS (m/e): 361 (M+), 305 (M+—C$_4$H$_8$), 288 (M+—O—tertbutyl), 246 (M+—CH$_2$CO$_2$—tertbutyl).

6-Bromo-1,2,3,4-tetrahydro-4-(methoxycarbonyl)-2-methyl-1,3-dioxo-4-isoquinolineacetic Acid 1,1-Dimethylethyl Ester NMR (DMSO-d$_6$, 200 MHz): δ 1.05 [s, 9H, —C(CH$_3$)$_3$], 3.28 (s, 3H, —NCH$_3$), 3.59 (s, 3H, —CO$_2$CH$_3$), 3.58 (d, J=17.03 Hz, 1H, —CH$_2$CO$_2$—), 3.67 (d, J=17.03 Hz, 1H, —CH$_2$CO$_2$—), 7.81 (dd, J=8.4 Hz, 1.85 Hz, 1H, Ar—H), 7.88 (d, J=1.81 Hz, 1H, Ar—H), 8.08 (d, J=8.4 Hz, 1H, Ar—H).

IR (KBr, cm$^{-1}$): 1740 (s), 1710 (s), 1670 (s), 755 (m).

MS (m/e): 425 (M+), 370 (M+—C$_4$H$_7$), 352 (M+—C$_4$H$_9$O).

Anal. Calcd.: C, 50.72; H, 4.73; N, 3.29. Found: C, 50.47; H, 4.68; N, 3.12.

M.P. 152°-153° C.

Step (d) Preparation of 2-[(3,4-Dichlorophenyl)methyl]-1,2,3,4-tetrahydro-4-(methoxycarbonyl)-1,3-dioxo-4-isoquinolineacetic Acid A mixture of 2-[(3,4-dichlorophenyl)methyl]-1,2,3,4-tetrahydro-4-(methoxycarbonyl)-1,3-dioxo-4-isoquinolineacetic acid 1,1-dimethylethyl ester (5.8 g, 11.78 mmol), CH$_2$Cl$_2$ (50 mL) and CF$_3$CO$_2$H (10 mL) was stirred at room temperature for 10 hours. The volatiles were removed in vacuo, and the residue was recrystallized from acetone/ether/hexane (at −20° C.) to yield a white solid m.p. 153°-154° C. (4.0 g, 89.5%).

NMR (DMSO-d$_6$, 400 MHz): δ 3.56 (s, 3H, —CO$_2$CH$_3$), 3.65 (q, J=17.7 Hz, 2H, —CH$_2$ CO$_2$H), 5.12 (q, J=15.4 Hz, 2H, —NCH$_2$—), 7.27 (dd, J=8.35 Hz, 1.97 Hz, 1H, Ar—H), 7.52 (d, J=1.92 Hz, 1H, Ar—H), 7.58-7.62 (m, 3H), 7.76 (dt, J=7.35 Hz, 0.87 Hz, 1H, Ar—H), 8.16 (dd, J=7.82 Hz, 1.16 Hz, 1H, Ar—H).

IR (KBr, cm$^{-1}$): 3430 (m), 3500-2500 (br), 1755 (s), 1710 (s), 1670 (s), 1350 (m), 1230 (s), 745 (m).

MS (m/e): 435 (M+).

Anal. Calcd.: C, 55.07; H, 3.47; N, 3.21. Found: C, 55.15; H, 3.84; N, 2.94.

The following compounds were obtained in substantially the same manner as that of Example 1, Step (d).

2-[(4-Bromo-2-fluorophenyl)methyl]-1,2,3,4-tetrahydro-4-(methoxycarbonyl)-1,3-dioxo-4-isoquinolineacetic Acid NMR (DMSO-d$_6$, 400 MHz): δ 3.54 (s, 3H, —CO$_2$CH$_3$), 3.64 (q, J=17.67 Hz, 2H, —CH$_2$ CO$_2$H), 5.12 (q, J=15.34 Hz, 2H, —NCH$_2$—), 7.14 (t, J=8.22 Hz, 1H, Ar—H), 7.3 (d, J=8.3 Hz, 1H, Ar—H), 7.5-7.6 (m, 3H, Ar—H), 7.76 (d, 7.4 Hz, 1H, Ar—H), 8.16 (d, J=7.8 Hz, 1H, Ar—H), 12.35 (s, 1H, —CO$_2$H).

IR (KBr, cm$^{-1}$): 3280 (m), 3500-2500 (br), 1750 (s), 1720 (s), 1675 (s), 1350 (s), 875 (m).

MS (m/e): 463 (M+), 445 (M+—H,—OH).

Anal. Calcd. for $C_{20}H_{15}BrFNO_6 \cdot 0.2H_2O$: C, 51.28; H, 3.30; N, 2.99. Found: C, 51.26; H, 3.48; N, 2.95.
M.P. 139°–140° C.

2-[(4-Bromo-2-fluorophenyl)methyl]-7-chloro-1,2,3,4-tetrahydro-4-(methoxycarbonyl)-1,3-dioxo-4-isoquinolineacetic Acid NMR (DMSO-$d_6$, 200 MHz): δ 3.67 (s, 3H, —CO$_2$CH$_3$), 3.71 (q, J=17.5 Hz, 2H, —CH$_2$CO$_2$H), 5.14 (q, J=17.2 Hz, 2H, —NCH$_2$C$_6$H$_3$BrF), 7.15 (t, J=8.4 Hz, 1H, Ar—H), 7.36 (dd, J=8.2 Hz, 2.0 Hz, 1H, Ar—H), 7.55 (dd, J=9.8 Hz, 2.0 Hz, 1H, Ar—H), 7.70 (d, J=8.4 Hz, 1H, Ar—H), 7.87 (dd, J=8.8 Hz, 2.8 Hz, 1H, Ar—H), 8.14 (d, J=2.2 Hz, 1H, Ar—H), 12.8 (brs, 1H, —CO$_2$H).
IR (KBr, cm$^{-1}$): 3500–2500 (brs), 1730 (s), 1710 (s), 1665 (s), 1420 (m), 750 (m).
Anal. Calcd.: C, 48.17; H, 2.83; N, 2.81. Found: C, 47.96; H, 2.85; N, 2.85.
M.P. 86°–88° C.

2-[(4-Bromo-2-fluorophenyl)methyl]-6-chloro-1,2,3,4-tetrahydro-4-(methoxycarbonyl)-1,3-dioxo-4-isoquinolineacetic Acid NMR (DMSO-$d_6$, 200 MHz): δ 3.58 (s, 3H, —CO$_2$CH$_3$), 3.68 (d, J=17.5 Hz, 1H, —CH$_2$CO$_2$H), 3.85 (d, J=17.5 Hz, 1H, —CH$_2$CO$_2$H), 5.15 (s, 2H, —NCH$_2$—), 7.15 (t, J=8.3 Hz, 1H, Ar—H), 7.35 (d, J=8.3 Hz, 1H, Ar—H), 7.55 (d, J=9.6 Hz, 1H, Ar—H), 7.68 (d, J=8.2 Hz, 1H, Ar—H), 7.85 (s, 1H, Ar—H), 8.2 (d, J=8.1 Hz, 1H, Ar—H).
MS (m/e): 497 (M+).
Anal. Calcd.: C, 48.17; H, 2.83; N, 2.81. Found: C, 47.85; H, 2.85; N, 2.86.

2-[(4-Bromo-2-fluorophenyl)methyl]-6-fluoro-1,2,3,4-tetrahydro-4-(methoxycarbonyl)-1,3-dioxo-4-isoquinolineacetic Acid NMR (DMSO-$d_6$, 400 MHz): δ 3.56 (s, 3H, —CO$_2$CH$_3$), 3.6 (d, J=17.9 Hz, 1H, —CH$_2$CO$_2$H), 3.8 (d, J=17.9 Hz, 1H, —CH$_2$CO$_2$H), 5.1 (dd, J=15.5 Hz, 2H, —NCH$_2$—), 7.12 (t, J=8.23 Hz, 1H, Ar—H), 7.31 (dd, J=8.28 Hz, 1.68 Hz, 1H, Ar—H), 7.45 (dt, J=8.56 Hz, 2.5 Hz, 1H, Ar—H), 7.54 (dd, J=9.77 Hz, 1.89 Hz, 1H, Ar—H), 7.64 (dd, J=9.61 Hz, 2.46 Hz, 1H, Ar—H), 8.23 (dd, J=8.79 Hz, 5.81 Hz, 1H, Ar—H), 12.67 (brs, 1H, —CO$_2$H).
IR (KBr, cm$^{-1}$): 3400–2700 (br), 1745 (s), 1710 (s), 1670 (s), 770 (m).
MS (m/e): 481 (M+), 405 (M+—CO$_2$—CH$_3$OH).
Anal. Calcd.: C, 49.81; H, 2.93; N, 2.90. Found: C, 49.94; H, 3.03; N, 2.84.
M.P. 132°–133.5° C.

1,2,3,4-Tetrahydro-4-(methoxycarbonyl)-2-methyl-1,3-dioxo-4-isoquinolineacetic Acid NMR (DMSO-$d_6$, 200 MHz): δ 3.28 (s, 3H, N—CH$_3$), 3.57 (s, 3H, —CO$_2$CH$_3$), 3.61 (s, 2H, —CH$_2$CO$_2$H), 7.54 (m, 2H, Ar—H), 7.75 (dt, J=8.2 Hz, 1H, Ar—H), 8.18 (d, J=7.8 Hz, 1H, Ar—H), 12.3 (brs, 1H, —CO$_2$H).
IR (KBr, cm$^{-1}$): 3420 (m), 3500–2500 (brs), 1755 (s), 1730 (s), 1710 (s), 1660 (s), 1455 (m), 745 (m).
MS (m/e): 291 (M+).
Anal. Calcd.: C, 57.73; H, 4.50; N, 4.81. Found: C, 57.55; H, 4.68; N, 4.75.
M.P. 188°–189° C.

7-Chloro-1,2,3,4-tetrahydro-4-(methoxycarbonyl)-2-methyl-1,3-dioxo-4-isoquinolineacetic Acid NMR (DMSO-$d_6$, 200 MHz): δ 3.29 (s, 3H, —NCH$_3$), 3.59 (s, 3H, —CO$_2$CH$_3$), 3.63 (s, 2H, —CH$_2$CO$_2$H), 7.68 (d, J=9.0 Hz, 1H, Ar—H), 7.81 (dd, J=8.8 Hz, 2.0 Hz, 1H, Ar—H), 8.12 (d, J=1.8 Hz, 1H, Ar—H).
IR (KBr, cm$^{-1}$): 3430 (m), 3500–2500 (brm), 1755 (s), 1720 (s), 1675 (s), 1440 (m), 1240 (s), 770 (m).
MS (m/e): 325 (M+).
Anal. Calcd.: C, 51.63; H, 3.71; N, 4.30. Found: C, 51.41; H, 3.66; N, 4.26.
M.P. 161°–162° C.

6-Chloro-1,2,3,4-tetrahydro-4-(methoxycarbonyl)-2-methyl-1,3-dioxo-4-isoquinolineacetic Acid NMR (DMSO-$d_6$, 200 MHz): δ 3.27 (s, 3H, —NCH$_3$), 3.59 (s, 3H, —CO$_2$CH$_3$), 3.64 (q, J=17.5 Hz, 2H, —CH$_2$CO$_2$H), 7.65 (dd, J=8.6 Hz, 2.0 Hz, 1H, Ar—H), 7.78 (d, J=2.0 Hz, 1H, Ar—H), 8.18 (d, J=8.0 Hz, 1H, Ar—H).
IR (KBr, cm$^{-1}$): 3440 (m), 3500–2500 (brm), 1750 (s), 1710 (s), 1675 (s), 1430 (m), 1240 (s), 770 (m).
MS (m/e): 325 (M+).
Anal. Calcd.: C, 51.63; H, 3.71; N, 4.30. Found: C, 51.73; H, 3.70; N, 4.28.
M.P. 195°–196° C.

2-Ethyl-1,2,3,4-tetrahydro-4-(methoxycarbonyl)-1,3-dioxo-4-isoquinolineacetic Acid NMR (DMSO-$d_6$, 400 MHz): δ 1.09 (t, J=7.04 Hz, 3H, —NCH$_2$CH$_3$), 3.55 (s, 3H, —CO$_2$CH$_3$), 3.94 (q, J=7.0 Hz, 2H, —NCH$_2$CH$_3$), 7.54–7.58 (m, 2H, Ar—H), 7.72 (dt, J=7.6 Hz, 1.48 Hz, 1H, Ar—H), 8.14 (dd, J=7.91 Hz, 1.14 Hz, 1H, Ar—H), 12.6 (brs, 1H, —CO$_2$H).
IR (KBr, cm$^{-1}$): 3450 (m), 3500–2500 (brm), 1750 (s), 1710 (s), 1665 (s), 1640 (s), 1465 (m), 745 (m).
MS (m/e): 305 (M+), 246 (M+—CO$_2$Me).
Anal. Calcd.: C, 59.01; H, 4.95; N, 4.59. Found: C, 58.87; H, 5.05; N, 4.60.
M.P. 145°–146° C.

1,2,3,4-Tetrahydro-4-(methoxycarbonyl)-2-propyl-1,3-dioxo-4-isoquinolineacetic Acid NMR (DMSO-$d_6$, 200 MHz): δ 0.87 (t, J=7.0 Hz, 3H, —NCH$_2$CH$_2$CH$_3$), 1.54–1.62 (m, 2H, —NCH$_2$CH$_2$CH$_3$), 3.56 (s, 3H, —CO$_2$CH$_3$), 3.62 (s, 2H, —CH$_2$CO$_2$H), 3.91 (t, J=7.0 Hz, 2H, —NCH$_2$CH$_2$CH$_3$), 7.5–7.62 (m, 2H, Ar—H), 7.81 (t, J=7.8 Hz, 1H, Ar—H), 8.15 (d, J=7.65 Hz, 1H, Ar—H).
IR (KBr, cm$^{-1}$): 3500–2500 (brs), 1750 (s), 1710 (s), 1665 (s), 1430 (m), 750 (m).
MS (m/e): 319 (M+), 260 (M+—CH$_2$CO$_2$H).
Anal. Calcd.: C, 60.18; H, 5.37; N, 4.39. Found: C, 59.96; H, 5.28; N, 4.34.
M.P. 119°–120° C.

2-Butyl-1,2,3,4-tetrahydro-4-(methoxycarbonyl)-1,3-dioxo-4-isoquinolineacetic Acid NMR (DMSO-$d_6$, 200 MHz): δ 0.89 (t, J=7.6 Hz, 3H, —NCH$_2$CH$_2$CH$_2$CH$_3$), 1.21–1.38 (m, 2H, —N,CH$_2$CH$_2$CH$_2$CH$_3$), 1.4–1.6 (m, 1H, —NCH$_2$CH$_2$CH$_2$CH$_3$), 3.56 (s, 3H, —CO$_2$CH$_3$), 3.62 (s, 2H, —CH$_2$CO$_2$H), 3.94 (t, J=7.0 Hz, 2H, —NCH$_2$CH$_2$CH$_2$CH$_3$), 7.61 (m, 2H, Ar—H), 7.74 (dt, J=8.0 Hz, 1.4 Hz, 1H, Ar—H), 8.18 (dd, J=8.0 Hz, 1.6 Hz, 1H, Ar—H).

IR (KBr, cm$^{-1}$): 3500–2500 (brs), 1750 (s), 1710 (s), 1640 (s), 1420 (m), 745 (m).

MS (m/e): 333 (M$^+$), 274 (M$^+$—CH$_2$CO$_2$H).

Anal. Calcd.: C, 61.25; H, 5.75; N, 4.20. Found: C, 61.09; H, 5.67; N, 4.23.

M.P. 133°–134° C.

6-Bromo-1,2,3,4-tetrahydro-4-(methoxycarbonyl)-2-methyl-1,3-dioxo-4-isoquinolineacetic Acid NMR (DMSO-d$_6$, 200 MHz): δ 3.26 (s, 3H, N—CH$_3$), 3.53 (d, J=17.2 Hz, 1H, —CH$_2$CO$_2$H), 3.58 (s, 3H, —CO$_2$CH$_3$), 3.74 (d, J=17.2 Hz, 1H, —CH$_2$CO$_2$H), 7.77 (dd, J=8.2 Hz, 2.2 Hz, 1H, Ar—H), 7.87 (d, J=2.2 Hz, 1H, Ar—H), 8.0 (d, J=8.2 Hz, 1H, Ar—H), 12.64 (s, 1H, —CO$_2$H).

IR (KBr, cm$^{-1}$): 3450–2600 (br), 1735 (s), 1700 (s), 1660 (s).

MS (m/e): 369 (M$^+$), 324 (M$^+$—CO$_2$H).

Anal. Calcd.: C, 45.43; H, 3.27; N, 3.78. Found: C, 45.04; H, 3.16; N, 3.62.

M.P. 194°–195° C.

Step (e) Preparation of 4-(2-Amino-2-oxoethyl)-2-[(3,4-dichlorophenyl)methyl]-1,2,3,4-tetrahydro-1,3-dioxo-4-isoquinolinecarboxylic Acid Methyl Ester To a solution of 2-[(3,4-dichlorophenyl)methyl]-1,2,3,4-tetrahydro-4-(methoxycarbonyl)-1,3-dioxo-4-isoquinolineacetic acid (3.6 g, 8.26 mmol) in DMF (50 mL) were added 1-(3-dimethylaminopropyl)-3-ethylcarbodiimide hydrochloride (2.06 g, 10.74 mmol), and 1-hydroxybenzotriazole hydrate (1.67 g, 12.38 mmol) and the mixture was stirred for 2 hours. A freshly prepared tetrahydrofuran ammonium solution was added dropwise with continuous monitoring of the reaction by thin layer chromatography (TLC). After the reaction was completed the mixture was poured into H$_2$O, acidified with HCl (2N), extracted with EtOAc and dried over MgSO$_4$. The crude product was recrystallized from ether/hexane (at 0° C.) to yield a white solid, m.p. 193°–194° C. (3.4 g, 94.7%).

NMR (DMSO-d$_6$, 400 MHz): δ 3.55 (s, 3H, —CO$_2$CH$_3$), 3.56 (q, J=16.54 Hz, 2H, —CH$_2$CONH$_2$), 5.1 (q, J=15.37 Hz, 2H, —NCH$_2$—), 6.87 (s, 1H, —CONH$_2$), 7.33 (dd, J=8.37 Hz, 1.87 Hz, 1H, Ar—H), 7.46 (d, J=7.84 Hz, 1H, Ar—H), 7.52 (s, 1H, —CONH$_2$), 7.57–7.60 (m, 3H, Ar—H), 7.77 (dt, J=7.65 Hz, 1.1 Hz, 1H, Ar—H), 8.11 (dd, J=7.6 Hz, 1.74 Hz, 1H, Ar—H).

IR (KBr, cm$^{-1}$): 3450 (s), 3340 (m), 1750 (s), 1720 (s), 1670 (s), 1360 (s), 740 (m).

MS (m/e): 435 (M+H)$^+$, 377 (M$^+$—CH$_2$CONH$_2$).

Anal. Calcd.: C, 55.19; H, 2.71; N, 6.44. Found: C, 55.17; H, 3.69; N, 6.62.

The following compounds were obtained in substantially the same manner as that of Example 1, Step (e).

4-(2-Amino-2-oxoethyl)-2-[(4-bromo-2-fluorophenyl)methyl]-1,2,3,4-tetrahydro-1,3-dioxo-4-isoquinolinecarboxylic Acid Methyl Ester NMR (DMSO-d$_6$, 400 MHz): δ 3.53 (s, 3H, —CO$_2$CH$_3$), 3.51 (q, J=16.6 Hz, 2H, —CH$_2$CONH$_2$), 5.1 (q, J=15.4 Hz, 2H, —NCH$_2$—), 6.88 (s, 1H, —CONH$_2$), 7.23 (t, J=8.0 Hz, 1H, Ar—H), 7.3 (dd, J=8.3 Hz, 1.84 Hz, 1H, Ar—H), 7.46 (d, J=7.98 Hz, 1H, Ar—H), 7.52 (s, 1H, —CONH$_2$), 7.54–7.60 (m, 2H, Ar—H), 7.75 (dt, J=7.76 Hz, 1.39 Hz, 1H, Ar—H), 8.1 (dd, J=7.87 Hz, 1.22 Hz, 1H, Ar—H).

IR (KBr, cm$^{-1}$): 3450 (s), 1730 (s), 1720 (s), 1670 (s), 1350 (s), 875 (m).

MS (m/e): 463 (M+H)$^+$, 446 (M$^+$—OH).

Anal. Calcd.: C, 52.08; H, 3.06; N, 6.07. Found: C, 51.91; H, 3.36; N, 6.09.

M.P. 180°–181° C.

4-(2-Amino-2-oxoethyl)-2-[(4-bromo-2-fluorophenyl)methyl]-7-chloro-1,2,3,4-tetrahydro-1,3-dioxo-4-isoquinolinecarboxylic Acid Methyl Ester NMR (DMSO-d$_6$, 200 MHz): δ 3.56 (s, 5H, —CO$_2$CH$_3$, CH$_2$CONH$_2$), 5.12 (q, J=17.2 Hz, 2H, —NCH$_2$C$_6$H$_3$BrF), 6.95 (s, 1H, —CONH$_2$), 7.2–7.35 (m, 2H, Ar—H), 7.5–7.6 (m, 2H, Ar—H), 7.84 (dd, J=8.6 Hz, 1.8 Hz, 1H, Ar—H), 8.1 (d, J=2.2 Hz, 1H, Ar—H).

IR (KBr, cm$^{-1}$): 3450 (m), 3370 (m), 1755 (m), 1720 (m), 1675 (s), 1430 (m), 765 (m).

MS (m/e): 497 (M+H)$^+$.

Anal. Calcd.: C, 48.27; H, 3.04; N, 5.63. Found: C, 48.27; H, 3.12; N, 5.46.

M.P. 94°–96° C.

4-(2-Amino-2-oxoethyl)-2-[(4-bromo-2-fluorophenyl)methyl]-6-chloro-1,2,3,4-tetrahydro-1,3-dioxo-4-isoquinolinecarboxylic Acid Methyl Ester NMR (DMSO-d$_6$, 200 MHz): δ 3.62 (m, 5H, —CO$_2$CH$_3$, —CH$_2$CONH$_2$), 5.11 (q, J=17.6 Hz, 2H, —NCH$_2$C$_6$H$_3$BrF), 6.95 (brs, 1H, —CONH$_2$), 7.20–7.35 (m, 2H, Ar—H), 7.5–7.7 (m, 4H, Ar—H, —CONH$_2$), 8.12 (d, J=7.8 Hz, 1H, Ar—H).

IR (KBr, cm$^{-1}$): 3450 (m), 1725 (m), 1675 (s), 1490 (m).

MS (m/e): 497 (M+H)$^+$.

Anal. Calcd.: C, 48.26; H, 3.04; N, 5.63. Found: C, 48.53; H, 3.22; N, 5.53.

4-(2-Amino-2-oxoethyl)-2-[(4-bromo-2-fluorophenyl)methyl]-6-fluoro-1,2,3,4-tetrahydro-1,3-dioxo-4-isoquinolinecarboxylic Acid Methyl Ester NMR (DMSO-d$_6$, 400 MHz): δ 3.49 (d, J=16.65 Hz, 1H, —CH$_2$CONH$_2$), 3.56 (s, 3H, —CO$_2$CH$_3$), 3.59 (d, J=16.65 Hz, 1H, —CH$_2$CONH$_2$), 5.08 (dd, J=15.48 Hz, 2H, —NCH$_2$—), 6.94 (s, 1H, —CONH$_2$), 7.21 (t, J=8.22 Hz, 1H, Ar—H), 7.30 (dd, J=8.27 Hz, 1.64 Hz, 1H, Ar—H), 7.38–7.46 (m, 2H, Ar—H), 7.51 (s, 1H, —CONH$_2$), 7.54 (dd, J=9.81 Hz, 1.83 Hz, 1H, Ar—H), 8.20 (dd, J=8.74 Hz, 5.84 Hz, 1H, Ar—H).

IR (KBr, cm$^{-1}$): 3440 (s), 3350 (s), 1740 (s), 1710 (s), 1670 (s), 1660 (s), 765 (m).

MS (m/e): 480 (M$^+$), 463 (M$^+$—NH$_3$).

Anal. Calcd.: C, 49.91; H, 3.14; N, 5.82. Found: C, 49.56; H, 3.09; N, 5.73.

M.P. 203°–204.5° C.

4-(2-Amino-2-oxoethyl)-1,2,3,4-tetrahydro-2-methyl-1,3-dioxo-4-isoquinolinecarboxylic Acid Methyl Ester NMR (DMSO-d$_6$, 200 MHz): δ 3.27 (s, 3H, —NCH$_3$), 3.49 (s, 2H, —CH$_2$CO$_2$H), 3.56 (s, 3H, —CO$_2$CH$_3$), 6.78 (s, 1H, —CONH$_2$), 7.4–7.6 (m, 3H, Ar—H, —CONH$_2$), 7.69 (dt, J=7.6 Hz, 2 Hz, 1H, Ar—H), 8.16 (d, J=8.2 Hz, 1H, Ar—H).

IR (KBr, cm$^{-1}$): 3420 (m), 3320 (m), 1760 (s), 1660 (s), 1420 (m), 755 (m).

MS (m/e): 290 (M$^+$).

Anal. Calcd.: C, 57.93; H, 4.86; N, 9.65. Found: C, 57.73; H, 4.95; N, 9.56.

M.P. 230°–231° C.

4-(2-Amino-2-oxoethyl)-7-chloro-1,2,3,4-tetrahydro-2-methyl-1,3-dioxo-4-isoquinolinecarboxylic Acid Methyl Ester NMR (DMSO-$d_6$, 200 MHz): δ 3.27 (s, 3H, —NC$\underline{H_3}$), 3.48 (s, 2H, —C$\underline{H_2}$CONH$_2$), 3.58 (s, 3H, —CO$_2$C$\underline{H_3}$), 6.85 (s, 1H, —CO$\underline{NH_2}$), 7.45 (d, J=8.6 Hz, 1H, Ar—$\underline{H}$), 7.49 (s, 1H, —CON$\underline{H_2}$), 7.80 (dd, J=8.2 Hz, 2.2 Hz, 1H, Ar—$\underline{H}$), 8.08 (d, J=2.2 Hz, 1H, Ar—$\underline{H}$).

IR (KBr, cm$^{-1}$): 3420 (m), 1760 (s), 1715 (m), 1665 (s), 1440 (m), 770 (m).

MS (m/e): 324 (M+).

Anal. Calcd.: C, 51.78; H, 4.03; N, 8.63. Found: C, 51.82; H, 3.98; N, 8.54.

M.P. 215°–216° C.

4-(2-Amino-2-oxoethyl)-6-chloro-1,2,3,4-tetrahydro-2-methyl-1,3-dioxo-4-isoquinolinecarboxylic Acid Methyl Ester NMR (DMSO-$d_6$, 200 MHz): δ 3.26 (s, 3H, —NC$\underline{H_3}$), 3.51 (q, J=17.5 Hz, 2H, —C$\underline{H_2}$CONH$_2$), 3.59 (s, 3H, —CO$_2$C$\underline{H_3}$), 6.85 (s, 1H, —CON$\underline{H_2}$), 7.5 (s, 1H, —CON$\underline{H_2}$), 7.53 (d, J=2.0 Hz, 1H, Ar—$\underline{H}$), 7.62 (dd, J=8.6 Hz, 2.0 Hz, 1H, Ar—$\underline{H}$), 8.16 (d, J=8.0 Hz, 1H, Ar—$\underline{H}$).

IR (KBr, cm$^{-1}$): 3420 (s), 1760 (s), 1710 (m), 1660 (s), 1235 (m), 770 (m).

MS (m/e): 324 (M+).

Anal. Calcd.: C, 51.78; H, 4.03; N, 8.63. Found: C, 51.67; H, 3.95; N, 8.42.

M.P. 221°–222° C.

4-(2-Amino-2-oxoethyl)-2-ethyl-1,2,3,4-tetrahydro-1,3-dioxo-4-isoquinolinecarboxylic Acid Methyl Ester NMR (DMSO-$d_6$, 400 MHz): δ 1.09 (t, J=6.94 Hz, 3H, —NCH$_2$C$\underline{H_3}$), 3.46 (q, J=16.57 Hz, 2H, —C$\underline{H_2}$CONH$_2$), 3.54 (s, 3H, —CO$_2$C$\underline{H_3}$), 3.94 (q, J=6.73 Hz, 2H, —NC$\underline{H_2}$CH$_3$), 6.76 (brs, 1H, —CON$\underline{H_2}$), 7.38 (d, J=7.8 Hz, 1H, Ar—$\underline{H}$), 7.44 (brs, 1H, —CON$\underline{H_2}$), 7.53 (t, J=7.56 Hz, 1H, Ar—$\underline{H}$), 7.7 (dt, J=7.86 Hz, 1.28 Hz, 1H, Ar—$\underline{H}$), 8.11 (d, J=7.82 Hz, 1H, Ar—$\underline{H}$).

IR (KBr, cm$^{-1}$): 3450 (s), 1750 (s), 1710 (s), 1680 (s), 1650 (s), 1420 (m), 780 (m).

MS (m/e): 304 (M+), 246 (M+—CH$_2$CONH$_2$), 245 (M+—CO$_2$CH$_3$).

Anal. Calcd.: C, 59.21; H, 5.3; N, 9.21. Found: C, 59.17; H, 5.46; N, 9.23.

M.P. 190°–191° C.

4-(2-Amino-2-oxoethyl)-1,2,3,4-tetrahydro-2-propyl-1,3-dioxo-4-isoquinolinecarboxylic Acid Methyl Ester NMR (DMSO-$d_6$, 200 MHz): δ 0.87 (t, J=7.0 Hz, 3H, —NCH$_2$CH$_2$C$\underline{H_3}$), 1.51–1.62 (m, 2H, —NCH$_2$C$\underline{H_2}$CH$_3$), 3.49 (s, 2H, —C$\underline{H_2}$CONH$_2$), 3.55 (s, 3H, —CO$_2$C$\underline{H_3}$), 3.89 (t, J=7.0 Hz, 2H, —NC$\underline{H_2}$CH$_2$CH$_3$), 6.78 (s, 1H, —CONH$_2$), 7.43 (d, J=7.2 Hz, 1H, Ar—$\underline{H}$), 7.46 (s, 1H, —CON$\underline{H_2}$), 7.58 (dd, J=7.6 Hz, 1.6 Hz, 1H, Ar—$\underline{H}$), 7.7 (dt, J=7.6 Hz, 2.0 Hz, 1H, Ar—$\underline{H}$), 8.15 (dd, J=8.2 Hz, 1.8 Hz, 1H, Ar—$\underline{H}$).

IR (KBr, cm$^{-1}$): 3420 (s), 3200 (s), 1765 (s), 1710 (s), 1670 (s), 1430 (m), 750 (m).

MS (m/e): 318 (M+), 260 (M+—CH$_2$CONH$_2$), 259 (M+—CO$_2$CH$_3$).

Anal. Calcd.: C, 60.37; H, 5.70; N, 8.80. Found: C, 60.24; H, 5.60; N, 8.72.

M.P. 181°–182° C.

4-(2-Amino-2-oxoethyl)-2-butyl-1,2,3,4-tetrahydro-1,3-dioxo-4-isoquinolinecarboxylic Acid Methyl Ester NMR (DMSO-$d_6$, 200 MHz): δ 0.89 (t, J=7.6 Hz, 3H, —NCH$_2$CH$_2$CH$_2$C$\underline{H_3}$), 1.2–1.4 (m, 2H, —NCH$_2$CH$_2$C$\underline{H_2}$CH$_3$), 1.4–1.62 (m, 2H, —NCH$_2$C$\underline{H_2}$CH$_2$CH$_3$), 3.49 (s, 2H, —C$\underline{H_2}$CONH$_2$), 3.55 (s, 3H, —CO$_2$C$\underline{H_3}$), 3.92 (t, J=7.6 Hz, 2H, —NC$\underline{H_2}$CH$_2$CH$_2$CH$_3$), 6.79 (s, 1H, —CONH$_2$), 7.43 (d, J=8.0 Hz, 1H, Ar—$\underline{H}$), 7.46 (s, 1H, —CON$\underline{H_2}$), 7.58 (dt, J=7.6 Hz, 1.2 Hz, 1H, Ar—$\underline{H}$), 8.15 (dd, J=8.0 Hz, 1.0 Hz, 1H, Ar—$\underline{H}$).

IR (KBr, cm$^{-1}$): 3400 (s), 3200 (s), 1750 (s), 1710 (s), 1660 (s), 1410 (m), 750 (m).

MS (m/e): 332 (M+), 274 (M+—CH$_2$CONH$_2$), 273 (M+—CO$_2$CH$_3$).

Anal. Calcd.: C, 61.44; H, 6.07; N, 8.43. Found: C, 61.23; H, 5.99; N, 8.33.

M.P. 142°–143° C.

4-(2-Amino-2-oxoethyl)-6-bromo-1,2,3,4-tetrahydro-1,3-dioxo-4-isoquinolinecarboxylic Acid Methyl Ester NMR (DMSO-$d_6$, 400 MHz): δ 3.24 (s, 3H, N—C$\underline{H_3}$), 3.44 (dd, J=6.54 Hz, 2H, —C$\underline{H_2}$CONH$_2$), 3.58 (s, 3H, —CO$_2$C$\underline{H_3}$), 6.84 (s, 1H, —CON$\underline{H}$—), 7.48 (s, 1H, —CON$\underline{H}$—), 7.64 (d, J=1.76 Hz, 1H, Ar—$\underline{H}$), 7.76 (dd, J=8.4 Hz, 1.83 Hz, 1H, Ar—$\underline{H}$), 8.03 (d, J=8.42 Hz, 1H, Ar—$\underline{H}$).

IR (KBr, cm$^{-1}$): 3420 (s), 1740 (s), 1715 (s), 1665 (s).

Anal. Calcd.: C, 45.54; H, 3.55; N, 7.59. Found: C, 45.26; H, 3.34; N, 7.46.

M.P. 212°–213° C.

Step (f) Preparation of 2-[(3,4-Dichlorophenyl)methyl]spiro[isoquinoline-4(1H)3′-pyrrolidine]-1,2′,3,5′(2H)-tetrone To a solution of 4-(2-amino-2-oxoethyl)-2-[(3,4-dichlorophenyl)methyl]-1,2,3,4-tetrahydro-1,3-dioxo-isoquinolinecarboxylic acid methyl ester (2.5 g, 5.75 mmol) in DMF (20 mL) was added NaH (80% dispersion in oil, 172.4 mg, 5.75 mmol) portionwise, over a 10 minute period. After stirring for 30 minutes, the mixture was poured into H$_2$O, acidified with HCl (2N), extracted with EtOAc and dried over MgSO$_4$. The crude product was purified by flash chromatography on acid washed silica gel (5% H$_3$PO$_4$ in MeOH) to yield a white solid, m.p. 118°–120° C. (1.82 g, 78.8%).

NMR (DMSO-$d_6$, 400 MHz): δ 3.5 (q, J=18.34 Hz, 2H, —C$\underline{H_2}$CONH—), 5.06 (q, J=15.26 Hz, 2H, —NC$\underline{H_2}$—), 7.27 (dd, J=8.33 Hz, 2.0 Hz, 1H, Ar—$\underline{H}$), 7.52 (d, J=1.93 Hz, 1H, Ar—$\underline{H}$), 7.57 (d, J=8.3 Hz, 1H, Ar—$\underline{H}$), 7.61 (t, J=7.6 Hz, 1H, Ar—$\underline{H}$), 7.68 (d, J=7.72 Hz, 1H, Ar—$\underline{H}$), 7.79 (dt, J=7.76 Hz, 1.2 Hz, 1H, Ar—$\underline{H}$), 8.17 (dd, J=7.8 Hz, 0.9 Hz, 1H, Ar—$\underline{H}$), 12.02 (s, 1H, —CONHCO—).

IR (KBr, cm$^{-1}$): 3250 (s), 1730 (s), 1670 (s), 1340 (s), 970 (m), 760 (m).

MS (m/e): 403 (M+H)+.

Anal. Calcd. for C$_{19}$H$_{12}$Cl$_2$N$_2$O$_4$×⅓H$_2$O: C, 55.74; H, 3.09; N, 6.84. Found: C, 55.94; H, 3.04; N, 6.61.

The following compounds were obtained in substantially the same manner as that of Example 1, Step (f).

2-[(4-Bromo-2-fluorophenyl)methyl]spiro[isoquinoline-4(1H),3′-pyrrolidine]-1,2′,3,5′(2H)-tetrone NMR (DMSO-$d_6$, 400 MHz): δ 3.47 (q, J=18.24 Hz, 2H, —C$\underline{H_2}$CONH—), 5.06 (s, 2H, —NC$\underline{H_2}$—), 7.14 (t, J=8.2 Hz, 1H, Ar—$\underline{H}$), 7.33 (dd, J=8.28 Hz, 1.71 Hz, 1H, Ar—$\underline{H}$), 7.55 (dd, J=9.9 Hz, 1.8 Hz, 1H, Ar—$\underline{H}$), 7.62 (t, J=7.6 Hz, 1H, Ar—H), 7.68 (d, J=7.78 Hz, 1H, Ar—H), 7.78 (dt, J=8.85 Hz, 1.12 Hz, 1H, Ar—H), 8.15 (dd, J=7.86 Hz, 1.3 Hz, 1H, Ar—H), 12.01 (s, 1H, —CONHCO—).

IR (KBr, cm$^{-1}$): 3450 (m), 3250 (m), 1730 (s), 1680 (s), 1490 (m), 1345 (m), 1180 (m), 875 (m).

MS (m/e): 430 (M+), 387 (M+—CONH), 200 (M+—CONH, —CH$_2$C$_6$H$_3$BrF).

Anal. Calcd.: C, 52.92; H, 2.80; H, 6.50. Found: C, 52.61; H, 2.70; N, 6.46.

M.P. 112°–114° C.

[2-[(4-Bromo-2-fluorophenyl)methyl]-7-chloro]-spiro[isoquinoline-4(1H),3'-pyrrolidine]-1,2',3,5'(2H)-tetrone NMR (DMSO-d$_6$, 400 MHz): δ 3.41 (q, J=18.29 Hz, 2H, —CH$_2$CONH—), 5.05 (s, 2H, —NCH$_2$C$_6$H$_3$BrF), 7.15 (t, J=8.2 Hz, 1H, Ar—H), 7.32 (dd, J=8.3 Hz, 1.76 Hz, 1H, Ar—H), 7.52 (dd, J=9.78 Hz, 1.94 Hz, 1H, Ar—H), 7.76 (d, J=8.5 Hz, 1H, Ar—H), 7.85 (dd, J=8.55 Hz, 2.43 Hz, 1H, Ar—H), 8.11 (d, J=2.3 Hz, 1H, Ar—H), 12.04 (s, 1H, —CONHCO—).

IR (KBr, cm$^{-1}$): 3450 (m), 3620 (s), 1720 (s), 1670 (s), 1430 (m), 775 (m).

MS (m/e): 465 (M+H)+.

Anal. Calcd.: C, 49.01; H, 2.38; N, 6.02. Found: C, 48.88; H, 2.37; N, 5.92.

M.P. 187°–188° C.

[2-[(4-Bromo-2-fluorophenyl)methyl]-6-chloro]-spiro[isoquinoline-4(1H),3'-pyrrolidine]-1,2',3,5'(2H)-tetrone NMR (DMSO-d$_6$, 200 MHz): δ 3.46 (q, J=18.3 Hz, 2H, —CH$_2$CONH—), 5.06 (s, 2H, —NCH$_2$C$_6$H$_3$BrF), 7.14 (t, J=8.0 Hz, 1H, Ar—H), 7.36 (d, J=8.8 Hz, 1H, Ar—H), 7.57 (dd, J=8.4 Hz, 1.8 Hz, 1H, Ar—H), 7.68 (dd, J=8.6 Hz, 1.2 Hz, 1H, Ar—H), 7.98 (s, 1H, Ar—H), 8.18 (d, J=8.4 Hz, 1H, Ar—H), 12.0 (s, 1H, —CONHCO).

IR (KBr, cm$^{-1}$): 3310 (s), 1745 (s), 1715 (m), 1675 (s), 1430 (m), 780 (m).

MS (m/e): 465 (M+H)+.

Anal. Calcd.: C, 49.01; H, 2.38; N, 6.02. Found: C, 48.93; H, 2.37; N, 5.97.

M.P. 196°–197° C.

[2-[(4-Bromo-2-fluorophenyl)methyl]-5-fluoro]-spiro[isoquinoline-4(1H),3'-pyrrolidine]-1,2',3,5'(2H)-tetrone NMR (DMSO-d$_6$, 400 MHz): δ 3.20 (dd, J=18.56 Hz, 1.97 Hz, 1H, —CH$_2$CONH—), 3.33 (dd, J=18.56 Hz, 2.74 Hz, 1H, —CH$_2$CONH—), 5.05 (s, J=15.3 Hz, 2H, —NCH$_2$—), 7.16 (t, J=8.27 Hz, 1H, Ar—H), 7.34 (dd, J=8.32 Hz, 1.72 Hz, 1H, Ar—H), 7.54 (dd, J=9.85 Hz, 1.88 Hz, 1H, Ar—H), 7.67–7.75 (m, 2H, Ar—H), 8.03 (m, 1H, Ar—H), 12.2 (s, 1H, —CONHCO—).

IR (KBr, cm$^{-1}$): 3325 (s), 1730 (s), 1700 (s), 1670 (s), 760 (m).

MS (m/e): 448 (M+).

Anal. Calcd.: C, 50.80; H, 2.47; N, 6.24. Found: C, 50.61; H, 2.46; N, 6.28.

M.P. 202.5°–203.5° C.

[2-[(4-Bromo-2-fluorophenyl)methyl]-6-fluoro]-spiro[isoquinoline-4(1H),3'-pyrrolidine]-1,2',3,5'(2H)-tetrone NMR (DMSO-d$_6$, 400 MHz): δ 3.44 (s, 2H, —CH$_2$CONH—), 5.05 (s, 2H, —NCH$_2$—), 7.14 (t, J=8.42 Hz, 1H, Ar—H), 7.32 (dd, J=7.58 Hz, 1.26 Hz, 1H, Ar—H), 7.48 (dt, J=8.64 Hz, 2.1 Hz, 1H, Ar—H), 7.53 (dd, 9.89 Hz, 1.89 Hz, 1H, Ar—H), 7.75 (dd, 9.69 Hz, 2.32 Hz, 1H, Ar—H), 8.22 (dd, J=8.84 Hz, 5.89 Hz, 1H, Ar—H), 12.0 (s, 1H, —CONHCO—).

IR (KBr, cm$^{-1}$): 3400 (m), 3260 (s), 1735 (s), 1680 (s).

MS (m/e): 448 (M+), 405 (M+—CONH).

Anal. Calcd.: C, 50.80; H, 2.47; N, 6.24. Found: C, 50.73; H, 2.52; N, 6.16.

M.P. 231°–232° C.

[2-[(4-Bromo-2-fluorophenyl)methyl]-7-fluoro]-spiro[isoquinoline-4(1H),3'-pyrrolidine]-1,2',3,5'(2H)-tetrone NMR (DMSO-d$_6$, 400 MHz): δ 3.42 (dd, J=18.3 Hz, 2H, —CH$_2$CONH—), 5.06 (s, 2H, NCH$_2$—), 7.15 (t, J=8.21 Hz, 1H, Ar—H), 7.32 (dd, J=8.21 Hz, J=1.9 Hz, 1H, Ar—H), 7.53 (dd, J=9.9 Hz, 1.9 Hz, 1H, Ar—H), 7.67 (dt, J=8.42 Hz, 2.74 Hz, 1H, Ar—H), 7.81 (dd, J=8.64 Hz, 4.84 Hz, 1H, Ar—H), 7.89 (dd, J=8.84 Hz, 2.73 Hz, 1H, Ar—H), 12.01 (s, 1H, —CONHCO—).

IR (KBr, cm$^{-1}$): 3400 (m), 3270 (s), 1725 (s), 1680 (s).

MS (m/e): 449 (M+H)+.

Anal. Calcd.: C, 50.80; H, 2.47; N, 6.24. Found: C, 50.52; H, 2.53; N, 6.06.

M.P. 189°–190° C.

[2-[(4-Bromo-2-fluorophenyl)methyl]-8-fluoro]-spiro[isoquinoline-4(1H),3'-pyrrolidine]-1,2',3,5'(2H)-tetrone NMR (DMSO-d$_6$, 400 MHz): δ 3.5 (dd, J=18.32 Hz, 2H, —CH$_2$CONH—), 5.03 (dd, J=15.34 Hz, 2H, —NCH$_2$—), 7.17 (t, J=8.21 Hz, 1H, Ar—H), 7.33 (dd, J=8.21 Hz, 1.47 Hz, 1H, Ar—H), 7.43 (d, J=8.42 Hz, 1H, Ar—H), 7.46 (d, J=8.42 Hz, 1H, Ar—H), 7.52–7.56 (m, 2H, Ar—H), 7.79 (m, 1H, Ar—H), 12.04 (s, 1H, —CONHCO—).

IR (KBr, cm$^{-1}$): 3460 (m), 3380 (s), 1740 (s), 1690 (s).

MS (m/e): 449 (M+H)+.

Anal. Calcd.: C, 50.80; H, 2.47; N, 6.24. Found: C, 50.44; H, 2.81; N, 5.87.

[2-[(4-Bromo-2-fluorophenyl)methyl]-7-methoxy]-spiro[isoquinoline-4(1H),3'-pyrrolidine]-1,2',3,5'(2H)-tetrone NMR (DMSO-d$_6$, 400 MHz): δ 3.31 (dd, J=18.43 Hz, 2H, —CH$_2$CONH—), 3.85 (s, 3H, —OCH$_3$), 5.06 (s, 2H, —NCH$_2$—), 7.13 (t, J=8.3 Hz, 1H, Ar—H), 7.31–7.36 (m, 2H, Ar—H), 7.52 (dd, J=9.8 Hz, 1.9 Hz, 1H, Ar—H), 7.6–7.61 (m, 2H, Ar—H), 11.95 (s, 1H, —CONHCO—).

IR (KBr, cm$^{-1}$): 3250 (s), 1735 (s), 1680 (s).

MS (m/e): 461 (M+H)+.

Anal. Calcd.: C, 52.08; H, 3.06; N, 6.07. Found: C, 51.91; H, 3.23; N, 5.86.

M.P. 160°–161° C.

[6-Bromo-2-[(4-bromo-2-fluorophenyl)methyl]-7-methoxy]spiro[isoquinoline-4(1H),3'-pyrrolidine]-1,2',3,5'(2H)-tetrone NMR (DMSO-d$_6$, 400 MHz): δ 3.38 (dd, J=18.11 Hz, 2H, —CH$_2$CONH—), 3.96 (s, 3H, —OCH$_3$), 5.05 (s, 2H, —NCH$_2$—), 7.12 (t, J=8.24 Hz, 1H, Ar—H), 7.32 (dd, J=8.08 Hz, 1.65 Hz, 1H, Ar—H), 7.52 (dd, J=9.8 Hz, 1.95 Hz, 1H, Ar—H), 7.68 (s, 1H, Ar—H), 8.09 (s, 1H, Ar—H), 11.93 (s, 1H, —CONHCO—).

IR (KBr, cm$^{-1}$): 3400 (m), 3360 (s), 1730 (s), 1680 (s).

MS (m/e): 538 (M+H)$^+$, 495 (M$^+$+H—CONH), 467 (M$^+$+H—CONHCO).

Anal. Calcd.: C, 44.56; H, 2.24; N, 5.20. Found: C, 44.26; H, 2.82; N, 4.97.

M.P. 134°–136° C.

2-Methylspiro[isoquinoline-4(1H),3'-pyrrolidine]-1,2',3,5'(2H)-tetrone

NMR (DMSO-d$_6$, 400 MHz): δ 3.24 (s, 3H, —N—CH$_3$), 3.43 (q, J=18.38 Hz, 2H, —CH$_2$CONH—), 7.58–7.64 (m, 2H, Ar—H), 7.74 (dt, J=7.64 Hz, 1.2 Hz, 1H, Ar—H), 8.15 (dd, J=7.72 Hz, 0.94 Hz, 1H, Ar—H), 12.0 (2, 1H, —CONHCO—).

IR (KBr, cm$^{-1}$): 3340 (s), 1720 (s), 1660 (s), 1310 (s), 765 (m).

MS (m/e): 258 (M+).

Anal. Calcd.: C, 60.47; H, 3.90; N, 10.85. Found: C, 60.27; H, 4.03; N, 10.82.

M.P. 224°–225° C.

2-Ethylspiro[isoquinoline-4(1H),3'-pyrrolidine]-1,2',3,5'(2H)-tetrone

NMR (DMSO-d$_6$, 400 MHz): δ 1.09 (t, J=7.0 Hz, 3H, —NCH$_2$CH$_3$), 3.45 (q, J=18.35 Hz, 2H, —CH$_2$CONH—), 4.9 (q, J=6.9 Hz, 2H, —NCH$_2$CH$_3$), 7.58–7.64 (m, 2H, Ar—H), 7.75 (dt, J=7.45 Hz, 1.46 Hz, 1H, Ar—H), 8.16 (dd, J=7.88 Hz, 1.19 Hz, 1H, Ar—H), 11.98 (s, 1H, —CONHCO—).

IR (KBr, cm$^{-1}$): 3300 (s), 1730 (s), 1710 (s), 1670 (s), 1465 (m), 760 (m).

MS (m/e): 273 (M+H)$^+$.

Anal. Calcd.: C, 61.76; H, 4.44; N, 10.29. Found: C, 61.45; H, 4.44; N, 10.22.

M.P. 183°–185° C.

2-Propylspiro[isoquinoline-4(1H),3'-pyrrolidine]-1,2',3,5'(2H)-tetrone

NMR (DMSO-d$_6$, 400 MHz): δ 0.84 (t, J=7.4 Hz, 3H, —NCH$_2$CH$_2$CH$_3$), 1.51–1.61 (m, 2H, —NCH$_2$CH$_2$CH$_3$), 3.35 (q, J=18.3 Hz, 2H, —CH$_2$CONH—), 3.85 (t, J=7.2 Hz, 2H, —NCH$_2$CH$_2$CH$_3$), 7.58–7.65 (m, 2H, Ar—H), 7.73 (dt, J=7.64 Hz, 0.97 Hz, 1H, Ar—H), 8.16 (d, J=7.84 Hz, 1H, Ar—H), 11.98 (s, 1H, —CONHCO).

IR (KBr, cm$^{-1}$): 3320 (s), 1730 (s), 1710 (s), 1460 (m), 755 (m).

MS (m/e): 287 (M+H)$^+$, 257 (M$^+$—CH$_2$CH$_3$), 243 (M$^+$—CH$_2$CH$_2$—CH$_3$).

Anal. Calcd.: C, 62.93; H, 4.93; N, 9.78. Found: C, 62.79; H, 5.06; N, 9.77.

M.P. 190°–192° C.

2-Butylspiro[isoquinoline-4(1H),3'-pyrrolidine]-1,2',3,5'(2H)-tetrone

NMR (DMSO-d$_6$, 400 MHz): δ 0.87 (t, J=7.27 Hz, 3H, —NCH$_2$CH$_2$CH$_2$CH$_3$), 1.21–1.31 (m, 2H, —NCH$_2$CH$_2$CH$_2$CH$_3$), 1.42–1.52 (m, 2H, —NCH$_2$CH$_2$CH$_2$CH$_3$), 3.44 (q, J=18.26 Hz, 2H, —CH$_2$CONH—), 3.87 (t, J=7.3 Hz, 2H, —NCH$_2$CH$_2$CH$_2$CH$_3$), 7.58–7.64 (m, 2H, Ar—H), 7.75 (dt, J=7.86 Hz, 1.4 Hz, 1H, Ar—H), 8.15 (dd, J=7.82 Hz, 1.27 Hz, 1H, Ar—H), 11.97 (s, 1H, —CONHCO).

IR (KBr, cm$^{-1}$): 3250 (s), 1730 (s), 1670 (s), 1465 (m), 760 (m).

MS (m/e): 301 (M+H)$^+$, 271 (M$^+$—CH$_2$CH$_3$), 257 (M$^+$—CH$_2$CH$_2$CH$_3$).

Anal. Calcd.: C, 63.99; H, 5.37; N, 9.33. Found: C, 63.87; H, 5.31; N, 9.25.

M.P. 143°–144° C.

EXAMPLE 2

2-Methyl-1,3(2H, 4H)-isoquinolinedione

Anhydrous monomethylamine was passed through a solution of homophthalic anhydride (10.0 g, 61.73 mmol) in anhydrous THF (200 mL) for 10 minutes. The formed suspension was stirred for 1 hour and the volatiles were removed in vacuo. The residue was taken in DMF (200 mL) and the suspension was stirred at 180° C. for 10 hours. After cooling, the brownish solution was poured into H$_2$O, extracted with EtOAc and dried over MgSO$_4$. The crude product was recrystallized from acetone/ether/hexane (at 0° C.) to yield a yellow solid, m.p. 120°–121° C. (7.9 g, 73.1%).

NMR (DMSO-d$_6$, 400 MHz): δ 3.18 (s, 3H, —NCH$_3$), 4.12 (s, 2H, —CH$_2$CONCH$_3$), 7.36 (d, J=7.67 Hz, 1H, Ar—H), 7.47 (t, J=7.37 Hz, 1H, Ar—H), 7.64 (t, J=7.45 Hz, 1H, Ar—H), 8.02 (d, J=7.87 Hz, 1H, Ar—H).

IR (KBr, cm$^{-1}$): 3420 (m), 1720 (s), 1665 (s), 1460 (m), 735 (m).

MS (m/e): 175 (M+), 118 (M$^+$—CONCH$_3$).

Anal. Calcd.: C, 68.56; H, 5.18; N, 8.00. Found: C, 68.57; H, 5.40; N, 8.01.

The following compound was obtained in substantially the same manner as that of Example 2.

2-Ethyl-1,3(2H, 4H)-isoquinolinedione

NMR (DMSO-d$_6$, 200 MHz): δ 1.1 (t, J=7.0 Hz, 3H, —NCH$_2$CH$_3$), 3.89 (q, J=6.8 Hz, 2H, —NCH$_2$CH$_3$), 4.11 (s, 2H, —CH$_2$CO), 7.34–7.49 (m, 2H, Ar—H), 7.63 (dt, J=7.8 Hz, 2.0 Hz, 1H, Ar—H), 8.05 (d, J=7.6 Hz, 1H, Ar—H).

IR (KBr, cm$^{-1}$): 3420 (m), 1710 (s), 1650 (s), 1450 (s), 740 (m).

MS (m/e): 189 (M+), 174 (M$^+$—CH$_3$), 146 (M$^+$—CH$_3$,—CO), 118 (M$^+$—CONCH$_2$CH$_3$), 90 (M$^+$—CON(CH$_2$CH$_3$)CO).

Anal. Calcd.: C, 69.83; H, 5.86; N, 7.40. Found: C, 69.64; H, 5.73; N, 7.36.

M.P. 103°–104° C.

EXAMPLE 3

2-Methylspiro[isoquinoline-4(1H),3'-pyrrolidine]-1,2',3,5'(2H)-tetrone

To a cold (−78° C.) solution of 4-(2-amino-2-oxoethyl)-1,2,3,4-tetrahydro-1,3-dioxo-4-isoquinolinecarboxylic acid methyl ester (2.5 g, 8.62 mmol) in anhydrous THF (80 mL) was added lithium bis(trimethylsilyl)amide (17.24 mL, 17.24 mmol, 1.0M in THF) over a 10 minute period. After stirring at −78° C. for 10 hours, the mixture was poured into H$_2$O, acidified with HCl (2N), extracted with EtOAc, and dried over MgSO$_4$. The crude product was purified by flash chromatography (hexane/EtOAc 1/1) to yield a white solid, m.p. 224°–225° C. (1.25 g, 56.8%).

NMR (DMSO-d$_6$, 400 MHz): δ 3.23 (s, 3H, —N—CH$_3$), 3.43 (q, J=18.3 Hz, 2H, —CH$_2$CONHCO—), 7.60–7.62 (m, 2H, Ar—H), 7.74 (dt, J=7.6 Hz, 1.22 Hz, 1H, Ar—H), 8.14 (dd, J=7.72 Hz, 0.95 Hz, 1H, Ar—H), 12.0 (s, 1H, —CONHCO—).

IR (KBr, cm$^{-1}$): 3340 (s), 1725 (s), 1660 (s), 1310 (s), 765 (m).

MS (m/e): 259 (M+H)+.

Anal. Calcd. for $C_{13}H_{10}N_2O_4 \times \frac{1}{4}H_2O$: C, 59.42; H, 3.91; N, 10.66. Found: C, 59.44; H, 3.97; N, 10.54.

The following compounds were obtained in substantially the same manner as that of Example 3.

7-Chloro-2-methylspiro[isoquinoline-4(1H)3'-pyrolidine]-1,2',3,5'(2H)-tetrone NMR (DMSO-d$_6$, 400 MHz): δ 3.23 (s, 3H, —NCH$_3$), 3.4 (q, J=18.26 Hz, 2H, —CH$_2$CONH—), 7.7 (d, J=8.45 Hz, 1H, Ar—H), 7.82 (dd, J=8.51 Hz, 2.38 Hz, 1H, Ar—H), 8.09 (d, J=2.31 Hz, 1H, Ar—H), 12.02 (brs, 1H, —CONHCO—).

IR (KBr, cm$^{-1}$): 3440 (m), 1720 (s), 1660 (s), 1310 (m), 1180 (m), 690 (m).

MS (m/e): 293 (M+H)+.

Anal. Calcd. for $C_{13}H_9N_2ClO_4 \times \frac{1}{3}H_2O$: C, 52.56; H, 3.13; N, 9.38. Found: C, 52.72; H, 3.14; N, 9.33.

M.P. 234°–236° C.

6-Chloro-2-methylspiro[isoquinoline-4(1H)3'-pyrolidine]-1,2',3,5'(2H)-tetrone NMR (DMSO-d$_6$, 400 MHz): δ 3.22 (s, 3H, —NCH$_3$), 3.38 (s, 2H, CH$_2$CONH—), 7.66 (dd, J=8.55 Hz, 2.02 Hz, 1H, Ar—H), 7.92 (d, J=1.97 Hz, 1H, Ar—H), 8.13 (d, J=8.52 Hz, 1H, Ar—H), 11.99 (s, 1H, —CONHCO—).

IR (KBr, cm$^{-1}$): 3350 (m), 1750 (s), 1730 (m), 1660 (s), 1310 (s), 690 (m).

MS (m/e): 293 (M+H)+.

Anal. Calcd.: C, 53.35; H, 3.10; N, 9.57. Found: C, 53.43; H, 3.09; N, 9.38.

M.P. 213°–214° C.

6-Bromo-2-methylspiro[isoquinoline-4(1H),3'-pyrolidine]-1,2',3,5'(2H)-tetrone NMR (DMSO-d$_6$, 400 MHz): δ 3.22 (s, 3H, —NCH$_3$), 3.37 (s, 2H, —CH$_2$CONH—), 7.80 (dd, J=8.42 Hz, 1.67 Hz, 1H, Ar—H), 8.05 (m, 2H, Ar—H), 11.98 (s, 1H, —CONHCO—).

IR (KBr, cm$^{-1}$): 3260 (s), 1720 (s), 1660 (s).

MS (m/e): 337 (M+H)+.

Anal. Calcd.: C, 46.31; H, 2.69; N, 8.31. Found: C, 46.04; H, 2.66; N, 8.01.

M.P. 245°–247° C.

EXAMPLE 4

6-Chloro-2-Methyl-1,3(2H, 4H)-isoquinolinedione

In a pressure glass vessel were placed 5-chloro-2-(methoxycarbonyl)benzeneacetic acid methyl ester (20.0 g, 82.47 mmol) and MeOH (150 mL). Anhydrous monomethylamine was passed through the mixture for 30 minutes. The vessel was introduced into an oil bath and heated at 75° C. for 24 hours. After cooling to room temperature, the mixture was poured into H$_2$O, acidified with HCl (2N), extracted with EtOAc, and dried over MgSO$_4$. The crude product was purified by flash chromatography (hexane/EtOAc 2/1) to yield a yellow solid, m.p. 167°–180° C. (11.1 g, 64.2%).

NMR (DMSO-d$_6$, 200 MHz): δ 3.18 (s, 3H, —NCH$_3$), 4.12 (s, 2H, —CH$_2$CO—), 7.52 (m, 2H, Ar—H), 8.04 (d, J=8.8 Hz, 1H, Ar—H).

IR (KBr, cm$^{-1}$): 3440 (m), 1665 (s), 1300 (s), 770 (m).

MS (m/e): 209 (M+), 152 (M+—CONCH$_3$), 124[M+—CON(CH$_3$)CO—].

Anal. Calcd.: C, 57.30; H, 3.85; N, 6.68. Found: C, 57.10; H, 3.79; N, 6.69.

The following compound was prepared in substantially the same manner as that of Example 4.

7-Chloro-2-methyl-1,3(2H, 4H)-isoquinolinedione

NMR (DMSO-d$_6$, 200 MHz): δ 3.19 (s, 3H, —NCH$_3$), 4.11 (s, 2H, —CH$_2$CO—), 7.41 (d, J=8.6 Hz, 1H, Ar—H), 7.73 (dd, J=8.2 Hz, 2.2 Hz, 1H, Ar—H), 7.96 (d, J=1.8 Hz, 1H, Ar—H).

IR (KBr, cm$^{-1}$): 3420 (m), 1710 (m), 1635 (s), 1295 (m), 770 (m).

MS (m/e): 209 (M+), 152 (M+—CONCH$_3$), 124[M+—CON(CH$_3$)CO—].

Anal. Calcd.: C, 57.30; H, 3.85; N, 6.68. Found: C, 57.34; H, 3.84; N, 6.60.

M.P. 158°–160° C.

EXAMPLE 5

(2-Carboxyphenyl)propanedioic Acid Dimethyl Ester

To a rapidly stirred cold suspension (0° C.) of 2-bromobenzoic acid (30.0 g, 149.32 mmol), cuprous bromide (2.14 g, 14.93 mmol) and dimethyl malonate (300 mL) was added NaH (80% in mineral oil, 10.75 g, 358.37 mmol) over a 30 minute period, while a stream of dry N$_2$ was passed over the mixture. After the addition of the NaH had been completed, the mixture was stirred for 10 minutes at room temperature and 30 minutes at 70° C. (external oil bath temperature). At this point, the suspension had turned to a solid mass, which was dissolved in H$_2$O (1000 mL). The aqueous layer was extracted with diethyl ether (3×500 mL) and was acidified with HCl (2N). The mixture was extracted with EtOAc and dried over MgSO$_4$. Evaporation gave an off-white solid which was recrystallized from Et$_2$O/hexane (−20° C.) to give a white solid (34.2 g).

NMR (DMSO-d$_6$, 400 MHz): δ 3.67 [s, 6H, —CH(CO$_2$CH$_3$)$_2$], 5.72 [s, 1H, —CH(CO$_2$CH$_3$)$_2$], 7.3 (d, J=7.76 Hz, 1H, Ar—H), 7.45 (dt, J=7.66 Hz, 1.12 Hz, 1H, Ar—H), 7.6 (dt, J=7.66 Hz, 1.45 Hz, 1H, Ar—H), 7.94 (dd, J=7.8 Hz, 1.33 Hz, 1H, Ar—H), 13.2 (s, 1H, —CO$_2$H).

IR (KBr, cm$^{-1}$): 3300–2700 (br), 1750 (s), 1730 (s), 1680 (s), 1430 (m), 730 (m).

MS (m/e): 252 (M+), 220 (M+—CH$_3$OH), 188 (M+-2×CH$_3$OH).

Anal. Calcd.: C, 57.14; H, 4.80. Found: C, 57.05; H, 4.78.

M.P. 119°–120° C.

The following compounds were prepared in substantially the same manner as that of Example 5.

(2-Carboxy-6-fluorophenyl)propanedioic Acid Dimethyl Ester

NMR (DMSO-d$_6$, 400 MHz): δ 3.68 [s, 6H, (—CO$_2$Me)$_2$], 5.79 (s, 1H, Ar—CH—), 7.12 (dd, J=10.06 Hz, 2.61 Hz, 1H, Ar—H), 7.33 (dt, J=8.48 Hz, 2.64 Hz, 1H, Ar—H), 8.03 (dd, 8.77 Hz, 6.17 Hz, 1H, Ar—H).

IR (KBr, cm$^{-1}$): 3400–2700 (br), 1730 (s), 1680 (s), 750 (m)

MS (m/e): 270 (M+), 238 (M+—CH$_3$OH), 210 (M+—CH$_3$OH, —CO), 151 (M+—CH$_3$OH—CO—CO$_2$CH$_3$)

M.P. 121.5°–123.0° C.

(2-Carboxy-6-methoxyphenyl)propanedioic Acid Diethyl Ester

NMR (DMSO-d$_6$, 400 MHz): δ 1.16 [t, J=7.02 Hz, 6H, (—CO$_2$CH$_2$CH$_3$)$_2$], 3.79 (s, 3H, —OCH$_3$), 4.13 [q, J=7.02 Hz, 4H, (—CO$_2$CH$_2$CH$_3$)$_2$], 5.56 (s, 1H, Ar—CH—), 7.16 (dd, J=8.63 Hz, 2.81 Hz, 1H, Ar—H), 7.22 (d, J=8.62 Hz, 1H, Ar—H), 7.42 (d, J=2.79 Hz, 1H, Ar—H).

IR (KBr, cm$^{-1}$): 3450–2550 (br), 1750 (s), 1730 (s).
MS (m/e): 310 (M+), 264 (M+-EtOH), 218 (M+-2EtOH).
Anal. Calcd.: C, 58.06; H, 5.85. Found: C, 57.88; H, 5.67.
M.P. 94.5°–96.0° C.

(2-Carboxy-6-bromophenyl)propanedioic Acid Dimethyl Ester

NMR (DMSO-d$_6$, 400 MHz): δ 3.68 ]s, 6H, —(CO$_2$CH$_3$)$_2$], 5.74 (s, 1H, Ar—CH—), 7.5 (d, J=2.02 Hz, 1H, Ar—H), 7.70 (dd, J=8.4 Hz, 1.98 Hz, 1H, Ar—H), 7.87 (d, J=8.41 Hz, 1H, Ar—H).

IR (KBr, cm$^{-1}$): 3400–2300 (br), 1745 (s), 1720 (s), 1695 (s).
MS (m/e): 330 (M+), 298 (M+—CH$_3$OH).
Anal. Calcd.: C, 43,53; H, 3.35. Found: C, 43.56; H, 3.23.
M.P. 127°–128° C.

EXAMPLE 6

2-[(4-Bromo-2-fluorophenyl)methyl]-1,2,3,4-tetrahydro-1,3-dioxo-4-isoquinolinecarboxylic Acid Methyl Ester A mixture of (2-carboxyphenyl)propanedioic acid dimethyl ester (5.0 g, 19.84 mmol) and SOCl$_2$ (20 g) was refluxed for 1 and ½ hours. The volatiles were removed in vacuo and the acid chloride was dissolved in THF (20 mL). In a second flask were placed 4-bromo-2-fluorobenzylamine (4.67 g, 22.91 mmol), triethylamine (15.96 mL, 114.55 mmol) and THF (150 mL). The contents of the first flask were added to the second flask and the mixture was stirred for 30 minutes. The formed suspension was poured into H$_2$O (1000 mL), stirred for 10 minutes and acidified with HCl (2N). The mixture was extracted with EtOAc and the organic layer was dried over MgSO$_4$. Evaporation gave a yellowish solid which was recrystallized from acetone/ether/hexane (at −20° C.) to yield a white solid (6.91 g, m.p. 149°–150° C.).

NMR (DMSO-d$_6$, 400 MHz): δ [3.67, 3.99 (s, 3H, —CO$_2$CH$_3$, tautomeric)], [5.06 (q, J=15.4 Hz), 5.29 (s) 2H, N—CH$_2$—, tautomeric], 5.03 (s, 1H, —CH CO$_2$CH$_3$, tautomeric), 7.07–8.44 (m, 7H, Ar—H, tautomeric).

IR (KBr, cm$^{-1}$): 1675 (s), 1610 (s), 1490 (s), 795 (m).
MS (m/e): 405 (M+), 373 (M+—MeOH).
Anal. Calcd.: C, 53.22; H, 3.23; N, 3.45. Found: C, 52.91; H, 3.20; N, 3.27.
M.P. 149°–150° C.

The following compounds were prepared in substantially the same manner as that of Example 6.

2-[(4-Bromo-2-fluorophenyl)methyl-6-fluoro-1,2,3,4-tetrahydro-1,3-dioxo-4-isoquinolineacetic Acid Methyl Ester NMR (DMSO-d$_6$, 400 MHz): δ 3.98 (s, 3H, —CO$_2$CH$_3$), 5.27 (s, 2H, —NCH$_2$—), 7.08 (t, J=7.95 Hz, 1H, Ar—H), 7.2 (m, 1H, Ar—H), 7.34 (m, 2H, Ar—H, —OH), 7.54 (m, 1H, Ar—H), 8.1–8.26 (m, 2H, Ar—H)

IR (KBr, cm$^{-1}$): 1680 (s), 1660 (s), 1610 (s), 785 (m).
MS (m/e): 423 (M+), 391 (M+—CH$_3$OH).
Anal. Calcd.: C, 50.97; H, 2.85; N, 3.30. Found: C, 50.86; H, 2.86; N, 3.33.
M.P. 157°–158° C.

2-[(4-Bromo-2-fluorophenyl)methyl]-7-methoxy-1,2,3,4-tetrahydro-1,3-dioxo-4-isoquinolineacetic Acid Ethyl Ester NMR (DMSO-d$_6$, 400 MHz): δ [1.07 (t), 1.4 (t), 3H, —CO$_2$CH$_2$CH$_3$, tautomeric], [3.82 (s), 3.83 (s), 3H, —OCH$_3$, tautomeric], [4.1 (q), 4.46 (q), 2H, —CO$_2$CH$_2$CH$_3$, tautomeric], [5.05 (dd), 5.3 (s), tautomeric, —NCH$_2$—], [5.25 (s), 8.2 (brs), 1H, Ar—CH—, ArCH=C—OH], [7.1 (t), 7.2 (t), tautomeric, 1H, Ar—H], 7.35–7.4 (m, 3H, Ar—H), [7.58 (d), 7.62 (d), tautomeric, 1H, Ar—H], [7.56 (d), 8.41 (d) tautomeric, 1H, Ar—H].

IR (KBr, cm$^{-1}$): 3450 (s), 1680 (s), 1620 (s), 1610 (s).
MS (m/e): 449 (M+), 403 (M+—EtOH).
M.P. 139°–140° C.

6-Bromo-1,2,3,4-tetrahydro-2-methyl-1,3-dioxo-4-isoquinolinecarboxylic Acid Methyl Ester NMR (DMSO-d$_6$, 400 MHz): δ [3.2 (s), 3.42 (s), 3H, tautomeric, N—CH$_3$], [3.7 (s), 4.01 (s), 3H, tautomeric, —CO$_2$CH$_3$], [5.33 (s), 1H, tautomeric, Ar—CH—], [7.5 (dd), 7.8 (dd), tautomeric, 1H, Ar—H], [8.0 (d), 8.08 (d), tautomeric, 1H, Ar—H], [8.51 (d), 7.63 (d), tautomeric, 1H, Ar—H].

IR (KBr, cm$^{-1}$): 1665 (s), 1590 (s), 780 (m).
MS (m/e): 311 (M+).
Anal. Calcd.: C, 46.18; H, 3.23; N, 4.49. Found: C, 45.83; H, 2.77; N, 4.38.
M.P. 190°–191° C.

EXAMPLE 7

(R)-(+)-2-[(4-Bromo-2-fluorophenyl)methyl]-spiro[isoquinoline-4(1H),3'-pyrrolidine]-1,2',3,5'-tetrone;

(S)-(−)-2-[(4-Bromo-2-fluorophenyl)methyl]-spiro[isoquinoline-4(1H),3'-pyrrolidine]-1,2',3,5'-tetrone Step (k) Preparation of 2-[(4-Bromo-2-fluorophenyl)-methyl]-1,2,3,4-tetrahydro-1,3-dioxo-4-isoquinolinecarboxylic Acid Menthyl Ester To a cold (−78° C.) solution of 2-[(4-bromo-2-fluorophenyl)methyl]-1,3(2H, 3H)-isoquinolinedione (9.0 g, 25.86 mmol) in anhydrous THF (120 mL) was added lithium bis(trimethylsilyl)amide (1.0M solution in THF, 56.91 mL, 56.91 mmol), dropwise over a 10 minute period. After stirring for 3 hours, (−)menthyl chloroformate (8.48 mL, 38.79 mmol) was added and the reaction was allowed to warm up to room temperature. The mixture during that period turned a dark color. It was stirred an additional 30 minutes and quenched with H$_2$O. The dark solution was poured into H$_2$O, acidified with HCl (2N) and extracted with EtOAc. The organic extracts were dried over MgSO$_4$. Evaporation and purification by flash chromatography on acid-washed silica gel (5% H$_3$PO$_4$ in MeOH) gave a clear oil (10.2 g).

NMR (DMSO-d$_6$, 200 MHz): δ 0.3–1.9 (m, 18H, menthyl), 4.3–4.6 (m, 1H, —CO$_2$CH—), 5.0–5.35 (m, 3H, —NCH$_2$—, ArCHCO$_2$—), 7.1–7.8 (m, 6H, Ar—H), 8.2–8.5 (m, 1H, Ar—H).

IR (cm$^{-1}$): 1780 (s), 1740 (s), 1690 (s), 835 (m).

MS (m/e): 529 (M+), 391 (M+-menthyl).

The following compound was prepared in substantially the same manner as that of Example 7, Step k).

2-[(4-Bromo-2-fluorophenyl)methyl]-6-fluoro-1,2,3,4-tetrahydro-1,3-dioxo-4-isoquinolinecarboxylic Acid Menthyl Ester NMR (DMSO-d$_6$, 200 MHz): δ 0.3–2.2 (m, 18H, menthyl), 4.4–4.7 (m, 1H, —CO$_2$CH—), 5.0–5.4 (m, 2H, —NCH$_2$—), 7.1–7.6 (m, 4H, Ar—H), 8.1–8.3 (m, 2H, Ar—H).

IR (KBr, cm$^{-1}$): 3440 (m), 1690 (s), 1620 (s).

MS (m/e): 547 (M+), 409 (M+-menthyl).

Step (l) Preparation of 2-[(4-Bromo-2-fluorophenyl)methyl]-1,2,3,4-tetrahydro-4-(menthoxycarbonyl)-1,3-dioxo-4-isoquinolineacetic Acid 1,1-Dimethylethyl Ester To a mixture of 2-[(4-bromo-2-fluorophenyl)methyl]-1,2,3,4-tetrahydro-1,3-dioxo-4-isoquinoline carboxylic acid menthyl ester (7.62 g, 14.37 mmol), K$_2$CO$_3$ (3.96 g, 28.74 mmol) in DMF (100 mL) was added tert-butyl bromoacetate (4.64 mL, 28.74 mmol). The mixture was stirred at 85° C. for 2 hours, poured into H$_2$O (1000 mL) and extracted with EtOAc. The organic extracts were dried over MgSO$_4$. Evaporation and purification by flash chromatography (hexane/EtOAc:4/1) gave a clear oil (6.9 g, diastereomeric mixture). The two diastereomers were separated by preparative HPLC on prep. Pac silica column, (μ poraSi/125 Å, 15–20 μsilica) by elution with hexane/CH$_2$Cl$_2$ to give the less polar A-diastereomer as a white solid (2.4 g) and the more polar diastereomer B as a clear oil (2.2 g). The diastereomeric purity was determined by analytical HPLC, on Dynamax silica 25 cmx4.1 mm and was found to be greater than 99% for both diastereomers.

Spectroscopic Data: Less Polar A-Diastereomer

NMR (DMSO-d$_6$, 400 MHz): δ 0.42 (m, 1H, menthyl), 0.56 (d, J=7.4 Hz, 3H, —CHCH$_3$), 0.64 (d, J=7.4 Hz, 3H, —CHCH$_3$), 0.72 (d, J=6.2 Hz, 3H, —CHCH$_3$), 0.92–0.97 (m, 2H, menthyl), 1.05 [s, 9H, —C(CH$_3$)$_3$], 1.22–1.39 (m, 3H, menthyl), 2.5–2.6 (m, 2H, menthyl), 3.55 (dd, J=17.02 Hz, 2H, —CH$_2$CO$_2$—), 4.46 (m, 1H, —OCH—), 5.10 (dd, J=15.02 Hz, 2H, —NCH$_2$—), 7.2 (t, J=8.16 Hz, 1H, Ar—H), 7.33 (dd, J=8.44 Hz, 1.7 Hz, 1H, Ar—H), 7.53 (dd, J=9.7 Hz, 1.85 Hz, 1H, Ar—H), 7.6–7.77 (m, 2H, Ar—H), 7.79 (dt, J=7.67 Hz, 1.35 Hz, 1H, Ar—H), 8.2 (dd, J=7.77 Hz, 1.0 Hz, 1H, Ar—H).

IR (KBr, cm$^{-1}$): 1715 (s), 1670 (s), 735 (m).

MS (m/e): 644 (M+H)+, 587 [M+H—C(CH$_3$)$_3$]+.

M.P. 50°–51° C.

Spectroscopic Data: More Polar B-Diastereomer

NMR (DMSO-d$_6$, 400 MHz): δ 0.1 (d, J=6.6 Hz, 3H, —CHCH$_3$), 0.15 (m, 1H, menthyl), 0.42 (d, J=6.6 Hz, 3H, —CHCH$_3$), 0.58–0.61 (m, 1H, menthyl), 0.64–0.9 (m, 3H, menthyl), 0.78 (d, J=6.2 Hz, 3H, —CHCH$_3$), 1.04 [s, 9H, —C(CH$_3$)$_3$], 1.2–1.38 (m, 1H, menthyl), 1.4 (m, 1H, menthyl), 1.43–1.47 (m, 2H, menthyl), 3.54 (dd, J=17.0 Hz, 2H, —CH$_2$CO$_2$—), 4.24 (m, 1H, —OCH—), 4.96 (d, J=14.56 Hz, 1H, —NCH—), 5.32 (d, J=14.56 Hz, 1H, —NCH—), 7.29 (t, J=7.96 Hz, 1H, Ar—H), 7.35 (dd, J=8.31 Hz, 1.8 Hz, 1H, Ar—H), 7.53–7.55 (m, 2H, Ar—H), 7.61 (dt, J=8.29 Hz, 0.9 Hz, 1H, Ar—H), 7.76 (dt, J=7.65 Hz, 1.4 Hz, 1H, Ar—H), 8.22 (dd, J=7.85 Hz, 1.2 Hz, 1H, Ar—H).

IR (CHCl$_3$, cm$^{-1}$): 1715 (s), 1670 (s).

MS (m/e): 643 (M+), [M+ +H—C(CH$_3$)$_3$], 449 [M+ +H—C(CH$_3$)$_3$-menthyl].

The following compounds were prepared in substantially the same manner as that of Example 7, Step(l).

2-[(4-Bromo-2-fluorophenyl)methyl]-6-fluoro-1,2,3,4-tetrahydro-4-(menthoxycarbonyl)-1,3-dioxo-4-isoquinoline Acetic Acid 1,1-Dimethylethyl Ester Less Polar Diastereomer: A-Diastereomer NMR (DMSO-d$_6$, 400 MHz): δ 0.54 (d, J=6.86 Hz, 3H, —CHCH$_3$), 0.55 (m, 1H, menthyl), 0.65 (d, J=6.97 Hz, 3H, —CHCH$_3$), 0.74 (d, J=6.38 Hz, 3H, —CHCH$_3$), 0.8–0.96 (m, 3H, menthyl), 1.09 [s, 9H, —C(CH$_3$)$_3$], 1.23–1.4 (m, 3H, menthyl), 1.5 (m, 2H, menthyl), 3.5 (d, J=17.4 Hz, 1H, —CH$_2$CO$_2$—), 3.73 (d, J=17.4 Hz, 1H, —CH$_2$CO$_2$—), 4.46 (dt, J=10.7 Hz, 4.23 Hz, 1H, —OCH—), 5.1 (dd, J=15.0 Hz, 2H, —NCH$_2$—), 7.2 (t, J=8.15 Hz, 1H, Ar—H), 7.33 (dd, J=8.3 Hz, 1.76 Hz, 1H, Ar—H), 7.48 (dt, J=8.52 Hz, 2.4 Hz, 1H, Ar—H), 7.54 (dd, J=9.75 Hz, 1.85 Hz, 1H, Ar—H), 7.61 (dd, J=9.58 Hz, 2.46 Hz, 1H, Ar—H), 8.27 (dd, J=8.81 Hz, 5.8 Hz, 1H, Ar—H).

IR (KBr, cm$^{-1}$): 1750 (s), 1730 (s), 1680 (s), 1620 (s).

MS (m/e): 662 (M+H)+, 606 [M+H—C(CH$_3$)$_3$], 468 [M+H—C(CH$_3$)$_3$-menthyl], 424 [M+H—C(CH$_3$)$_3$-menthyl—CO$_2$].

Anal. Calcd.: C, 59.82; H, 5.78; N, 2.11. Found: C, 60.19; H, 5.72; N, 2.13.

M.P. 54°–55° C.

More Polar Diastereomer: B-Diastereomer

NMR (DMSO-d$_6$, 400 MHz): δ 0.15 (m, 1H, menthyl), 1.73 (d, J=6.87 Hz, 3H, —CHCH$_3$), 0.45 (d, J=6.92 Hz, 3H, —CHCH$_3$), 0.6–0.75 (m, 2H, menthyl), 0.77 (d, J=6.55 Hz, 3H, —CHCH$_3$), 0.8–0.95 (m, 2H), 1.09 [s, 9H, C(CH$_3$)$_3$], 1.2–1.35 (m, 1H), 1.4–1.56 (m, 3H, Ar—H), 3.5 (d, J=17.36 Hz, 1H, —CH$_2$CO$_2$—), 3.7 (d, J=17.36 Hz, 1H, —CH$_2$CO$_2$—), 4.27 (dt, J=10.54 Hz, 6.61 Hz, 1H, —OCH—), 5.0 (d, J=14.67 Hz, 1H, —NCH$_2$—), 5.3 (d, J=14.67 Hz, 1H, —NCH$_2$—), 7.28 (t, J=8.0 Hz, 1H, Ar—H), 7.36 (dd, J=8.34 Hz, 1.75 Hz, 1H, Ar—H), 7.50 (dt, J=8.5 Hz, 2.5 Hz, 1H, Ar—H), 7.54 (dd, J=9.61 Hz, 1.85 Hz, 1H, Ar—H), 7.6 (dd, J=9.57 Hz, 2.38 Hz, 1H, Ar—H), 8.3 (dd, J=8.83 Hz, 5.8 Hz, 1H, Ar—H).

IR (KBr, cm$^{-1}$): 1745 (s), 1725 (s), 1680 (s), 1610 (s).

MS (m/e): 662 (M+H)+, 606 [M+H—C(CH$_3$)$_3$], 468 [M+H—C(CH$_3$)$_3$-menthyl], 424 [M+H—C(CH$_3$)$_3$-menthyl-CO$_2$].

Anal. Calcd.: C, 59.82; H, 5.78; N, 2.11. Found: C, 59.91; H, 5.55; N, 2.20.

M.P. 49°–50° C.

Step (m) Preparation of 2-[(4-Bromo-2-fluorophenyl)methyl]-1,2,3,4-tetrahydro-4-(menthoxycarbonyl)-1,3-dioxo-4-isoquinolineacetic Acid (A-Diastereomer)

A mixture of 2-[(4-bromo-2-fluorophenyl)methyl]-1,2,3,4-tetrahydro-4-(menthoxycarbonyl)-1,3-dioxo-4-isoquinolineacetic acid 1,1-dimethylethyl ester (less polar, A-diastereomer, 7.0 g, 10.87 mmol), CH$_2$Cl$_2$ (60 mL) and CF$_3$CO$_2$H (15 mL) was stirred at room temperature for 5 hours. The volatiles were removed in vacuo and the residue was purified by flash chromatography on acid-washed silica gel (5% H$_3$PO$_4$ in MeOH), to give a white solid (6.0 g).

NMR (DMSO-d$_6$, 400 MHz): δ 0.5 (q, J=7.4 Hz, 1H, —CHCH$_3$), 0.58 (d, J=6.6 Hz, 3H, —CHCH$_3$), 0.66 (d, J=6.6 Hz, 3H, —CHCH$_3$), 0.71 (d, J=7.4 Hz, 3H,

—CHCH$_3$), 0.82–1.05 (m, 3H, menthyl), 1.2–1.56 (m, 5H, menthyl), 3.6 (dd, J=17.65 Hz, 2H, —CH$_2$CO$_2$H), 4.46 (dt, 10.67 Hz, 3.9 Hz, 1H, —OCH—), 5.1 (dd, J=15.2 Hz, 2H, —NCH$_2$—), 7.17 (t, J=8.2 Hz, 1H, Ar—H), 7.3 (dd, J=8.28 Hz, 1.7 Hz, 1H, Ar—H), 7.53 (dd, J=9.8 Hz, 1.9 Hz, 1H, Ar—H), 7.6 (m, 2H, Ar—H), 7.77 (dt, J=7.64 Hz, 1.4 Hz, 1H, Ar—H), 8.17 (dd, J=8.16 Hz, 1.5 Hz, 1H, Ar—H).

IR (KBr, cm$^{-1}$): 3350–2700 (br), 1745 (s), 1720 (s), 1675 (s), 745 (m).

MS (m/e): 587 (M+), 449 (M+-menthyl).

Anal. Calcd.: C, 59.19; H, 5.31; N, 2.38. Found: C, 59.30; H, 4.99; N, 2.28.

M.P. 79°–80° C.

The following compound was prepared in substantially the same manner as that of Example 7, Step(m).

2-[(4-Bromo-2-fluorophenyl)methyl]-6-fluoro-1,2,3,4-tetrahydro-4-(menthoxycarbonyl)-1,3-dioxo-4-isoquinolineacetic Acid (A-Diastereomer)

NMR (DMSO-d$_6$, 400 MHz): δ 0.51 (m, 1H, menthyl), 5.5 (d, J=6.92 Hz, 3H, —CHCH$_3$), 0.68 (d, J=6.96 Hz, 3H, —CHCH$_3$), 0.69 (m, 1H, menthyl), 0.74 (d, J=6.46 Hz, 3H, —CHCH$_3$), 0.8–1.0 (m, 2H, menthyl), 1.25–1.4 (m, 3H, menthyl), 1.5 (m, 2H, menthyl), 3.55 (d, J=17.9 Hz, 1H, —CH$_2$CO$_2$H), 3.77 (d, J=17.9 Hz, 1H, —CH$_2$CO$_2$H), 4.46 (dt, J=10.81 Hz, 4.51 Hz, 1H, —OCH—), 5.07 (dd, J=15.2 Hz, 2H, —NCH$_2$—), 7.15 (t, J=8.24 Hz, 1H, Ar—H), 7.31 (dd, J=8.35 Hz, 1.82 Hz, 1H, Ar—H), 7.46 (dt, J=8.49 Hz, 2.49 Hz, 1H, Ar—H), 7.54 (dd, J=9.77 Hz, 1.87 Hz, 1H, Ar—H), 7.61 (dd, J=9.65 Hz, 2.45 Hz, 1H, Ar—H), 8.25 (dd, J=8.8 Hz, 5.87 Hz, 1H, Ar—H), 12.75 (brs, 1H, —CO$_2$H).

IR (KBr, cm$^{-1}$): 3450–2700 (br), 1745 (s), 1720 (s), 1680 (s), 1610 (s).

MS (m/e): 606 (M+H)+, 468 (M+H-menthyl).

Anal. Calcd.: C, 57.43; H, 4.99; N, 2.31. Found: C, 57.40; H, 4.76; N, 2.35.

M.P. 84°–85° C.

Step (n) Preparation of 2-[(4-Bromo-2-fluorophenyl)methyl]-1,2,3,4-tetrahydro-4-(menthoxycarbonyl)-1,3-dioxo-4-isoquinolineacetic Acid (B-Diastereomer)

A mixture of 2-[(4-bromo-2-fluorophenyl)methyl]-1,2,3,4-tetrahydro-4-(menthoxycarbonyl)-1,3-dioxo-4-isoquinolineacetic acid 1,1-dimethylethyl ester (more polar, B-diastereomer, 6.8 g, 10.56 mmol), CH$_2$Cl$_2$ (80 mL) and CF$_3$CO$_2$H (20 mL) was stirred at room temperature for 5 hours. The volatiles were removed in vacuo and the residue was purified by flash chromatography on acid-washed silica gel (5% H$_3$PO$_4$ in MeOH) to give a white solid (5.81 g).

NMR (DMSO-d$_6$, 400 MHz): δ 0.16 (d, J=6.6 Hz, 3H, —CHCH$_3$), 0.22 (q, J=7.2 Hz, 1h, —CHCH$_3$), 0.42 (d, J=6.6 Hz, 3H, —CHCH$_3$), 0.6 (m, 1H, menthyl), 0.8 (d, J=7.2 Hz, 3H, —CHCH$_3$), 0.7–0.95 (m, 4H, menthyl), 1.25 (m, 1H, menthyl), 1.42 (m, 1H, Ar—H), 1.45–1.48 (m, 2H, menthyl), 3.6 (dd, J=17.75 Hz, 2H, —CH$_2$CO$_2$H), 4.25 (dt, J=10.7 Hz, 3.2 Hz, 1H, —OCH—), 5.0 (dd, J=14.7 Hz, 2H, —NCH$_2$—), 7.27 (t, J=8.05 Hz, 1H, Ar—H), 7.34 (dd, J=8.28 Hz, 1.7 Hz, 1H, Ar—H), 7.53–7.61 (m, 3H, Ar—H), 7.74 (dt, J=7.65 Hz, 1.3 Hz, 1H, Ar—H), 8.2 (dd, J=7.86 Hz, 1.16 Hz, 1H, Ar—H).

IR (KBr, cm$^{-1}$): 3350–2700 (br), 1745 (s), 1720 (s), 1675 (s), 745 (m).

MS (m/e): 588 (M+H)+, 450 (M+H-menthyl).

Anal. Calcd.: C, 59.19; H, 5.31; N, 2.38. Found: C, 59.40; H, 5.08; N, 2.22.

M.P. 132°–133° C.

The following compound was prepared in substantially the same manner as that of Example 7, Step(n).

2-[(4-Bromo-2-fluorophenyl)methyl]-6-fluoro-1,2,3,4-tetrahydro-4-(menthoxycarbonyl)-1,3-dioxo-4-isoquinolineacetic Acid (B-Diastereomer)

NMR (DMSO-d$_6$, 400 MHz): δ 0.19 (d, J=6.89 Hz, 3H, —CHCH$_3$), 0.23 (m, 1H, menthyl), 0.45 (d, J=6.92 Hz, 3H, —CHCH$_3$), 0.6 (m, 1H, menthyl), 0.72 (m, 1H, menthyl), 0.77 (d, J=6.52 Hz, 3H, —CHCH$_3$), 0.8–0.9 (m, 2H, menthyl), 1.3 (m, 1H, menthyl), 1.42 (m, 1H, menthyl), 1.5–1.54 (m, 2H, menthyl), 3.52 (d, J=17.92 Hz, 1H, —CH$_2$CO$_2$H), 3.75 (d, J=17.92 Hz, 1H, —CH$_2$CO$_2$H), 4.28 (dt, J=10.6 Hz, 4.24 Hz, 1H, —OCH—), 4.93 (d, J=14.75 Hz, 1H, —NCH$_2$—), 5.29 (d, J=14.75 Hz, 1H, —NCH$_2$—), 7.25 (t, J=8.09 Hz, 1H, ArH), 7.34 (dd, 8.27 Hz, 1.74 Hz, 1H, Ar—H), 7.46 (dt, J=8.57 Hz, 2.4 Hz, 1H, Ar—H), 7.53 (dd, J=9.62 Hz, 1.84 Hz, 1H, Ar—H), 7.58 (dd, J=9.6 Hz, 2.42 Hz, 1H, Ar—H), 8.26 (dd, J=8.85 Hz, 5.87 Hz, 1H, Ar—H), 12.75 (brs, 1H, —CO$_2$H).

IR (KBr, cm$^{-1}$): 3450–2700 (br), 1750 (s), 1725 (s), 1680 (s), 1615 (s).

MS (m/e): 606 (M+H)+, 468 (M+H—menthyl), 424 (M+H—menthyl—CO$_2$).

Anal. Calcd.: C, 57.43; H, 4.99; N, 2.31. Found: C, 57.09; H, 4.72; N, 2.34.

M.P. 79°–80° C.

Step (o) Preparation of 4-(2-Amino-2-oxoethyl)-2-[(4-bromo-2-fluorophenyl)methyl]-1,2,3,4-tetrahydro-1,3-dioxo-4-isoquinolinecarboxylic Acid Menthyl Ester (A-Diastereomer)

A mixture of 2-[(4-bromo-2-fluorophenyl)methyl]-1,2,3,4-tetrahydro-4-(menthoxycarbonyl)-1,3-dioxo-4-isoquinolineacetic acid (A-diastereomer, 5.5 g, 9.35 mmol) and SOCl$_2$ (30 mL) was refluxed for 2 hours. The volatiles were removed in vacuo and the acid chloride was dissolved in THF (20 mL). In a second flask was placed a freshly prepared, saturated NH$_3$/THF solution (100 mL) and the contents of the first flask were added slowly. After the addition, the mixture was stirred for 15 minutes, poured into H$_2$O (500 mL), acidified with HCl (2N) and extracted with EtOAc. The organic extracts were dried over MgSO$_4$. Evaporation and purification by flash chromatography (hexane/EtOAc, 1/1) gave a white solid (4.86 g).

NMR (DMSO-d$_6$, 400 MHz): δ 0.44 (q, J=7.4 Hz, 1H, —CHCH$_3$), 0.57 (d, J=6.6 Hz, 3H, —CHCH$_3$), 0.64 (d, J=6.6 Hz, 3H, —CHCH$_3$), 0.71 (d, J=7.4 Hz, 3H, —CHCH$_3$), 0.84–1.04 (m, 3H, menthyl), 1.2–1.4 (m, 2H, menthyl), 1.42–1.58 (m, 3H, menthyl), 3.47 (dd, J=16.57 Hz, 2H, —CH$_2$CONH$_2$), 4.46 (dt, J=10.7 Hz, 3.9 Hz, 1H, —OCH—), 5.05 (dd, J=15.4 Hz, 2H, —NCH$_2$—), 6.87 (s, 1H, —CONH—), 7.27 (m, 2H, Ar—H), 7.43 (d, J=7.8 Hz, 1H, Ar—H), 7.55 (m, 3H, Ar—H, —CONH—), 7.76 (dt, J=7.6 Hz, 1.1 Hz, 1H, Ar—H), 8.13 (dd, J=7.85 Hz, 1.1 Hz, 1H, Ar—H).

IR (KBr, cm$^{-1}$): 3450 (s), 3320 (s), 1730 (s), 1715 (s), 1670 (s), 745 (m).

MS (m/e): 587 (M+H)+, 449 (M+H—menthyl).

Anal. Calcd.: C, 59.29; H, 5.49; N, 4.77. Found: C, 59.29; H, 5.40; N, 4.74.

M.P. 94°–95° C.

The following compound was prepared in substantially the same manner as that of Example 7, Step(o).

4-(2-Amino-2-oxoethyl)-2-[(4-bromo-2-fluorophenyl)-methyl]-6-fluoro-1,2,3,4-tetrahydro-1,3-dioxo-4-isoquinolinecarboxylic Acid Menthyl Ester (A-Diastereomer)

NMR (DMSO-$d_6$, 400 MHz): $\delta$ 0.48 (m, 1H, menthyl), 0.55 (d, J=6.89 Hz, 3H, —CHC$\underline{H}_3$), 0.68 (d, J=6.99 Hz, 3H, —CHC$\underline{H}_3$), 0.7 (m, 1H, menthyl), 0.74 (d, J=6.44 Hz, 3H, —CHC$\underline{H}_3$), 0.84-1.0 (m, 2H, menthyl), 1.25-1.4 (m, 3H, menthyl), 1.45-1.49 (m, 2H, menthyl), 3.45 (d, J=16.6 Hz, 1H, —C$\underline{H}_2$CONH$_2$), 3.57 (d, J=16.6 Hz, 1H, —C$\underline{H}_2$CONH$_2$), 4.47 (dt, J=10.71 Hz, 4.2 Hz, 1H, —OC$\underline{H}$—), 5.1 (dd, J=15.35 Hz, 2H, —NC$\underline{H}_2$—), 6.93 (s, 1$\underline{H}$, —CON$\underline{H}_2$), 7.22-7.3 (m, 2H, Ar—$\underline{H}$), 7.35 (dd, J=9.48 Hz, 2.43 Hz, 1H, Ar—$\underline{H}$), 7.44 (dt, J=8.55 Hz, 2.49 Hz, 1H, Ar—$\underline{H}$), 7.51 (s, 1$\underline{H}$, —CH$_2$CON$\underline{H}_2$), 7.53 (dd, J=9.66 Hz, 1.6 Hz, 1H, Ar—$\underline{H}$), 8.21 (dd, J=8.79 Hz, 5.85 Hz, 1H, Ar—$\underline{H}$).

IR (KBr, cm$^{-1}$): 3450 (s), 3380 (s), 1750 (s), 1725 (s), 1675 (s), 1610 (s).

MS (m/e): 605 (M+H)$^+$, 467 (M+H—menthyl), 423 (M+H—menthyl—CO$_2$).

Anal. Calcd.: C, 57.53; H, 5.16; N, 4.63. Found: C, 57.52; H, 4.99; N, 4.58.

M.P. 93°-94° C.

Step (p) Preparation of 4-(2-Amino-2-oxoethyl)-2[(4-bromo-2-fluorophenyl)methyl]-1,2,3,4-tetrahydro-1,3-dioxo-4-isoquinolinecarboxylic Acid Menthyl Ester (B-Diastereomer)

A mixture of 2-[(4-bromo-2-fluorophenyl)methyl]-1,2,3,4-tetrahydro-4-(menthoxycarbonyl)-1,3-dioxo-4-isoquinolineacetic acid (B-diastereomer, 5.5 g, 9.35 mmol) and SOCl$_2$ (30 mL) was refluxed for 2 hours. The volatiles were removed in vacuo and the residue was dissolved in THF (20 mL). In a second flask was placed a freshly prepared, saturated NH$_3$/THF solution (100 mL), and the contents of the first flask were added slowly. After the addition, the mixture was stirred for 15 minutes, poured into H$_2$O (500 mL), acidified with HCl (2N) and extracted with EtOAc. The organic extracts were dried over MgSO$_4$. Evaporation and purification by flash chromatography (hexane/EtOAc, 1/1 ) gave a white solid (4.75 g).

NMR (DMSO-$d_6$, 200 MHz): $\delta$ 0.14 (d, J=6.6 Hz, 3H, —CHC$\underline{H}_3$), 0.25 (m, 1H, menthyl), 0.4 (d, J=6.8 Hz, 3H, —CHC$\underline{H}_3$), 0.6 (m, 3H, menthyl), 0.77 (d, J=7.0 Hz, 3H, —CHC$\underline{H}_3$), 1.3-1.6 (m, 5H, menthyl), 3.49 (dd, J=16.6 Hz, 2H, —C$\underline{H}_2$CONH$_2$), 4.3 (dt, J=10.6 Hz, 3.8 Hz, 1H, —OC$\underline{H}$—), 4.9 (d, J=14.6 Hz, 1H, —NC$\underline{H}$—), 5.26 (d, J=14.6 Hz, 1H, —NC$\underline{H}$—), 6.85 (s, 1$\underline{H}$, —CON$\underline{H}$), 7.31 (m, 2H, Ar—$\underline{H}$), 7.4 (d, J=7.4 Hz, 1H, Ar—$\underline{H}$), 7.5-7.6 (m, 3H, Ar—$\underline{H}$, —CON$\underline{H}$—), 7.7 (dt, J=7.4 Hz, 2.0 Hz, 1H, Ar—$\underline{H}$), 8.14 (dd, J=7.4 Hz, 1.6 Hz, 1H, Ar—$\underline{H}$).

IR (KBr, cm$^{-1}$): 3460 (s), 3315 (s), 1735 (s), 1715 (s), 1675 (s), 745 (s).

MS (m/e): 587 (M+H)$^+$, 449 (M+H—menthyl).

Anal. Calcd.: C, 59.29; H, 5.49; N, 4.77. Found: C, 59.40; H, 5.39; N, 4.76.

M.P. 151°-152° C.

The following compound was prepared in substantially the same manner as that of Example 7, Step (p).

4-(2-Amino-2-oxoethyl)-2-[(4-bromo-2-fluorophenyl)-methyl]-6-fluoro-1,2,3,4-tetrahydro-1,3-dioxo-4-isoquinolinecarboxylic Acid Menthyl Ester (B-Diastereomer)

NMR (DMSO-$d_6$, 400 MHz): $\delta$ 0.19 (d, J=6.89 Hz, 3H, —CHC$\underline{H}_3$), 0.21 (m, 1H, menthyl), 0.45 (d, J=6.95 Hz, 3H, —CHC$\underline{H}_3$), 0.6 (m, 1H, menthyl), 0.7 (m, 1H, menthyl), 0.78 (d, J=6.52 Hz, 3H, —CHC$\underline{H}_3$), 0.8-0.9 (m, 2H, menthyl), 1.3 (m, 1H, menthyl), 1.43 (m, 1H, menthyl), 1.5-1.57 (m, 2H, menthyl), 3.43 (d, J=16.67 Hz, 1H, —C$\underline{H}_2$CONH$_2$), 3.55 (d, J=16.67 Hz, 1H, —C$\underline{H}_2$CONH$_2$), 4.3 (dt, J=10.49 Hz, 6.42 Hz, 1H, —OC$\underline{H}$—), 4.9 (d, J=14.78 Hz, 1H, —NC$\underline{H}_2$—), 5.3 (d, J=14.78 Hz, 1H, —NC$\underline{H}_2$—), 6.09 (s, 1$\underline{H}$, —CON$\underline{H}_2$), 7.26-7.34 (m, 3H, Ar—$\underline{H}$), 7.43 (dt, J=8.57 Hz, 2.43 Hz, 1H, Ar—$\underline{H}$), 7.50 (s, 1$\underline{H}$, —CON$\underline{H}_2$), 7.53 (dd, J=9.6 Hz, 1.73 Hz, 1H, Ar—$\underline{H}$), 8.24 (dd, J=8.81 Hz, 5.9 Hz, 1H, Ar—$\underline{H}$).

IR (KBr, cm$^{-1}$): 3485 (s), 3360 (s), 1740 (s), 1730 (s), 1685 (s), 1675 (s), 1615 (s).

MS (m/e): 605 (M+H)$^+$, 467 (M+H—menthyl), 423 (M+H—menthyl—CO$_2$).

Anal. Calcd.: C, 57.53; H, 5.16; N, 4.63. Found: C, 57.62; H, 4.89; N, 4.58.

M.P. 111°-112° C.

Step (q) Preparation of (S)-(—)-2-[(4-Bromo-2-fluorophenyl)methyl]spiro[isoquinoline-4(1H),3'-pyrrolidine]-1,2',3,5'(2H)-tetrone To a cold (—78° C.) solution of 4-(2-amino-2-oxoethyl)-2-[(4-bromo-2-fluorophenyl)methyl]-1,2,3,4-tetrahydro-1,3-dioxo-4-isoquinolinecarboxylic acid menthyl ester (A-diastereomer, 3.5 g, 5.96 mmol) in anhydrous THF (80 mL) was added lithium bis(trimethylsilyl)amide (1.0M in THF, 5.96 mL, 5.96 mmol) dropwise over a 5 minute period. After stirring at —78° C. for 20 minutes, the reaction was quenched with HCl (2N) and the mixture was poured into H$_2$O and extracted with EtOAc. The organic extracts were dried over MgSO$_4$. Evaporation and purification by flash chromatography on acid-washed silica gel (5% H$_3$PO$_4$ in MeOH) gave a white solid, which was recrystallized once from ethyl ether (at —20° C.) to yield a crystalline white solid (1.1 g). The enantiomeric purity was determined by analytical HPLC (Chiralcel OB) and was found to be greater than 99% (99.6% ee).

NMR (DMSO-$d_6$, 400 MHz): $\delta$ 3.4 (dd, J=18.35 Hz, 2H, —C$\underline{H}_2$CONH—), 5.06 (s, 2H, —NC$\underline{H}_2$—), 7.14 (t, J=8.21 Hz, 1H, Ar—$\underline{H}$), 7.32 (dd, J=8.34 Hz, 1.67 Hz, 1H, Ar—$\underline{H}$), 7.53 (dd, J=9.83 Hz, 1.87 Hz, 1H, Ar—$\underline{H}$), 7.6 (dt, J=7.85 Hz, 1.03 Hz, 1H, Ar—$\underline{H}$), 7.68 (d, J=7.76 Hz, 1H, Ar—$\underline{H}$), 7.77 (dt, J=7.53 Hz, 1.34 Hz, 1H, Ar—$\underline{H}$), 8.15 (dd, J=7.88 Hz, 1.25 Hz, 1H, Ar—$\underline{H}$), 12.01 (s, 1$\underline{H}$, —CON$\underline{H}$CO—).

IR (KBr, cm$^{-1}$): 3340 (s), 1735 (s), 1710 (s), 1675 (s), 1490 (m), 1340 (s), 810 (m), 755 (m).

MS (m/e): 430 (M$^+$), 387 (M$^+$—CONH).

Anal. Calcd.: C, 52.92; H, 2.80; N, 6.50. Found: C, 53.01; H, 2.75; N, 6.45.

$[\alpha]_D^{25}$ = —63.3 (c=1.02, EtOAc).

M.P. 175°-176° C.

The following compound was prepared in substantially the same manner as that of Example 7, Step (q).

(S)-(-)-[2-[(4-Bromo-2-fluorophenyl)methyl]-6-fluoro]spiro[isoquinoline-4(1H),3'-pyrrolidine]-1,2',3,5'(2H)-tetrone NMR (DMSO-d$_6$, 400 MHz): δ 3.43 (s, 2H, —CH$_2$CONH—), 5.05 (s, 2H, —NCH$_2$—), 7.13 (t, J=$\overline{8.26}$ Hz, 1H, Ar—H), 7.33 (dd, J=$\overline{8.3}$ Hz, 1.81 Hz, 1H, Ar—H), 7.47 (dt, J=8.57 Hz, 2.4 Hz, 1H, Ar—H), 7.53 (dd, $\overline{J}$=9.8 Hz, 1.9 Hz, 1H, Ar—H), 7.75 (dd, J=$\overline{9.8}$ Hz, 2.4 Hz, 1H, Ar—H), 8.22 (dd, J=$\overline{8.81}$ Hz, 5.83 Hz, 1H, Ar—H), 12.0 (s, $\overline{1H}$, —CONHCO—).

IR (KBr, cm$^{-1}$): 3325 (s), $\overline{1740}$ (s), 1715 (s), 1675 (s), 1335 (s), 710 (m).

MS (m/e): 449 (M+H)$^+$.

Anal. Calcd.: C, 50.80; H, 2.47; N, 6.24. Found: C, 51.00; H, 2.64; N, 6.11.

[α]$_D^{25}$ = −41.9 (c=1.0, EtOAc).

M.P. 247°–248° C.

Step (r) Preparation of (R)-(+)-2-[(4-Bromo-2-fluorophenyl)methyl]spiro[isoquinoline-4(1H),3'-pyrrolidine]-1,2',3,5'(2H)-tetrone To a cold (−78° C.) solution of 4-(2-amino-2-oxoethyl)-2-[(4-bromo-2-fluorophenyl)methyl]-1,2,3,4-tetrahydro-1,3-dioxo-4-isoquinolinecarboxylic acid menthyl ester (B-diastereomer, 3.0 g, 5.11 mmol) in anhydrous THF (60 mL) was added lithium bis(trimethylsilyl)amide (1.0M in THF, 5.11 mL, 5.11 mmol) dropwise over a 5 minute period. After stirring at −78° C. for 20 minutes, the reaction was quenched with HCl (2N) and the mixture was poured into H$_2$O and extracted with EtOAc. The organic extracts were dried over MgSO$_4$. Evaporation and purification by flash chromatography on acid-washed silica gel (5% H$_3$PO$_4$ in MeOH) gave a white solid, which was recrystallized once from ethyl ether (at −20° C.) to yield a crystalline white solid (1.2 g). The enantiomeric purity was determined by analytical HPLC (Chiralcel OB) and was found to be greater than 99% (99.2% ee).

NMR (DMSO-d$_6$, 400 MHz): δ 3.4 (dd, J=18.35 Hz, 2H, —CH$_2$CONH—), 5.06 (s, 2H, —NCH$_2$—), 7.14 (t, J=8.21 Hz, 1H, Ar—H), 7.32 (dd, J=8.34 Hz, 1.67 Hz, 1H, Ar—H), 7.5 (dd, $\overline{J}$=9.83 Hz, 1.87 Hz, 1H, Ar—H), 7.6 (dt, $\overline{J}$=7.85 Hz, 1.03 Hz, 1H, Ar—H), 7.68 $\overline{(d,}$ J=7.76 Hz, 1H, Ar—H), 7.77 (dt, J=7.53 $\overline{Hz}$, 1.34 Hz, 1H, Ar—H), 8.15 (dd, $\overline{J}$=7.88 Hz, 1.25 Hz, 1H, Ar—H), 12.01 (s, $\overline{1H}$, —CONHCO—).

IR (KBr, cm$^{-1}$): 3$\overline{340}$ (s), 1735 (s), 1710 (s), 1675 (s), 1490 (m), 1340 (s), 810 (m), 755 (m).

MS (m/e): 430 (M$^+$), 387 (M$^+$—CONH).

Anal. Calcd.: C, 52.92; H, 2.80; N, 6.50. Found: C, 52.75; H, 2.54; N, 6.26.

[α]$_D^{25}$ = +62.3 (c=0.8, EtOAc).

M.P. 175°–176° C.

The following compound was prepared in substantially the same manner as that of Example 7, Step (r).

(R)-(+)-[2-[(4-Bromo-2-fluorophenyl)methyl]-6-fluoro]spiro[isoquinoline-4(1H),3'-pyrrolidine]-1,2',3,5'(2H)-tetrone NMR (DMSO-d$_6$, 400 MHz): δ 3.43 (s, 2H, —CH$_2$CONH—), 5.05 (s, 2H, —NCH$_2$—), 7.13 (t, J=$\overline{8.26}$ Hz, 1H, Ar—H), 7.33 (dd, J=$\overline{8.3}$ Hz, 1.81 Hz, 1H, Ar—H), 7.47 (dt, J=8.57 Hz, 2.4 Hz, 1H, Ar—H), 7.53 (dd, $\overline{J}$=9.8 Hz, 1.9 Hz, 1H, Ar—H), 7.75 (dd, J=$\overline{9.8}$ Hz, 2.4 Hz, 1H, Ar—H), 8.22 (dd, J=$\overline{8.81}$ Hz, 5.83 Hz, 1H, Ar—H), 12.0 (s, $\overline{1H}$, —CONHCO—).

IR (KBr, cm$^{-1}$): 3325 (s), $\overline{1740}$ (s), 1715 (s), 1675 (s), 1335 (s), 710 (m).

MS (m/e): 449 (M+H)$^+$

Anal. Calcd.: C, 50.80; H, 2.47; N, 6.24. Found: C, 51.06; H, 2.64; N, 6.12.

[α]$_D^{25}$ = +40.4 (c=1.01, EtOAc).

M.P. 247°–248° C.

EXAMPLE 8

The crystals of (−)-2-[(4-bromo-2-fluorophenyl)methyl]spiro[isoquinoline-4(1H),3'-pyrrolidine]-1,2',3,5'(2H)-tetrone, were obtained from ethyl ether. The data were measured at room temperature on a Nicolet R3m diffractometer using a crystal of dimensions 0.35×0.42×0.50 mm and Cukα (λ=1.54178Å) radiation. An n refinement was carried out to determine the absolute configuration. The value for n refined to 1.04 for the structure with C(4)S stereochemistry indicating that to be the correct absolute stereochemistry [D. Rogers; Acta. Cryst. A37, 734, (1981)].

We claim:

1. The compound of structural formula (I)

wherein R$^1$ and R$^2$ are independently hydrogen, alkyl containing 1 to 6 carbon atoms, halogen, lower alkoxy containing 1 to 6 carbon atoms, trifluoromethyl, lower alkylthio wherein lower alkyl contains 1 to 6 carbon atoms, dialkylamino wherein alkyl contains 1 to 6 carbon atoms, nitro, aryl or aryl (lower alkyl) oxy wherein aryl contains 6 to 10 carbon atoms and lower alkyl contains 1 to 6 carbon atoms; R$^3$ is hydrogen, lower alkyl containing 1 to 6 carbon atoms, aryl (lower alkyl) or halogen substituted aryl (lower alkyl) wherein aryl contains 6 to 10 carbon atoms and lower alkyl contains 1 to 6 carbon atoms, acyl or heterocyclic (lower alkyl) of structural formula wherein R$^4$ is lower alkylene containing 1 to 3 carbon atoms; X is methylene, oxygen, sulfur or nitrogen; Y and Z are oxygen or sulfur; M and W are carbonyl, thiocarbonyl, sulfonyl, sulfoxo or, methylene, with the proviso that M and W are not both methylene when X is nitrogen, and the pharmaceutically acceptable salts thereof.

2. The compounds according to claim 1 of the structural formula (II)

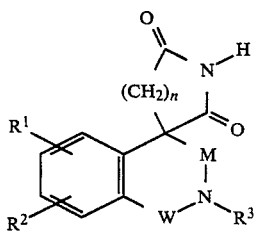

wherein $R^1$ and $R^2$ are independently hydrogen, alkyl containing 1 to 6 carbon atoms, halogen, lower alkoxy containing 1 to 6 carbon atoms, trifluoromethyl, lower alkylthio wherein lower alkyl contains 1 to 6 carbon atoms; $R^3$ is hydrogen, lower alkyl containing 1 to 6 carbon atoms; M and W are carbonyl or thiocarbonyl; n is 1, and the pharmaceutically acceptable salts thereof.

3. The compounds according to claim 1 of structural formula (II)

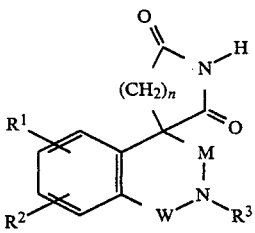

wherein $R^1$ and $R^2$ are independently hydrogen, alkyl containing 1 to 6 carbon atoms, halogen, lower alkoxy containing 1 to 6 carbon atoms, trifluoromethyl, lower alkythio wherein lower alkyl contains 1 to 6 carbon atoms; $R^3$ is aryl(lower alkyl) or dihalogen substituted aryl(lower alkyl) wherein aryl contains 6 to 10 carbon atoms and lower alkyl contains 1 to 6 carbon atoms; M and W are carbonyl or thiocarbonyl; n is 1, and the pharmaceutically acceptable salts thereof.

4. The compounds according to claim 1 of structural formula (III)

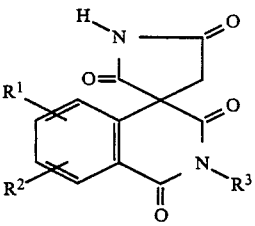

wherein $R^1$ and $R^2$ are hydrogen or halogen; $R^3$ is lower alkyl containing 1 to 6 carbon atoms, benzyl or dihalogen substituted benzyl, and the pharmaceutically acceptable salts thereof.

5. The compound according to claim 4 designated 2-[(4-bromo-2-fluorophenyl)methyl]spiro[isoquinoline-4(1H),3'-pyrrolidine]-1,2',3,5'(2H)-tetrone, and the pharmaceutically acceptable salts thereof.

6. The compound according to claim 4 designated [2-[(4-bromo-2-fluorophenyl)methyl]-7-chloro]-spiro[isoquinoline-4(1H),3'-pyrrolidine]-1,2',3,5'(2H)-tetrone, and the pharmaceutically acceptable salts thereof.

7. The compound according to claim 4 designated [2-[(4-bromo-2-fluorophenyl)methyl]-6-chloro]-spiro[isoquinoline-4(1H),3'-pyrrolidine]-1,2',3,5'(2H)-tetrone, and the pharmaceutically acceptable salts thereof.

8. The compound according to claim 4 designated 2-[(3,4-dichlorophenyl)methyl]spiro[isoquinoline-4(1H),3'-pyrrolidine)-1,2',3,5'(2H)-tetrone, and the pharmaceutically acceptable salts thereof.

9. The compound according to claim 4 designated [2-[(4-bromo-2-fluorophenyl)methyl]-5-fluoro]-spiro[isoquinoline-4(1H),3'-pyrrolidine]-1,2',3,5'(2H)-tetrone, and the pharmaceutically acceptable salts thereof.

10. The compound according to claim 4 designated [2-[(4-bromo-2-fluorophenyl)methyl]-6-fluoro]-spiro[isoquinoline-4(1H),3'-pyrrolidine]-1,2',3,5'(2H)-tetrone, and the pharmaceutically acceptable salts thereof.

11. The compound according to claim 4 designated [2-[(4-bromo-2-fluorophenyl)methyl]-7-fluoro]-spiro[isoquinoline-4-(1H),3'-pyrrolidine]-1,2',3,5'(2H)-tetrone, and the pharmaceutically acceptable salts thereof.

12. The compound according to claim 4 designated [2-[(4-bromo-2-fluorophenyl)methyl]-8-fluoro]-spiro[isoquinoline-4(1H),3'-pyrrolidine]-1,2',3,5'(2H)-tetrone, and the pharmaceutically acceptable salts thereof.

13. The compound according to claim 4 designated [6-bromo-2-[(4-bromo-2-fluorophenyl)methyl]-7-methoxy]spiro[isoquinoline-4(1H),3'-pyrrolidine]-1,2',3,5'(2H)-tetrone, and the pharmaceutically acceptable salts thereof.

14. The compound according to claim 4 designated [2-[(4-bromo-2-fluorophenyl)-methyl]-7-methoxy]-spiro[isoquinoline-4(1H),3'-pyrrolidine]-1,2',3,5'(2H)-tetrone, and the pharmaceutically acceptable salts thereof.

15. The compound according to claim 4 designated (R)-(+)-2-[(4-bromo-2-fluorophenyl)methyl]-spiro[isoquinoline-4(1H),3'-pyrrolidine]-1,2',3,5'(2H)-tetrone, and the pharmaceutically acceptable salts thereof.

16. The compound according to claim 4 (S)-(−)-2-[(4-bromo-2-fluorophenyl)methyl]spiro[isoquinoline-4(1H),3'-pyrrolidine]-1,2',3,5'(2H)-tetrone, and the pharmaceutically acceptable salts thereof.

17. The compound according to claim 4 (R)-(+)-[2-[(4-bromo-2-fluorophenyl)methyl]-6-fluoro]-spiro[isoquinoline-4(1H),3'-pyrrolidine]-1,2',3,5'(2H)-tetrone, and the pharmaceutically acceptable salts thereof.

18. The compound according to claim 4 designated (S)-(−)-[2-[(4-bromo-2-fluorophenyl)methyl]-6-fluoro]-spiro[isoquinoline-4(1H),3'-pyrrolidine]-1,2',3,5'(2H)-tetrone, and the pharmaceutically acceptable salts thereof.

19. The compound according to claim 4 designated 2-methylspiro[isoquinoline-4(1H),3'-pyrrolidine]-1,2',3,5'(2H)-tetrone, and the pharmaceutically acceptable salts thereof.

20. The compound according to claim 4 designated 6-chloro-2-methylspiro[isoquinoline-4(1H),3'-pyrrolidine]-1,2',3,5'(2H)-tetrone, and the pharmaceutically acceptable salts thereof.

21. The compound according to claim 4 designated 6-bromo-2-methylspiro[isoquinoline-4(1H),3'-pyrrolidine]-1,2',3,5'(2H)-tetrone, and the pharmaceutically acceptable salts thereof.

22. The compound according to claim 4 designated 7-chloro-2-methylspiro[isoquinoline-4(1H),3'-pyrrolidine]-1,2',3,5'(2H)-tetrone, and the pharmaceutically acceptable salts thereof.

23. The compound according to claim 4 designated 2-ethylspiro[isoquinoline-4(1H),3'-pyrrolidine]1,2',3,5'(2H)-tetrone, and the pharmaceutically acceptable salts thereof.

24. The compound according to claim 4 designated 2-propylspiro[isoquinoline-4(1H),3'-pyrrolidine]-1,2',3,5'(2H)-tetrone, and the pharmaceutically acceptable salts thereof.

25. The compound according to claim 4 designated 2-butylspiro[isoquinoline-4(1H),3'-pyrrolidine]-1,2',3,5'(2H)-tetrone, and the pharmaceutically acceptable salts thereof.

26. The process for the production of compounds of formula (XI)

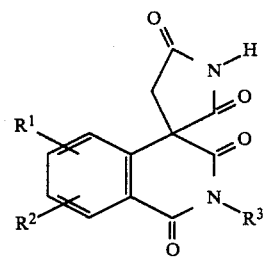

wherein $R^1$ and $R^2$ are hydrogen or halogen; $R^3$ is alkyl containing 1 to 6 carbon atoms, aryl (lower alkyl) or dihalogen substituted aryl (lower alkyl) wherein aryl contains 6 to 10 carbon atoms and lower alkyl contains 1 to 6 carbon atoms, which comprises:

(a) reacting the compound of formula (VI)

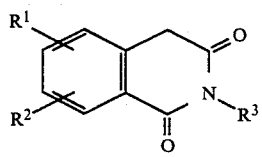

wherein $R^1$, $R^2$, and $R^3$ are as defined above, with a base in a conventional solvent and subsequently adding a reactive carbomethoxylating agent to produce the compound of formula (VII)

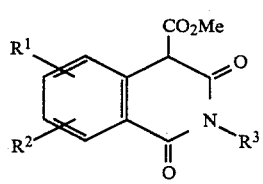

wherein $R^1$, $R^2$, and $R^3$ are as defined above;
(b) reacting said compound of formula (VII) with an inorganic base in a conventional solvent and subsequently adding tert-butyl bromoacetate to produce the compound of the formula (VIII)

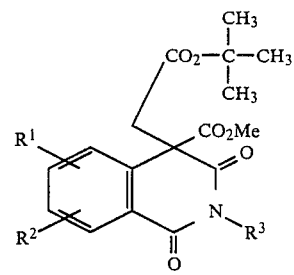

wherein $R^1$, $R^2$, and $R^3$ are as defined above;
(c) hydrolyzing said compound of formula (VIII) with an organic acid in a conventional solvent to produce the compound of formula (IX)

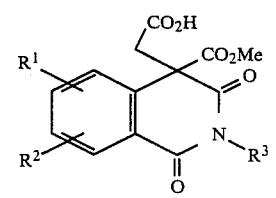

wherein $R^1$, $R^2$, and $R^3$ are as defined above;
(d) reacting said compound of formula (IX) with a coupling agent in a conventional solvent and subsequently adding tetrahydrofuran ammonium solution to produce the compound of formula (X)

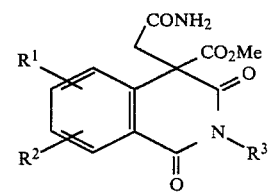

wherein $R^1$, $R^2$, and $R^3$ are as defined above;
(e) reacting said compound of formula (X) with a base in a conventional solvent to produce the compound of formula (XI).

27. The process according to claim 15 for the production of compounds of formula (XI), wherein $R^1$ and $R^2$ are as defined in claim 15, and $R^3$ is alkyl containing 1 to 6 carbon atoms, wherein the compound of formula (X), wherein $R^1$ and $R^2$ are as defined above, $R^3$ is an alkyl, as defined above, is reacted with a base, such as lithium bis(trimethylsilyl)amide, in a conventional solvent to produce the compound of the formula (XI), wherein $R^1$ and $R^2$ are as defined above, and $R^3$ is an alkyl, as defined above.

28. The process for the production of compounds of formula (VII)

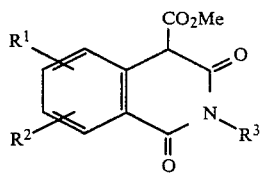

wherein $R^1$ and $R^2$ are hydrogen or halogen; $R^3$ is alkyl containing 1 to 6 carbon atoms, aryl(lower alkyl) or dihalogen substituted aryl(lower alkyl) wherein aryl contains 6 to 10 carbon atoms and lower alkyl contains 1 to 6 carbon atoms which comprises reacting the compound of formula (XII)

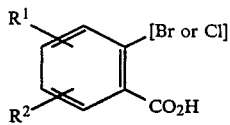 (XII)

wherein $R^1$ and $R^2$ are as defined above with dimethyl malonate and NaH in the presence of a catalytic amount of CuBr to produce the compound of formula (XIII)

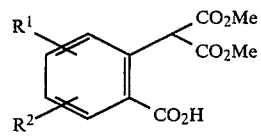 (XIII)

wherein $R^1$ and $R^2$ are as defined above and reacting said compound of formula (XIII) with thionyl chloride and subsequently adding tetrahydrofuran ammonium solution to produce the compound of formula (VII).

29. A pharmaceutical composition for preventing or relieving neuropathy, nephropathy, retinopathy, or cataracts in a diabetic mammal, which comprises an effective amount of a compound of claim 1 and a pharmaceutically acceptable carrier.

30. A method of preventing or relieving neuropathy, nephropathy, retinopathy, or cataracts in a diabetic mammal, which comprises administering to said mammal an alleviating or prophylactic amount of a compound of claim 1.

* * * * *